United States Patent
Keil et al.

(10) Patent No.: US 7,468,369 B2
(45) Date of Patent: Dec. 23, 2008

(54) SULFONYL PYRROLIDINES, METHOD FOR PRODUCING THE SAME AND THEIR USE AS DRUGS

(75) Inventors: Stefanie Keil, Hofheim (DE); Hans-Ludwig Schaefer, Hochheim (DE); Maike Glien, Wiesbaden (DE); Stefan Guessregen, Wiesbadan (DE); Wolfgang Wendler, Selters (DE); Marion Schneider, Hofheim (DE)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/765,705

(22) Filed: Jun. 20, 2007

(65) Prior Publication Data

US 2008/0045540 A1 Feb. 21, 2008

Related U.S. Application Data

(63) Continuation of application No. PCT/EP2005/013772, filed on Dec. 21, 2005.

(30) Foreign Application Priority Data

Jan. 4, 2005 (DE) .................. 10 2005 000 666

(51) Int. Cl.
*A61K 31/496* (2006.01)
*C07D 401/04* (2006.01)
*C07D 401/14* (2006.01)
*C07D 413/12* (2006.01)
*C07D 413/14* (2006.01)
*C07D 409/04* (2006.01)
*C07D 207/48* (2006.01)

(52) U.S. Cl. .................. 514/252.13; 514/253.07; 514/253.09; 514/254.03; 514/254.04; 544/363; 544/367; 544/372; 544/105

(58) Field of Classification Search ............. None
See application file for complete search history.

(56) References Cited

U.S. PATENT DOCUMENTS 6,335,334 B1  1/2002  Schindler et al.
6,548,547 B1  4/2003  Schindler et al.

FOREIGN PATENT DOCUMENTS

WO  WO 94/07496  4/1994
WO  WO 2005/040109  5/2005

OTHER PUBLICATIONS

Davidson, Expert Opin.Ther.Targets,vol. 8, pp. 359-366 (2004).*
Suckling, Expert Opin.Ther.Targets,vol. 11, pp. 1133-1136 (2007).*

* cited by examiner

*Primary Examiner*—Emily Bernhardt
(74) *Attorney, Agent, or Firm*—Balaram Gupta

(57) ABSTRACT

The invention relates to substituted sulfonylpyrrolidines of the formula I

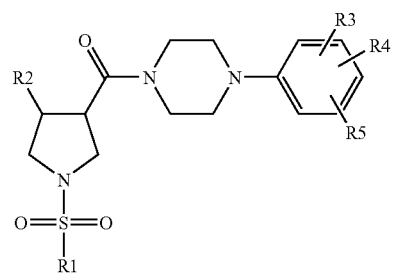

and to the physiologically tolerated salts thereof, as well as to their use as medicaments.

7 Claims, No Drawings

SULFONYL PYRROLIDINES, METHOD FOR PRODUCING THE SAME AND THEIR USE AS DRUGS

CROSS REFERENCE TO RELATED APPLICATIONS

This application is a continuation of International application No. PCT/EP 2005/013,772, filed Dec. 21, 2005, which is incorporated herein by reference in its entirety; which claims the benefit of priority of German Patent Application No. 102005000666.3, filed Jan. 4, 2005.

FIELD OF THE INVENTION

The invention relates to substituted sulfonylpyrrolidines and to the physiologically tolerated salts thereof.

BACKGROUND OF THE INVENTION

Compounds of similar structure have been described as oxytocin receptor antagonists in WO 94/07496.

The invention was based on the object of providing compounds with which it is possible to prevent and treat dyslipidemia, disorders of the cardiovascular system and atherosclerotic disorders. It was particularly intended that the compounds be suitable for the prevention and treatment of lower HDL levels (HDL means high density lipoproteins).

DETAILED DESCRIPTION

The invention therefore relates to compounds of the formula I

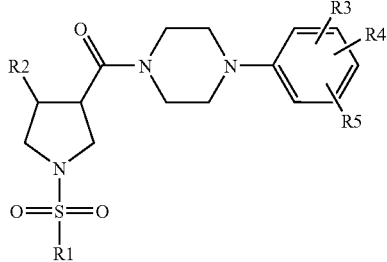

I in which the meanings are

R1 ($C_1$-$C_6$)-alkyl, where one or more hydrogens in the alkyl radical may be replaced by fluorine, or phenyl, ($C_1$-$C_8$)-alkylene-phenyl, heterocycle, ($C_1$-$C_8$)-alkylene-heterocycle, where the phenyl or heterocycle radical may be substituted one or more times by F, Cl, Br, $NO_2$, COO—($C_1$-$C_6$)-alkyl, ($C_1$-$C_6$)-alkylene-O—($C_1$-$C_6$)-alkyl, $OCF_3$, ($C_1$-$C_6$)-alkyl, CO—($C_1$-$C_6$)-alkyl, phenyl, $SCF_3$, $SF_5$;

R2 ($C_1$-$C_6$)-alkyl, phenyl, ($C_1$-$C_8$)-alkylene-phenyl, heterocycle, ($C_1$-$C_8$)-alkylene-heterocycle, where the phenyl or heterocycle radical may be substituted one or more times by F, Cl, Br, $NO_2$, COO—($C_1$-$C_6$)-alkyl, ($C_1$-$C_6$)-alkylene-O—($C_1$-$C_6$)-alkyl, $OCF_3$, ($C_1$-$C_6$)-alkyl, CO—($C_1$-$C_6$)-alkyl, phenyl, $SCF_3$, $SF_5$;

R3, R4, R5 independently of one another H, F, Cl, Br, $NO_2$, COO—($C_1$-$C_6$)-alkyl, ($C_1$-$C_6$)-alkylene-O—($C_1$-$C_6$)-alkyl, $OCF_3$, ($C_1$-$C_6$)-alkyl, CO—($C_1$-$C_6$)-alkyl, phenyl, $SCF_3$, $SF_5$;

where the compounds of the following four formulae are excluded

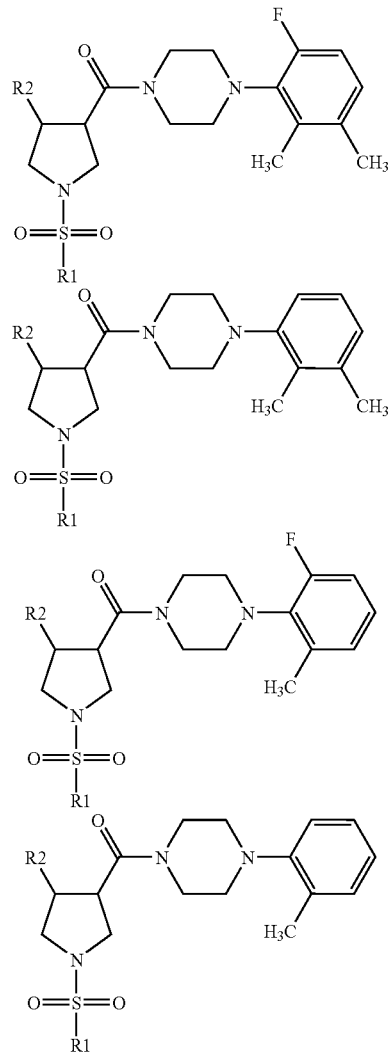

and the physiologically tolerated salts thereof.

Preference is given to compounds of the formula I in which one or more radicals have the following meaning:

R1 ($C_1$-$C_6$)-alkyl, where one or more hydrogens in the alkyl radical may be replaced by fluorine, or phenyl, ($C_1$-$C_8$)-alkylene-phenyl, heterocycle, ($C_1$-$C_8$)-alkylene-heterocycle, where the phenyl or heterocycle radical may be substituted one or more times by F, Cl, Br, $NO_2$, COO—($C_1$-$C_6$)-alkyl, ($C_1$-$C_6$)-alkylene-O—($C_1$-$C_6$)-alkyl, $OCF_3$, ($C_1$-$C_6$)-alkyl, CO—($C_1$-$C_6$)-alkyl, phenyl, $SCF_3$, $SF_5$;

R2 phenyl, heterocycle, where the phenyl or heterocycle radical may be substituted one or more times by F, Cl, Br, $NO_2$, COO—($C_1$-$C_6$)-alkyl, ($C_1$-$C_6$)-alkylene-O—($C_1$-$C_6$)-alkyl, $OCF_3$, ($C_1$-$C_6$)-alkyl, CO—($C_1$-$C_6$)-alkyl, phenyl, $SCF_3$, $SF_5$;

R3, R4, R5 independently of one another H, F, Cl, Br, $NO_2$, COO—($C_1$-$C_6$)-alkyl, ($C_1$-$C_6$)-alkylene-O—($C_1$-$C_6$)-alkyl, $OCF_3$, ($C_1$-$C_6$)-alkyl, CO—($C_1$-$C_6$)-alkyl, phenyl, $SCF_3$, $SF_5$;

where the compounds of the following four formulae are excluded

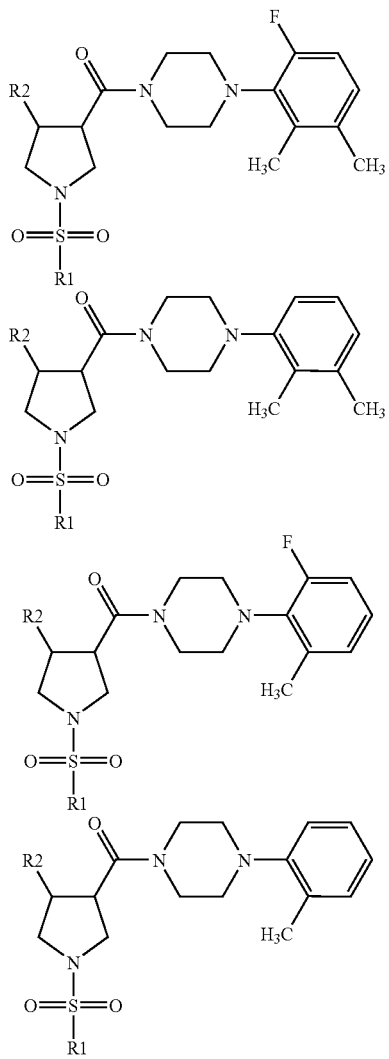

and the physiologically tolerated salts thereof.

Particular preference is given to compounds of the formula I having the structure Ia:

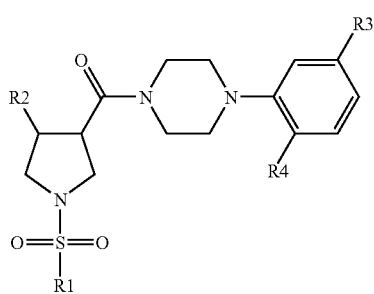

in which one or more radicals have the following meaning:
R1 ($C_1$-$C_6$)-alkyl, where one or more hydrogens in the alkyl radical may be replaced by fluorine, or phenyl, ($C_1$-$C_8$)-alkylene-phenyl, heterocycle, ($C_1$-$C_8$)-alkylene-heterocycle, where the phenyl or heterocycle radical may be substituted one or more times by F, Cl, Br, $NO_2$, COO—($C_1$-$C_6$)-alkyl, ($C_1$-$C_6$)-alkylene-O—($C_1$-$C_6$)-alkyl, $OCF_3$, ($C_1$-$C_6$)-alkyl, CO—($C_1$-$C_6$)-alkyl, phenyl, $SCF_3$, $SF_5$;

R2 phenyl, heterocycle, where the phenyl or heterocycle radical may be substituted one or more times by F, Cl, Br, $NO_2$, COO—($C_1$-$C_6$)-alkyl, ($C_1$-$C_6$)-alkylene-O—($C_1$-$C_6$)-alkyl, $OCF_3$, ($C_1$-$C_6$)-alkyl, CO—($C_1$-$C_6$)-alkyl, phenyl, $SCF_3$, $SF_5$;

R3, R4, independently of one another H, F, Cl, Br, $NO_2$, COO—($C_1$-$C_6$)-alkyl, ($C_1$-$C_6$)-alkylene-O—($C_1$-$C_6$)-alkyl, $OCF_3$, ($C_1$-$C_6$)-alkyl, CO—($C_1$-$C_6$)-alkyl, phenyl, $SCF_3$, $SF_5$;

where the compound of the following formula is excluded

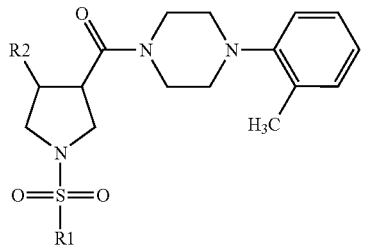

and the physiologically tolerated salts thereof.

Very particular preference is given to compounds of the formula I having the structure Ia:

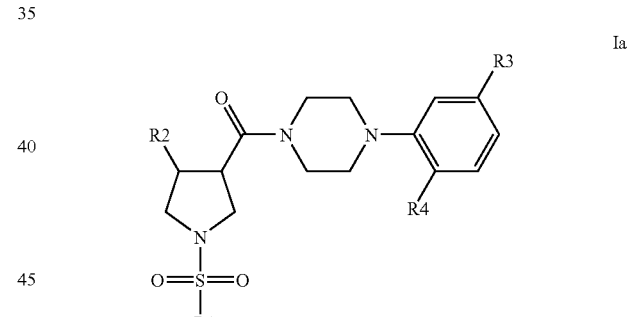

in which one or more radicals have the following meaning:
R1 ($C_1$-$C_6$)-alkyl, where one or more hydrogens in the alkyl radical may be replaced by fluorine, or phenyl, ($C_1$-$C_8$)-alkylene-phenyl, heterocycle, ($C_1$-$C_8$)-alkylene-heterocycle, where the phenyl or heterocycle radical may be substituted one or more times by F, Cl, Br, $NO_2$, COO—($C_1$-$C_6$)-alkyl, ($C_1$-$C_6$)-alkylene-O—($C_1$-$C_6$)-alkyl, $OCF_3$, ($C_1$-$C_6$)-alkyl, CO—($C_1$-$C_6$)-alkyl, phenyl, $SCF_3$, $SF_5$ and the heterocycle is selected from the group of thiophene, quinoline, oxadiazole, isoxazole and pyridine and may be fused to a benzene ring.

R2 phenyl, heterocycle, where the phenyl or heterocycle radical may be substituted one or more times by F, Cl, Br, $NO_2$, COO—($C_1$-$C_6$)-alkyl, ($C_1$-$C_6$)-alkylene-O—($C_1$-$C_6$)-alkyl, $OCF_3$, ($C_1$-$C_6$)-alkyl, CO—($C_1$-$C_6$)-alkyl, phenyl, $SCF_3$, $SF_5$ and the heterocycle is selected from the group of dioxole, tetrahydrofuran, isoxazole, oxazine, thiophene and pyridine and may be fused to a benzene ring.

R3, R4, independently of one another H, F, Cl, Br, $NO_2$, COO—$(C_1$-$C_6)$-alkyl, $(C_1$-$C_6)$-alkylene-O—$(C_1$-$C_6)$-alkyl, $OCF_3$, $(C_1$-$C_6)$-alkyl, CO—$(C_1$-$C_6)$-alkyl, phenyl, $SCF_3$, $SF_5$;

where the compound of the following formula is excluded and the physiologically tolerated salts thereof.

The invention relates to compounds of the formula I in the form of their racemates, racemic mixtures and pure enantiomers, and to their diastereomers and mixtures thereof.

If radicals or substituents may occur more than once in the compounds of the formula I, they may all, independently of one another, have the stated meanings and be identical or different.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydro-chloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

A further aspect of the invention are physiologically functional derivatives of the compounds of the formula I. The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives include prodrugs of the compounds of the invention, such as those described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

An alkyl radical means a straight-chain or branched hydrocarbon chain having one or more carbons, such as, for example, methyl, ethyl, isopropyl, tert-butyl, hexyl.

The alkyl radicals may be substituted one or more times by suitable groups such as, for example:

F, Cl, Br, I, $CF_3$, $NO_2$, $N_3$, CN, COOH, COO$(C_1$-$C_6)$alkyl, $CONH_2$, CONH$(C_1$-$C_6)$alkyl, CON[$(C_1$-$C_6)$alkyl]$_2$, cycloalkyl, $(C_2$-$C_6)$-alkenyl, $(C_2$-$C_6)$-alkynyl, O—$(C_1$-$C_6)$-alkyl O—CO—$(C_1$-$C_6)$-alkyl, O—CO—$(C_1$-$C_6)$-aryl, O—CO—$(C_1$-$C_6)$-heterocycle;

$PO_3H_2$, $SO_3H$, $SO_2$—$NH_2$, $SO_2NH(C_1$-$C_6)$-alkyl, $SO_2N$[$(C_1$-$C_6)$-alkyl]$_2$, S—$(C_1$-$C_6)$-alkyl, S—$(CH_2)_n$-aryl, S—$(CH_2)_n$-heterocycle, SO—$(C_1$-$C_6)$-alkyl, SO—$(CH_2)_n$-aryl, SO—$(CH_2)_n$-heterocycle, $SO_2$—$(C_1$-$C_6)$-alkyl, $SO_2$—$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—N$(C_1$-$C_6)$-alkyl)$(CH_2)_n$-aryl, $SO_2$—N$(C_1$-$C_6)$-alkyl)$(CH_2)_n$-heterocycle, $SO_2$—N(($CH_2)_n$-aryl)$_2$, $SO_2$—N(($CH_2)_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—$(C_1$-$C_6)$-alkyl, $(C_1$-$C_6)$-alkyl, $NH_2$;

C(NH)($NH_2$), $NH_2$, NH—$(C_1$-$C_6)$-alkyl, N(($C_1$-$C_6)$-alkyl)$_2$, NH($C_1$-$C_7)$-acyl, NH—CO—$(C_1$-$C_6)$-alkyl, NH—COO—$(C_1$-$C_6)$-alkyl, NH—CO-aryl, NH—CO-heterocycle, NH—COO-aryl, NH—COO-heterocycle, NH—CO—NH—$(C_1$-$C_6)$-alkyl, NH—CO—NH-aryl, NH—CO—NH-heterocycle, N$(C_1$-$C_6)$-alkyl —CO—$(C_1$-$C_6)$-alkyl, N$(C_1$-$C_6)$-alkyl —COO—$(C_1$-$C_6)$-alkyl, N$(C_1$-$C_6)$-alkyl —CO-aryl, N$(C_1$-$C_6)$-alkyl —CO-heterocycle, N$(C_1$-$C_6)$-alkyl —COO-aryl, N$(C_1$-$C_6)$-alkyl —COO-heterocycle, N$(C_1$-$C_6)$-alkyl —CO—NH—$(C_1$-$C_6)$-alkyl), N$(C_1$-$C_6)$-alkyl —CO—NH-aryl, N$(C_1$-$C_6)$-alkyl —CO—NH-heterocycle, N(($C_1$-$C_6)$-alkyl)-CO—N—$(C_1$-$C_6)$-alkyl)$_2$, N(($C_1$-$C_6)$-alkyl)-CO—N(($C_1$-$C_6)$-alkyl)-aryl, N(($C_1$-$C_6)$-alkyl)-CO—N(($C_1$-$C_6)$-alkyl)-heterocycle, N(($C_1$-$C_6)$-alkyl)-CO—N-(aryl)$_2$, N(($C_1$-$C_6)$-alkyl)-CO—N-(heterocycle)$_2$, N(aryl)-CO—$(C_1$-$C_6)$-alkyl, N(heterocycle)-CO—$(C_1$-$C_6)$-alkyl, N(aryl)-COO—$(C_1$-$C_6)$-alkyl, N(heterocycle)-COO—$(C_1$-$C_6)$-alkyl, N(aryl)-CO-aryl, N(heterocycle)-CO-aryl, N(aryl)-COO-aryl, N(heterocycle)-COO-aryl, N(aryl)-CO—NH—$(C_1$-$C_6)$-alkyl), N(heterocycle)-CO—NH—$(C_1$-$C_6)$-alkyl), N(aryl)-CO—NH-aryl, N(heterocycle)-CO—NH-aryl, N(aryl)-CO—N—$(C_1$-$C_6)$-alkyl)$_2$, N(heterocycle)-CO—N—$(C_1$-$C_6)$-alkyl)$_2$, N(aryl)-CO—N(($C_1$-$C_6)$-alkyl)-aryl, N(heterocycle)-CO—N(($C_1$-$C_6)$-alkyl)-aryl, N(aryl)-CO—N-(aryl)$_2$, N(heterocycle)-CO—N-(aryl)$_2$, aryl, O—$(CH_2)_n$-aryl, O—$(CH_2)_n$-heterocycle, where n may be 0-6, where the aryl radical or heterocyclic radical may be substituted one to 3 times by F, Cl, Br, I, OH, $CF_3$, $NO_2$, CN, $OCF_3$, O—$(C_1$-$C_6)$-alkyl, $(C_1$-$C_6)$-alkyl, $NH_2$, NH$(C_1$-$C_6)$-alkyl, N(($C_1$-$C_6)$-alkyl)$_2$, $SO_2$—$CH_3$, COOH, COO—$(C_1$-$C_6)$-alkyl, $CONH_2$.

An alkenyl radical means a straight-chain or branched hydrocarbon chain having two or more carbons and one or more double bonds, such as, for example, vinyl, allyl, pentenyl.

The alkenyl radicals may be substituted one or more times by suitable groups such as, for example: F, Cl, Br, I, $CF_3$, $NO_2$, $N_3$, CN, COOH, COO$(C_1$-$C_6)$alkyl, $CONH_2$, CONH ($C_1$-$C_6$)alkyl, CON[($C_1$-$C_6$)alkyl]$_2$, cycloalkyl, ($C_1$-$C_{10}$)-alkyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$;

C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

An alkynyl radical means a straight-chain or branched hydrocarbon chain having two or more carbons and one or more triple bonds, such as, for example, ethynyl, propynyl, hexynyl.

The alkynyl radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkenyl, ($C_1$-$C_6$)-alkyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$;

C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl An aryl radical means a phenyl, naphthyl-, biphenyl-, tetrahydronaphthyl-, alpha- or beta-tetralon-, indanyl- or indan-1-on-yl radical.

The aryl radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle;

—COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

A cycloalkyl radical means a ring system which comprises one or more rings, which is in saturated or partially unsaturated (with one or two double bonds) form and which is composed exclusively of carbon atoms, such as, for example, cyclopropyl, cyclopentyl, cyclopentenyl, cyclohexyl or adamantyl.

The cycloalkyl radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2$NH($C_1$-$C_6$)-alkyl, $SO_2$N[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$;

C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

Heterocycle or heterocyclic radical means rings and ring systems which, apart from carbon, also comprise heteroatoms such as, for example, nitrogen, oxygen or sulfur. Also included in this definition are ring systems in which the heterocycle or the heterocyclic radical is fused to benzene nuclei.

Suitable "heterocycles" or "heterocyclic radicals" are acridinyl, azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl stands both for 2-, 3- and 4-pyridyl. Thienyl stands both for 2- and 3-thienyl. Furyl stands both for 2- and 3-furyl.

Also included are the corresponding N-oxides of these compounds, that is to say, for example, 1-oxy-2-, 3- or 4-pyridyl.

Also included are derivatives of these heterocycles which are benzo-fused one or more times.

The heterocycles or heterocyclic radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2$NH($C_1$-$C_6$)-alkyl, $SO_2$N[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl radical or heterocyclic radical may be substituted up to twice by F, Cl, Br, OH, CF$_3$, NO$_2$, CN, OCF$_3$, O—(C$_1$-C$_6$)-alkyl, (C$_1$-C$_6$)-alkyl, NH$_2$;

C(NH)(NH$_2$), NH$_2$, NH—(C$_1$-C$_6$)-alkyl, N((C$_1$-C$_6$)-alkyl)$_2$, NH(C$_1$-C$_7$)-acyl, NH—CO—(C$_1$-C$_6$)-alkyl, NH—COO—(C$_1$-C$_6$)-alkyl, NH—CO-aryl, NH—CO-heterocycle, NH—COO-aryl, NH—COO-heterocycle, NH—CO—NH—(C$_1$-C$_6$)-alkyl, NH—CO—NH-aryl, NH—CO—NH-heterocycle, N(C$_1$-C$_6$)-alkyl —CO—(C$_1$-C$_6$)-alkyl, N(C$_1$-C$_6$)-alkyl —COO—(C$_1$-C$_6$)-alkyl, N(C$_1$-C$_6$)-alkyl —CO-aryl, N(C$_1$-C$_6$)-alkyl —CO-heterocycle, N(C$_1$-C$_6$)-alkyl —COO-aryl, N(C$_1$-C$_6$)-alkyl —COO-heterocycle, N(C$_1$-C$_6$)-alkyl —CO—NH—(C$_1$-C$_6$)-alkyl), N(C$_1$-C$_6$)-alkyl —CO—NH-aryl, N(C$_1$-C$_6$)-alkyl —CO—NH-heterocycle, N((C$_1$-C$_6$)-alkyl)-CO—N—(C$_1$-C$_6$)-alkyl)$_2$, N((C$_1$-C$_6$)-alkyl)-CO—N((C$_1$-C$_6$)-alkyl)-aryl, N((C$_1$-C$_6$)-alkyl)-CO—N((C$_1$-C$_6$)-alkyl)-heterocycle, N((C$_1$-C$_6$)-alkyl)-CO—N-(aryl)$_2$, N((C$_1$-C$_6$)-alkyl)-CO—N-(heterocycle)$_2$, N(aryl)-CO—(C$_1$-C$_6$)-alkyl, N(heterocycle)-CO—(C$_1$-C$_6$)-alkyl, N(aryl)-COO—(C$_1$-C$_6$)-alkyl, N(heterocycle)-COO—(C$_1$-C$_6$)-alkyl, N(aryl)-CO-aryl, N(heterocycle)-CO-aryl, N(aryl)-COO-aryl, N(heterocycle)-COO-aryl, N(aryl)-CO—NH—(C$_1$-C$_6$)-alkyl), N(heterocycle)-CO—NH—(C$_1$-C$_6$)-alkyl), N(aryl)-CO—NH-aryl, N(heterocycle)-CO—NH-aryl, N(aryl)-CO—N—(C$_1$-C$_6$)-alkyl)$_2$, N(heterocycle)-CO—N—(C$_1$-C$_6$)-alkyl)$_2$, N(aryl)-CO—N((C$_1$-C$_6$)-alkyl)-aryl, N(heterocycle)-CO—N((C$_1$-C$_6$)-alkyl)-aryl, N(aryl)-CO—N-(aryl)$_2$, N(heterocycle)-CO—N-(aryl)$_2$, aryl, O—(CH$_2$)$_n$-aryl, O—(CH$_2$)$_n$-heterocycle, where n may be 0-6, where the aryl radical or heterocyclic radical may be substituted one to 3 times by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl, CONH$_2$.

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of bodyweight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, capsules or tablets, may contain, for example, from 1.0 to 1000 mg, typically from 10 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compound(s) of the formula I may be administered alone or else in combination with further active ingredients. Further active ingredients suitable for combination products are:

all antidiabetics mentioned in the Rote Liste 2004, chapter 12. They may be combined with the compounds of the formula I of the invention in particular for a synergistic improvement of the effect. Administration of the active ingredient combination may take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001.

Antidiabetics include insulin and insulin derivatives such as, for example, Lantus® (see www.lantus.com) or Apidra®, fast-acting insulins (see U.S. Pat. No. 6,221,633), GLP-1 derivatives such as, for example, those disclosed in WO 98/08871 by Novo Nordisk A/S and orally effective hypoglycemic active ingredients.

The orally effective hypoglycemic active ingredients include, preferably, sulfonylureas, biguanidines, meglitinides, oxadiazolidinediones, thiazolidinediones, glucosidase inhibitors, glucagon antagonists, GLP-1 agonists, potassium channel openers such as, for example, those disclosed in WO 97/26265 and WO 99/03861 of Novo Nordisk A/S, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells (PPAR=peroxisome proliferator activated receptor, PXR=pregnane X receptor, ATP=adenosine triphosphate).

In one embodiment of the invention, the compounds of the formula I are administered in combination with an HMGCoA reductase inhibitor such as simvastatin, fluvastatin, pravastatin, lovastatin, atorvastatin, cerivastatin, rosuvastatin (HMG-CoA=3-hydroxy-3-methylglutaryl coenzyme A).

In one embodiment of the invention, the compounds of the formula I are administered in combination with a cholesterol absorption inhibitor such as, for example, ezetimibe, tiqueside, pamaqueside or with a compound as described in PCT/EP 2004/00269, WO 2004/000804, WO 2004/000803, WO 2004/000805, EP 0114531, U.S. Pat. No. 6,498,156.

In one embodiment of the invention, the compounds of the formula I are administered in combination with a PPAR gamma agonist, such as, for example, rosiglitazone, pioglitazone, JTT-501, GI 262570.

In one embodiment of the invention, the compounds of the formula I are administered in combination with a PPAR alpha agonist, such as, for example, GW 9578, GW 7647.

In one embodiment of the invention, the compounds of the formula I are administered in combination with a mixed PPAR alpha/gamma agonist, such as, for example, GW 1536, AVE 8042, AVE 8134, AVE 0847, or as described in WO 00/64888, WO 00/64876, DE10142734.4.

In one embodiment of the invention, the compounds of the formula I are administered in combination with a fibrate such as, for example, fenofibrate, clofibrate, bezafibrate.

In one embodiment of the invention, the compounds of the formula I are administered in combination with an MTP inhibitor such as, for example, implitapide, BMS-201038, R-103757 (MTP=microsomal triglyceride transfer protein).

In one embodiment of the invention, the compounds of the formula I are administered in combination with bile acid absorption inhibitor (see, for example, U.S. Pat. No. 6,245,744 or U.S. Pat. No. 6,221,897), such as, for example, HMR 1741.

In one embodiment of the invention, the compounds of the formula I are administered in combination with a CETP inhibitor, such as, for example, JTT-705 (CETP=cholesteryl ester transfer protein).

In one embodiment of the invention, the compounds of the formula I are administered in combination with a polymeric bile acid adsorbent such as, for example, cholestyramine, colesevelam.

In one embodiment of the invention, the compounds of the formula I are administered in combination with an LDL receptor inducer (see U.S. Pat. No. 6,342,512), such as, for example, HMR1171, HMR1586 (LDL=low density lipids).

In one embodiment of the invention, the compounds of the formula I are administered in combination with an ACAT inhibitor, such as, for example, avasimibe (ACAT=acyl-coenzyme A:cholesterol acyltransferase).

In one embodiment of the invention, the compounds of the formula I are administered in combination with an antioxidant, such as, for example, OPC-14117.

In one embodiment of the invention, the compounds of the formula I are administered in combination with a lipoprotein lipase inhibitor, such as, for example, NO-1886.

In one embodiment of the invention, the compounds of the formula I are administered in combination with an ATP-citrate lyase inhibitor, such as, for example, SB-204990.

In one embodiment of the invention, the compounds of the formula I are administered in combination with a squalene synthetase inhibitor, such as, for example, BMS-188494.

In one embodiment of the invention, the compounds of the formula I are administered in combination with a lipoprotein (a) antagonist, such as, for example, CI-1027 or nicotinic acid.

In one embodiment of the invention, the compounds of the formula I are administered in combination with a lipase inhibitor, such as, for example, orlistat.

In one embodiment of the invention, the compounds of the formula I are administered in combination with insulin.

In one embodiment, the compounds of the formula I are administered in combination with a sulfonylurea such as, for example, tolbutamide, glibenclamide, glipizide or glimepiride.

In one embodiment, the compounds of the formula I are administered in combination with a biguanide, such as, for example, metformin.

In one further embodiment, the compounds of the formula I are administered in combination with a meglitinide, such as, for example, repaglinide.

In one embodiment, the compounds of the formula I are administered in combination with a thiazolidinedione, such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compounds of the formula I are administered in combination with an α-glucosidase inhibitor, such as, for example, miglitol or acarbose.

In one embodiment, the compounds of the formula I are administered in combination with an adenosine A1 agonist such as, for example, those described in WO 2004/003002.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with more than one of the aforementioned compounds, e.g. in combination with a sulfonylurea and metformin, with a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33 (9), 554-558), NPY antagonists (NPY=Neuropeptid Y, e.g. naphthalene-1-sulfonic acid {4-[(4-aminoquinazolin-2-ylamino)methyl]-cyclohexylmethyl}amide hydrochloride (CGP 71683A)), MC4 agonists (MC4=melanocortin 4 receptor, e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (H3=histamine receptor, e.g. (3-cyclohexyl-1-(4,4-dimethyl-1,4,6,7-tetrahydroimidazo[4,5-c]pyridin-5-yl)propan-1-one oxalic acid salt (WO 00/63208)); TNF agonists (TNF=tumor necrosis factor), CRF antagonists (CRF=corticotrophin releasing factor, e.g. [2-methyl-9-(2,4,6-trimethylphenyl)-9H-1,3,9-triazafluoren-4-yl]-dipropylamine (WO 00/66585)), CRF BP antagonists (CRF-BP=corticotrophin releasing factor-binding protein, e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]ethanol hydrochloride (WO 01/83451)), CB1 (cannabinoid receptor 1) receptor antagonists (e.g. rimonabant or the active ingredients mentioned in WO 02/28346), MSH (melanocyte-stimulating hormone) agonists, CCK-A (CCK-A=cholecystokinin-A) agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists (serotonin mimetics) e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (TRH=TSH releasing hormone; TSH=thyroid-stimulating hormone; thyrotropin), see, for example, EP 0 462 884 uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (DA=dopamine autoreceptor, e.g. bromocriptine, Doprexin), lipase/amylase inhibitors (e.g. WO 00/40569), PPAR modulators (e.g. WO 00/78312), RXR (RXR=retinoid X receptor) modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2 (10), 1615-1622.

In one embodiment, the other active ingredient is dexamphetamine or amphetamine.

In one embodiment, the other active ingredient is fenfluramine or dexfenfluramine.

In another embodiment, the other active ingredient is sibutramine.

In one embodiment, the other active ingredient is orlistat.

In one embodiment, the other active ingredient is mazindol or phentermine.

In one embodiment, the other active ingredient is rimonabant.

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18 (5), 230-6.) Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more other pharmacologically active substances is regarded as falling within the protection conferred by the present invention.

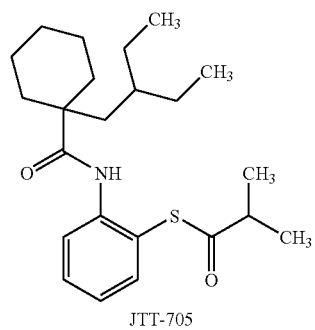

JTT-705

-continued

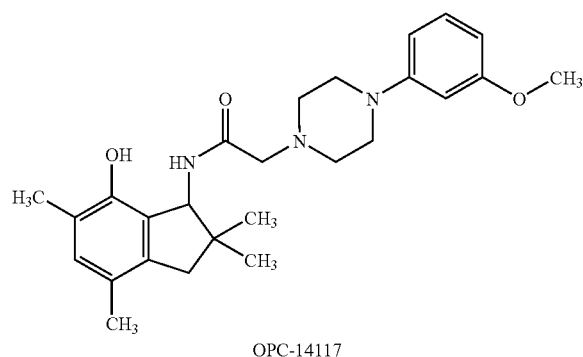
OPC-14117

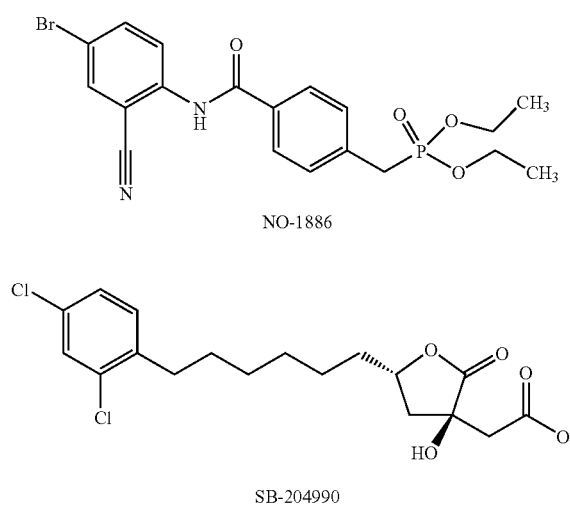
NO-1886

SB-204990

BMS-188494

-continued

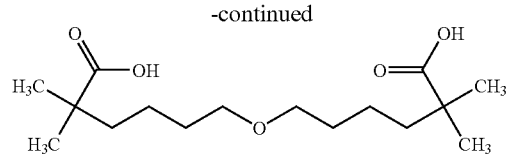
CI-1027

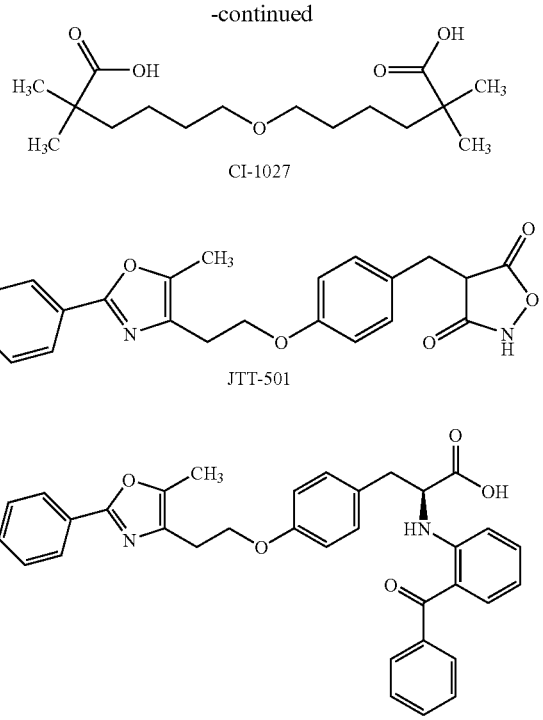
JTT-501

GI 262570

The examples detailed hereinafter serve to illustrate the invention without, however, restricting it.

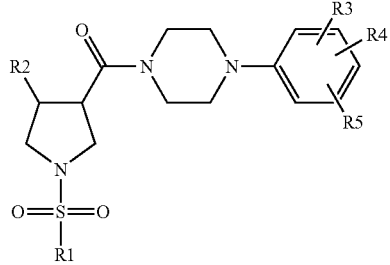

The relative configuration indicates the disposition of the substituents in position 3 and 4 on the pyrrolidine ring, and broken lines indicate the attachment.

| Example | relative configuration | R1 | R2 | R3 | R4 | R5 |
|---|---|---|---|---|---|---|
| 1 | trans | 3,5-dimethylisoxazol-4-yl | p-tolyl | o-CH3 | m'-CH3 | H |

-continued

| Example | relative configuration | R1 | R2 | R3 | R4 | R5 |
|---|---|---|---|---|---|---|
| 2 | trans | 4-biphenyl | phenyl | H | o-CH3 | H |
| 3 | trans | 4-biphenyl | phenyl | H | p-NO2 | H |
| 4 | trans | 2,5-dichlorophenyl | phenyl | H | m-CF3 | H |
| 5 | trans | 2,5-dimethoxyphenyl | phenyl | H | H | H |
| 6 | trans | 2,4,6-triisopropylphenyl | phenyl | H | H | H |
| 7 | trans | 2-thienyl | phenyl | H | p-COCH3 | H |
| 8 | trans | 4-chlorophenyl | phenyl | o-CH3 | m'-CH3 | H |

-continued

| Example | relative configuration | R1 | R2 | R3 | R4 | R5 |
|---------|------------------------|----|----|-----|-----|-----|
| 9 | trans | 4-propylphenyl | phenyl | o-CH3 | m-CH3 | H |
| 10 | trans | 3-chloro-4-fluorophenyl | phenyl | o-CH3 | m'-CH3 | H |
| 11 | trans | quinolin-8-yl | phenyl | H | o-Cl | H |
| 12 | trans | benzyl | phenyl | H | p-Cl | H |
| 13 | trans | styryl | phenyl | H | p-OCH3 | H |
| 14 | trans | 4-(trifluoromethoxy)phenyl | phenyl | H | o-Cl | H |
| 15 | trans | 4-nitrophenyl | phenyl | H | p-Cl | H |

-continued

| Example | relative configuration | R1 | R2 | R3 | R4 | R5 |
|---|---|---|---|---|---|---|
| 16 | trans | 4-tert-butylphenyl | phenyl | H | p-OCH3 | H |
| 17 | trans | 3-(trifluoromethyl)phenyl | phenyl | H | p-OCH3 | H |
| 18 | trans | 1-naphthyl | phenyl | H | o-OCH2CH3 | H |
| 19 | trans | 2,3-dibromothiophen-5-yl | phenyl | H | o-F | H |
| 20 | trans | 5-chlorothiophen-2-yl | phenyl | H | H | H |
| 21 | trans | 4,5-dichlorothiophen-2-yl | phenyl | H | H | H |
| 22 | trans | methyl 4-methylthiophene-2-carboxylate-5-yl | phenyl | H | H | H |
| 23 | trans | 5-chloro-3-methylbenzo[b]thiophen-2-yl | phenyl | H | H | H |
| 24 | trans | thiophen-2-yl | phenyl | H | o-OCH3 | H |

-continued

| Example | relative configuration | R1 | R2 | R3 | R4 | R5 |
|---|---|---|---|---|---|---|
| 25 | trans | 2,3-dibromothiophen-5-yl | phenyl | H | o-OCH3 | H |
| 26 | trans | 5-chlorothiophen-2-yl | phenyl | H | o-OCH3 | H |
| 27 | trans | 2,3-dichlorothiophen-5-yl | phenyl | H | o-OCH3 | H |
| 28 | trans | methyl 4-methyl-5-(thiophene-2-carboxylate)-yl | phenyl | H | o-OCH3 | H |
| 29 | trans | 5-chloro-3-methylbenzo[b]thiophen-2-yl | phenyl | H | o-OCH3 | H |
| 30 | trans | thiophen-2-yl | phenyl | H | m-CF3 | H |
| 31 | trans | 2,3-dibromothiophen-5-yl | phenyl | H | m-CF3 | H |
| 32 | trans | 5-chlorothiophen-2-yl | phenyl | H | m-CF3 | H |
| 33 | trans | 2,3-dichlorothiophen-5-yl | phenyl | H | m-CF3 | H |

-continued

| Example | relative configuration | R1 | R2 | R3 | R4 | R5 |
|---|---|---|---|---|---|---|
| 34 | trans | methyl 4-methylthiophene-2-carboxylate (2,5-subst) | phenyl | H | m-CF3 | H |
| 35 | trans | 5-chloro-3-methylbenzothiophene (2-subst) | phenyl | H | m-CF3 | H |
| 36 | trans | thiophene (2-subst) | phenyl | o-CH3 | p-CH3 | H |
| 37 | trans | 2,3-dibromothiophene (5-subst) | phenyl | o-CH3 | p-CH3 | H |
| 38 | trans | 5-chlorothiophene (2-subst) | phenyl | o-CH3 | p-CH3 | H |
| 39 | trans | 4,5-dichlorothiophene (2-subst) | phenyl | o-CH3 | p-CH3 | H |
| 40 | trans | methyl 4-methylthiophene-2-carboxylate (2,5-subst) | phenyl | o-CH3 | p-CH3 | H |
| 41 | trans | 5-chloro-3-methylbenzothiophene (2-subst) | phenyl | o-CH3 | p-CH3 | H |
| 42 | trans | thiophene (2-subst) | phenyl | m-CH3 | p-CH3 | H |

-continued

| Example | relative configuration | R1 | R2 | R3 | R4 | R5 |
|---|---|---|---|---|---|---|
| 43 | trans | 2,3-dibromothiophen-5-yl | phenyl | m-CH3 | p-CH3 | H |
| 44 | trans | 5-chlorothiophen-2-yl | phenyl | m-CH3 | p-CH3 | H |
| 45 | trans | 2,3-dichlorothiophen-5-yl | phenyl | m-CH3 | p-CH3 | H |
| 46 | trans | methyl 4-methylthiophene-2-carboxylate-5-yl | phenyl | m-CH3 | p-CH3 | H |
| 47 | trans | 5-chloro-3-methylbenzothiophen-2-yl | phenyl | m-CH3 | p-CH3 | H |
| 48 | trans | 5-chlorothiophen-2-yl | phenyl | o-CH3 | m'-CH3 | H |
| 49 | trans | 2,3-dichlorothiophen-5-yl | phenyl | o-CH3 | m'-CH3 | H |
| 50 | trans | methyl 4-methylthiophene-2-carboxylate-5-yl | phenyl | o-CH3 | m'-CH3 | H |
| 51 | trans | 5-chloro-3-methylbenzothiophen-2-yl | phenyl | o-CH3 | m'-CH3 | H |

-continued
| Example | relative configuration | R1 | R2 | R3 | R4 | R5 |
|---|---|---|---|---|---|---|
| 52 | trans | 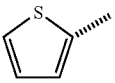 | 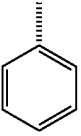 | o-CH3 | m-CH3 | H |
| 53 | trans | 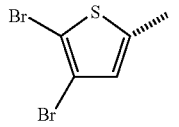 | 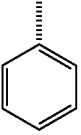 | o-CH3 | m-CH3 | H |
| 54 | trans | 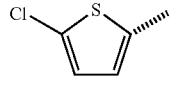 | 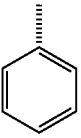 | o-CH3 | m-CH3 | H |
| 55 | trans | 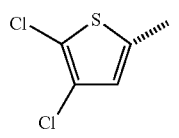 | 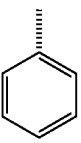 | o-CH3 | m-CH3 | H |
| 56 | trans | 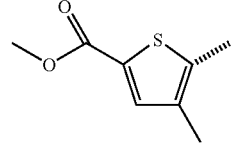 | 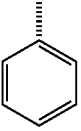 | o-CH3 | m-CH3 | H |
| 57 | trans | 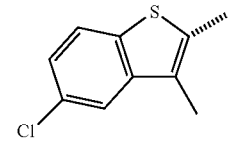 | 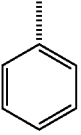 | o-CH3 | m-CH3 | H |
| 58 | trans |  | 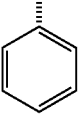 | H | p-OCH3 | H |
| 59 | trans | 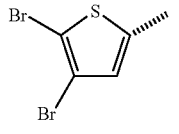 | 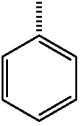 | H | p-OCH3 | H |
| 60 | trans | 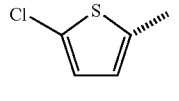 | 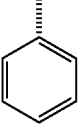 | H | p-OCH3 | H |
| 61 | trans | 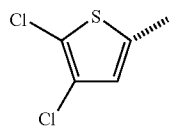 | 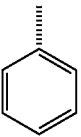 | H | p-OCH3 | H |

-continued

| Example | relative configuration | R1 | R2 | R3 | R4 | R5 |
|---|---|---|---|---|---|---|
| 62 | trans | methyl 4-methyl-thiophene-2-carboxylate (5-yl) | phenyl | H | p-OCH3 | H |
| 63 | trans | 5-chloro-3-methyl-benzothiophen-2-yl | phenyl | H | p-OCH3 | H |
| 64 | trans | 2,3-dibromo-thiophen-5-yl | phenyl | H | H | H |
| 65 | trans | thiophen-2-yl | phenyl | o-CO2Me | m'-CO2Me | H |
| 66 | trans | thiophen-2-yl | phenyl | o-Cl | m'-Cl | H |
| 67 | trans | thiophen-2-yl | phenyl | o-CH3 | m'-CH3 | H |
| 68 | trans | benzo[c][1,2,5]oxadiazol-4-yl | phenyl | o-CH3 | m'-CH3 | H |
| 69 | trans | 3-methoxyphenyl | phenyl | o-CH3 | m'-CH3 | H |
| 70 | trans | isobutyl | phenyl | o-CH3 | m'-CH3 | H |

-continued

| Example | relative configuration | R1 | R2 | R3 | R4 | R5 |
|---|---|---|---|---|---|---|
| 71 | trans | 3,5-dimethylisoxazol-4-yl | phenyl | o-CH3 | m'-CH3 | H |
| 72 | trans | pyridin-3-yl | phenyl | o-CH3 | m'-CH3 | H |
| 73 | trans | pyridin-3-yl | phenyl | o-Cl | m'-Cl | H |
| 74 | trans | 3-methylphenyl | phenyl | o-Cl | m'-Cl | H |
| 75 | trans | 4-methoxyphenyl | phenyl | o-Cl | m'-Cl | H |
| 76 | trans | 1,1,1-trifluoropropan-2-yl | phenyl | o-OCH3 | m'-OCH3 | H |
| 77 | trans | pyridin-3-yl | phenyl | o-OCH3 | m'-OCH3 | H |
| 78 | trans | isopropyl | phenyl | o-OCH3 | m'-OCH3 | H |
| 79 | trans | 4-methoxyphenyl | phenyl | o-OCH3 | m'-OCH3 | H |

-continued

| Example | relative configur- ation | R1 | R2 | R3 | R4 | R5 |
|---|---|---|---|---|---|---|
| 80 | trans | 3-methylphenyl | phenyl | o-OCH3 | m'-OCH3 | H |
| 81 | trans | 3,5-dimethylisoxazol-4-yl | phenyl | o-OCH3 | m'-OCH3 | H |
| 82 | trans | 3-methoxyphenyl | phenyl | o-OCH3 | m'-OCH3 | H |
| 83 | trans | benzofurazan-4-yl | phenyl | o-OCH3 | m'-OCH3 | H |
| 84 | trans | thiophen-2-yl | phenyl | o-OCH3 | m'-OCH3 | H |
| 85 | trans | 2-methylphenyl | phenyl | o-Cl | m'-Cl | H |
| 86 | trans | 3-methoxyphenyl | phenyl | o-CH3 | o'-CH3 | H |
| 87 | trans | 3,5-dimethylisoxazol-4-yl | benzo[1,3]dioxol-5-yl | o-CH3 | m'-CH3 | H |
| 88 | trans | 3-methoxyphenyl | benzo[1,3]dioxol-5-yl | o-CH3 | m'-CH3 | H |

-continued

| Example | relative configuration | R1 | R2 | R3 | R4 | R5 |
|---|---|---|---|---|---|---|
| 89 | trans | pyridin-3-yl | benzo[1,3]dioxol-5-yl | o-CH3 | m'-CH3 | H |
| 90 | trans | 3,5-dimethylisoxazol-4-yl | (unspecified) | o-CH3 | m'-CH3 | H |
| 91 | trans | 3-methoxyphenyl | (unspecified) | o-CH3 | m'-CH3 | H |
| 92 | trans | pyridin-3-yl | (unspecified) | o-CH3 | m'-CH3 | H |
| 93 | trans | 3,5-dimethylisoxazol-4-yl | benzyl | o-CH3 | m'-CH3 | H |
| 94 | trans | 3-methoxyphenyl | benzyl | o-CH3 | m'-CH3 | H |
| 95 | trans | 3,5-dimethylisoxazol-4-yl | isobutyl | o-CH3 | m'-CH3 | H |
| 96 | trans | 3-methoxyphenyl | isobutyl | o-CH3 | m'-CH3 | H |
| 97 | trans | 3,5-dimethylisoxazol-4-yl | tetrahydrofuran-2-yl | o-CH3 | m'-CH3 | H |

-continued
| Example | relative configuration | R1 | R2 | R3 | R4 | R5 |
|---|---|---|---|---|---|---|
| 98 | trans | 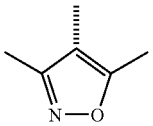 | 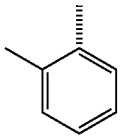 | o-CH3 | m'-CH3 | H |
| 99 | trans | 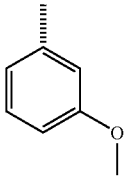 | 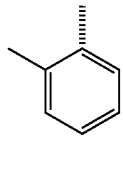 | o-CH3 | m'-CH3 | H |
| 100 | trans | 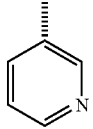 | 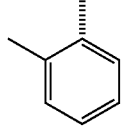 | o-CH3 | m'-CH3 | H |
| 101 | trans | 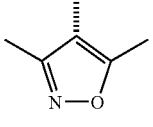 | 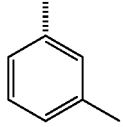 | o-CH3 | m'-CH3 | H |
| 102 | trans | 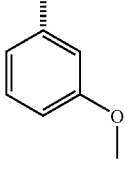 | 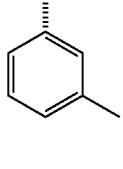 | o-CH3 | m'-CH3 | H |
| 103 | trans | 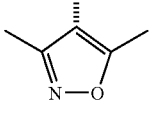 | 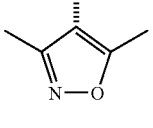 | o-CH3 | m'-CH3 | H |
| 104 | trans | 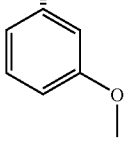 | 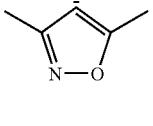 | o-CH3 | m'-CH3 | H |
| 105 | trans | 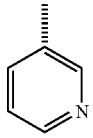 | 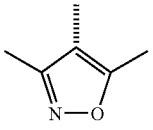 | o-CH3 | m'-CH3 | H |
| 106 | trans | 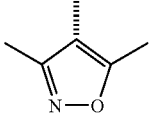 | 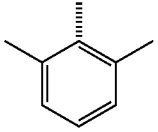 | o-CH3 | m'-CH3 | H |

-continued

| Example | relative configur- ation | R1 | R2 | R3 | R4 | R5 |
|---|---|---|---|---|---|---|
| 107 | trans | 3,5-dimethylisoxazol-4-yl | 4-methyl-3,4-dihydro-2H-benzo[b][1,4]oxazin-7-yl | o-CH3 | m'-CH3 | H |
| 108 | trans | 3,5-dimethylisoxazol-4-yl | benzo[d][1,3]dioxol-4-yl | o-CH3 | m'-CH3 | H |
| 109 | trans | 3-methoxyphenyl | 4-methyl-3,4-dihydro-2H-benzo[b][1,4]oxazin-7-yl | o-CH3 | m'-CH3 | H |
| 110 | trans | 3-methoxyphenyl | thiophen-2-yl | o-CH3 | m'-CH3 | H |
| 111 | trans | 3,5-dimethylisoxazol-4-yl | thiophen-2-yl | o-CH3 | m'-CH3 | H |
| 112 | trans | 3,5-dimethylisoxazol-4-yl | pyridin-3-yl | o-CH3 | m'-CH3 | H |
| 113 | trans | pyridin-3-yl | pyridin-3-yl | o-CH3 | m'-CH3 | H |
| 114 | trans | 3-methoxyphenyl | furan-2-yl | o-CH3 | m'-CH3 | H |
| 115 | trans | 3,5-dimethylisoxazol-4-yl | furan-2-yl | o-CH3 | m'-CH3 | H |

-continued

| Example | relative configuration | R1 | R2 | R3 | R4 | R5 |
|---|---|---|---|---|---|---|
| 116 | trans | 3-pyridyl | 2-furyl | o-CH3 | m'-CH3 | H |
| 117 | cis | 2-thienyl | phenyl | o-CH3 | m'-CH3 | H |
| 118 | cis | 3,5-dimethylisoxazol-4-yl | phenyl | o-CH3 | m'-CH3 | H |
| 119 | cis | 3-methoxyphenyl | phenyl | o-CH3 | m'-CH3 | H |
| 120 | cis | 3-pyridyl | phenyl | o-CH3 | m'-CH3 | H |

The activity of the compounds was tested as follows:

ABCA-1 is a membrane-bound transporter protein which has a key role in the efflux of cholesterol from extrahepatic cells to nascent HDL particles (Singaraja et al, Arterioscler Thromb Vasc Biol., 1322-1332, 2003). HDL particles are taken up by the liver via the SRB1 receptor. Transport of cholesterol from peripheral tissues back to the liver, in which ABCA1 is crucially involved, is referred to as reverse cholesterol transport.

Numerous genetic mutations of the ABCA-1 gene are known. Thus, the genetic disease "Tangier's disease" has its molecular origin in mutations of ABCA1. These are expressed in the homozygous form of the disease by a very low HDL cholesterol level and a greatly increased risk of cardiovascular disorders. (Brooks-Wilson et al., Nat. Genet. 22, 336-345, 1999; Bodzioch et al., Nat. Genet., 22, 347-351, 1999; Rust et al., Nat. Genet., 22, 352-355, 1999).

In analogy to the situation in humans, homozygous ABCA-1 knockout mice have virtually no measurable HDL plasma levels, whereas heterozygous ABCA-1 knockout mice have an HDL level which is reduced by about 50% (Orso et al. Nat. Genet. 24, 192-196, 2000; McNeish et al., Proc. Natl. Acad. Sci. USA, 97, 4245-4250, 2000). ABCA-1 knockout mice additionally exhibit increased cholesterol absorption (McNeish et al., Proc. Natl. Acad. Sci. USA, 97, 4245-4250, 2000).

An increase in ABCA-1 gene expression potentially leads to an increase in HDL cholesterol, a decrease in intestinal cholesterol absorption and to an increased excretion of excess cholesterol from extrahepatic tissue, including macrophages. It has further been shown that overexpression of ABCA1 in atherosclerotic mouse models leads to a significant reduction in atherosclerosis (Brewer et al., Am J Cardiol, 10K-16K, 2003; Singaraja et al., J Clin Invest, 110, 35-42, 2002).

ABCA1 Promoter Test

Principle

The potency of substances which activate expression of the human ABCA1 gene via its promoter is analyzed by using a stably transfected THP1 cell line (human monocyte cell line) which is referred to herein as ABCA1 reporter cell line. It contains a fragment, 3.2 kb in size and stably integrated into the genome, of the human ABCA1 promoter in front of a luciferase reporter element. Expression of the luciferase reporter gene is only low without addition of an ABCA1 expression activator. The substances stimulating ABCA1 expression bring about, via activation of the ABCA1 promoter, an enhanced expression of the luciferase reporter gene. The luciferase which is formed can be detected via an appropriate substrate by means of chemiluminescence.

Construction of the Cell Line

The ABCA1 reporter line was prepared as follows: firstly the neomycin resistance gene (Acc. No.: AJ000156) was introduced into the luciferase reporter plasmid pLG3basic (#1751, Promega) 3' below the luciferase reporter element. Subsequently, an ABCA1 promoter fragment, 3.2 kb in size and amplified from human genomic DNA (#6550-1, Clontech) by the polymerase chain reaction, was cloned in 5' above the luciferase reporter element. The reporter plasmid produced in this way was called pGL3BN-ABCA1P. Luciferase expression in this plasmid is controlled by the ABCA1 promoter. Cloning and sequencing of the construct took place in analogy to the description in Sambrook J et al. (Molecular cloning, Cold Spring Harbor Laboratory Press, 1989). For stable transfection into THP1 cells, firstly pGL3BN-ABCA1P was linearized with a restriction endonuclease and then introduced into the THP1 cells as stated in Ausubel, F. M. et al. (Current protocols in molecular biology, Vol. 1-3, John Wiley & Sons, Inc., 1995). Geneticin-containing medium (0.5 mg/ml) was used to select a suitable stable cell clone which showed maximal activation of the luciferase gene after treatment with a standard ABCA1 expression activator.

Test Procedure

The activity of ABCA1 expression activators is determined in a 3-day test which is described below:

Day 1

The ABCA1 reporter cell line comprises suspension cells. These are cultured until the concentration is $0.5 \times 10^6$ cells/ml in RPMI medium (#52400-025, Invitrogen) which is mixed with the following additions: 10% FCS (fetal calf serum; #16000-044, invitrogen), 0.5 mg/ml Geneticin (#10131-019, invitrogen) and 1% penicillin-streptomycin solution (#15140-122, invitrogen). The culturing takes place in standard cell culture flasks (#353112, Becton Dickinson) in a cell culture incubator at 37° C. in the presence of 5% $CO_2$.

For the ABCA1 promoter test, the suspension cells are centrifuged at 1200 rpm in 50 ml tubes. The supernatant is aspirated off, and the pellet is resuspended in 15 ml of RPMI medium and counted in a cell counter. After dilution to 175 000 cells/ml, 0.1 µg/ml PMA (phorbol 12-myristate 13-acetate, #8139-5MG, Sigma) is added in order to induce differentiation of the monocytic THP1 suspension cells into adherent macrophages. 35 000 cells in each well are seeded in a 96-well microtiter plate with clear plastic base (#3610, Corning Costar). The plates are incubated in a cell culture incubator at 37° C. and 5% CO2 for 24 h.

Day 2

The ABCA1 expression activators to be tested are dissolved in a concentration of 10 mM in DMSO. This stock solution is diluted in the RPMI medium (mixed with 0.1 µg/ml PMA) described above. Test substances are tested in 11 different concentrations in the range from 33 µm to 330 pM. The medium of the ABCA1 reporter cell line seeded on day 1 is completely removed by aspiration and the diluted test substances are immediately added to the cells. The dilution and addition of the substances takes place with a pipetting robot (Beckman FX). The final volume of the test substances diluted in medium is 100 µl per well of a 96-well microtiter plate. The DMSO concentration in the test is less than 0.1% v/v in order to avoid cytotoxic effects of the solvent.

Each plate was charged with a standard ABCA1 expression activator, which is likewise diluted in 11 different concentrations, in order to demonstrate the ability of the test to function in each individual plate. The test plates are incubated in an incubator at 37° C. and 5% $CO_2$ for 24 h.

Day 3

The ABCA1 reporter cells treated with the test substances are removed from the incubator and the medium is aspirated off. The cells are lyzed by pipetting 50 µl of Bright Glo reagent (#E2650, Promega) into each well of a 96-well microtiter plate. After incubation in the dark at room temperature for 10 minutes, the microtiter plates are measured in a luminometer (Trilux from Wallac). The measurement time per well of a microtiter plate is 1 sec.

Evaluation

The raw data from the luminometer are transferred into a Microsoft Excel file. Dose-response plots and EC50 values of ABCA1 expression activators are calculated using the XL.Fit program as specified by the manufacturer (IDBS).

TABLE 2

Biological activity

| Example No. | E50 ABCA1 [µM] |
| --- | --- |
| 1 | 2.83705 |
| 7 | 13.18232 |
| 21 | 4.62253 |
| 24 | 14.98243 |
| 25 | 3.81272 |
| 26 | 2.93693 |
| 27 | 6.99135 |
| 29 | 5.60744 |
| 30 | 3.21622 |
| 31 | 1.77475 |
| 32 | 16.16255 |
| 33 | 6.5901 |
| 36 | 3.60377 |
| 37 | 2.56764 |
| 38 | 2.65662 |
| 39 | 3.72624 |
| 42 | 18.81371 |
| 43 | 4.07876 |
| 44 | 15.14785 |
| 45 | 4.61792 |
| 48 | 0.7057 |
| 49 | 1.9526 |
| 50 | 7.34391 |
| 51 | 2.76602 |
| 52 | 3.27045 |
| 53 | 5.75795 |
| 54 | 4.63021 |
| 55 | 0.82611 |
| 59 | 1.15728 |
| 60 | 6.67634 |
| 61 | 2.6119 |
| 64 | 3.15637 |
| 66 | 0.43197 |
| 67 | 2.19183 |
| 68 | 0.86925 |
| 69 | 0.33012 |
| 70 | 0.91525 |
| 71 | 0.38061 |
| 72 | 0.24141 |
| 73 | 0.40652 |
| 74 | 0.34049 |
| 75 | 0.97963 |
| 76 | 3.11583 |
| 79 | 1.5805 |
| 80 | 3.1521 |
| 81 | 1.81796 |
| 82 | 1.49147 |
| 83 | 3.00327 |
| 84 | 2.66994 |
| 85 | 0.25968 |
| 86 | 0.45878 |
| 87 | 1.22638 |
| 88 | 2.71771 |
| 90 | 16.76062 |
| 91 | 2.34185 |
| 93 | 2.47707 |
| 94 | 2.92544 |
| 95 | 4.59268 |
| 96 | 3.604 |

TABLE 2-continued

| Example No. | Biological activity E50 ABCA1 [μM] |
|---|---|
| 98 | 0.40095 |
| 99 | 0.70676 |
| 100 | 1.34805 |
| 101 | 1.85365 |
| 102 | 1.04924 |
| 104 | 6.27323 |
| 106 | 0.37205 |
| 108 | 0.58486 |
| 110 | 0.9142 |
| 111 | 0.86686 |
| 112 | 14.29582 |
| 114 | 2.13601 |
| 115 | 2.63737 |
| 116 | 10.82924 |
| 117 | 0.29118 |
| 118 | 0.34646 |
| 119 | 0.17737 |
| 120 | 0.39477 |

It is evident from the table that the compounds of the formula I increase ABCA-1 gene expression and thus bring about an increase in HDL cholesterol.

Methods

The compounds of the formula I of the invention can be prepared in accordance with the following reaction schemes:

Method A:

This method is used to synthesize building block B, where R3, R4 and R5 have the abovementioned meanings.

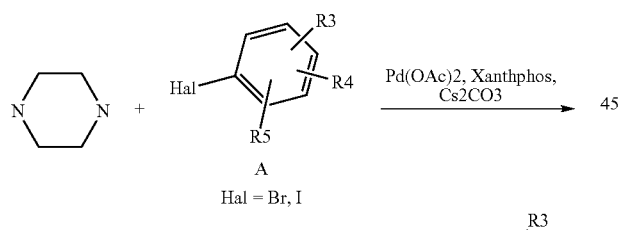

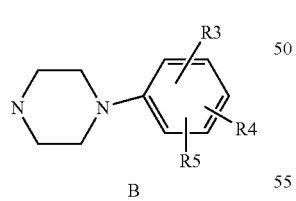

An aromatic or heteroaromatic halide of the general formula A, where R3, R4 and R5 have the abovementioned meanings, is reacted with piperazine with palladium catalysis in the presence of a base such as, for example, cesium carbonate and of a ligand such as, for example, 9,9-dimethyl-4,5-bis(diphenylphosphino)xanthene and a palladium source such as, for example, palladium acetate in a solvent such as, for example, 1,4-dioxane to give the substituted piperazine of the general formula B.

Method B:

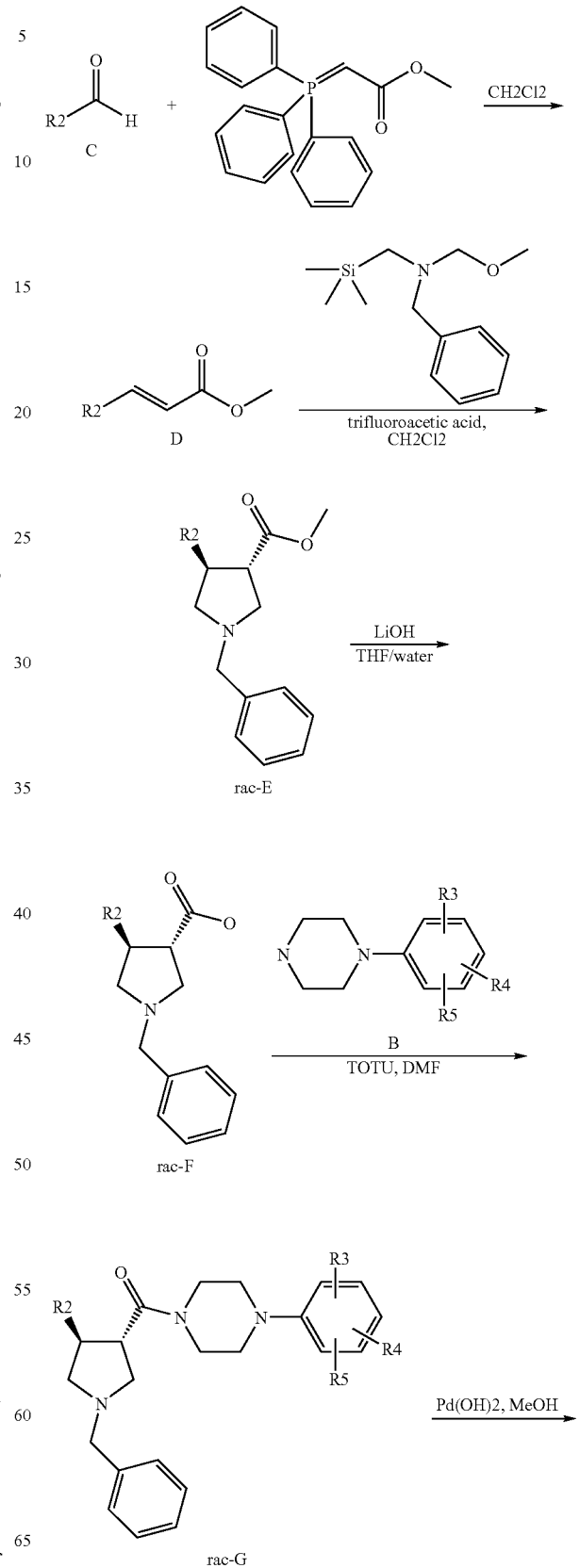

-continued

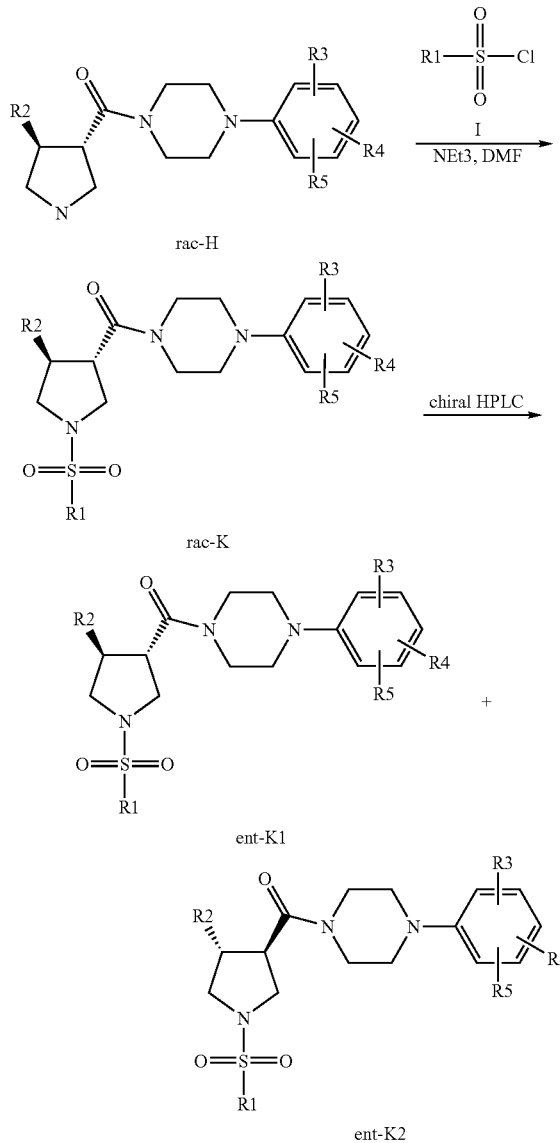

have the meanings described above, to give the amide of the general formula G. The action of hydrogen in the presence of a catalyst such as, for example, palladium hydroxide in a polar solvent such as methanol or, if R2 comprises a substituent which is sensitive to hydrogenolysis, by reaction with 2,2,2-trichloroethoxycarbonyl chloride in a solvent such as, for example, acetonitrile and subsequent cleavage of the resulting carbamate by using zinc in acetic acid on the benzyl-protected pyrrolidine of the general formula G results in the unprotected pyrrolidine of the general formula H. Reaction with a sulfonyl chloride of the general formula I, in which R1 has the meaning described above, results in the sulfonylpyrrolidine of the general formula K. If K is purified by RP-HPLC with acetonitrile/water+0.1% trifluoroacetic acid as eluent, the result is the trifluoroacetate salt of K. The racemic mixture can be separated by chiral HPLC into the enantiopure forms of the general formulae K1 and K2.

Examples 1 to 110 were synthesized by this method.

Method C:

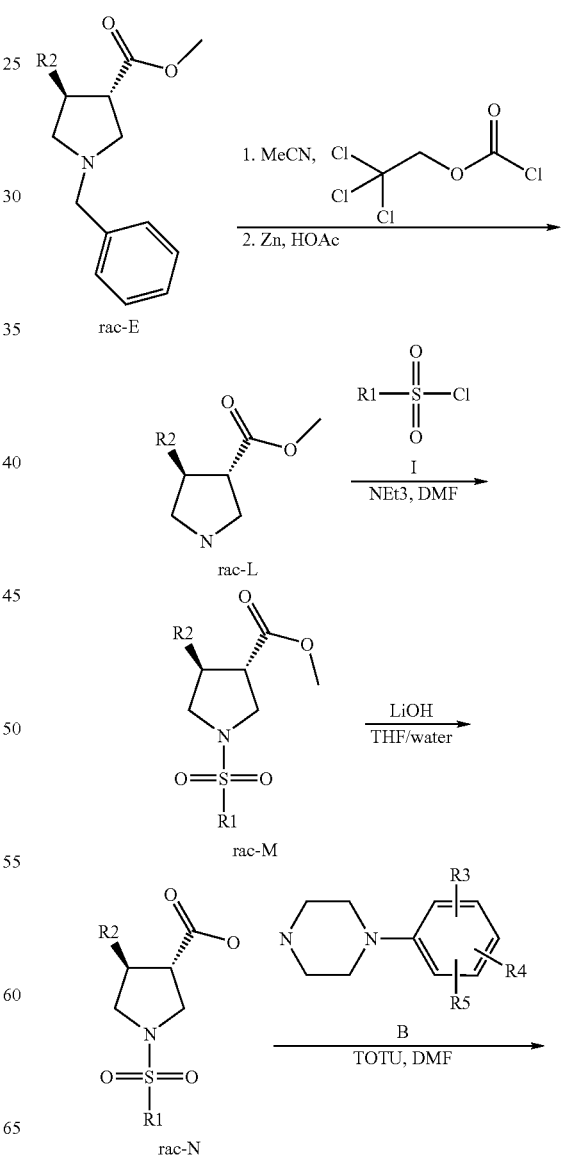

An aldehyde of the general formula C, in which R2 has the meaning described above, is reacted with methyl (triphenylphosphorane ylide) acetate in a nonpolar aprotic solvent such as, for example, dichloromethane to give the α,β-unsaturated ester with the trans configuration of the general formula D. The ester is reacted with N-(methoxymethyl)-N-(trimethylsilylmethyl)benzylamine in a nonpolar aprotic solvent such as, for example, dichloromethane in the presence of an acid such as, for example, trifluoroacetic acid to give the methylpyrrolidine-3-carboxylate with the trans configuration of the general formula E. The ester is cleaved with a base such as lithium hydroxide in a polar solvent mixture such as tetrahydrofuran and water to give the free carboxylic acid of the general formula F. With the action of a coupling reagent such as, for example, O-[cyano(ethoxycarbonyl)methyleneamino]-1,1,3,3-tetramethyluronium tetrafluoroboate in the presence of a base such as, for example, triethylamine in a polar aprotic solvent such as N,N-dimethylformamide, the carboxylic acid of the general formula F is reacted with the piperazine of the general formula B, in which R3, R4 and R5

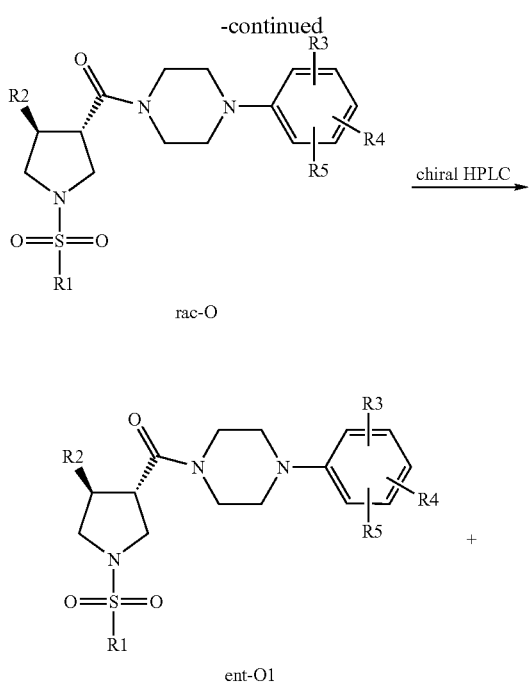

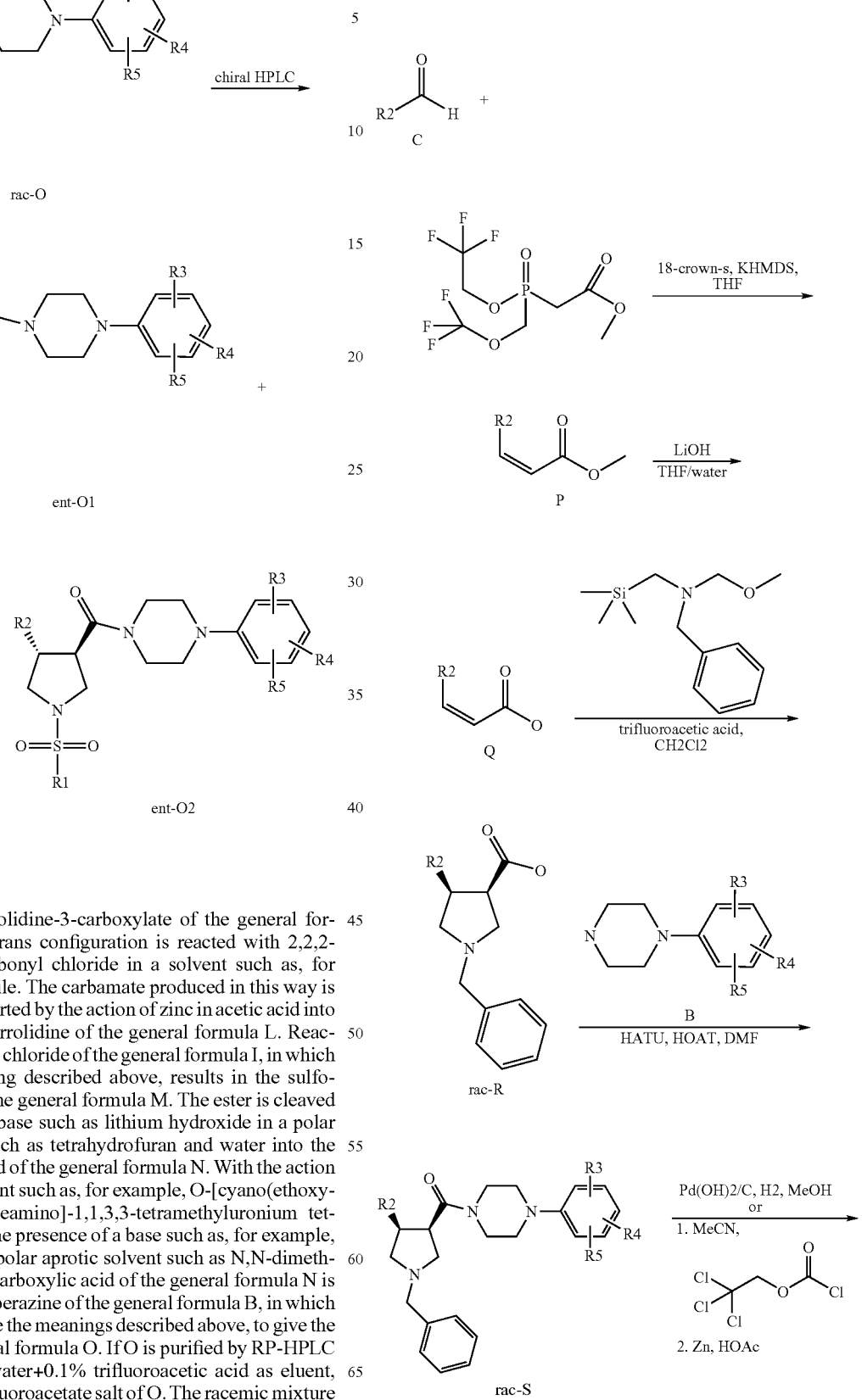

of the general formulae O1 and O2. Examples 110 to 117 were synthesized by this method.

Method D:

The methylpyrrolidine-3-carboxylate of the general formula E with the trans configuration is reacted with 2,2,2-trichloroethoxycarbonyl chloride in a solvent such as, for example, acetonitrile. The carbamate produced in this way is immediately converted by the action of zinc in acetic acid into the unprotected pyrrolidine of the general formula L. Reaction with a sulfonyl chloride of the general formula I, in which R1 has the meaning described above, results in the sulfonylpyrrolidine of the general formula M. The ester is cleaved by the action of a base such as lithium hydroxide in a polar solvent mixture such as tetrahydrofuran and water into the free carboxylic acid of the general formula N. With the action of a coupling reagent such as, for example, O-[cyano(ethoxycarbonyl)methyleneamino]-1,1,3,3-tetramethyluronium tetrafluoroborate in the presence of a base such as, for example, triethylamine in a polar aprotic solvent such as N,N-dimethylformamide, the carboxylic acid of the general formula N is reacted with the piperazine of the general formula B, in which R3, R4 and R5 have the meanings described above, to give the amide of the general formula O. If O is purified by RP-HPLC with acetonitrile/water+0.1% trifluoroacetic acid as eluent, the result is the trifluoroacetate salt of O. The racemic mixture can be separated by chiral HPLC into the enantiopure forms

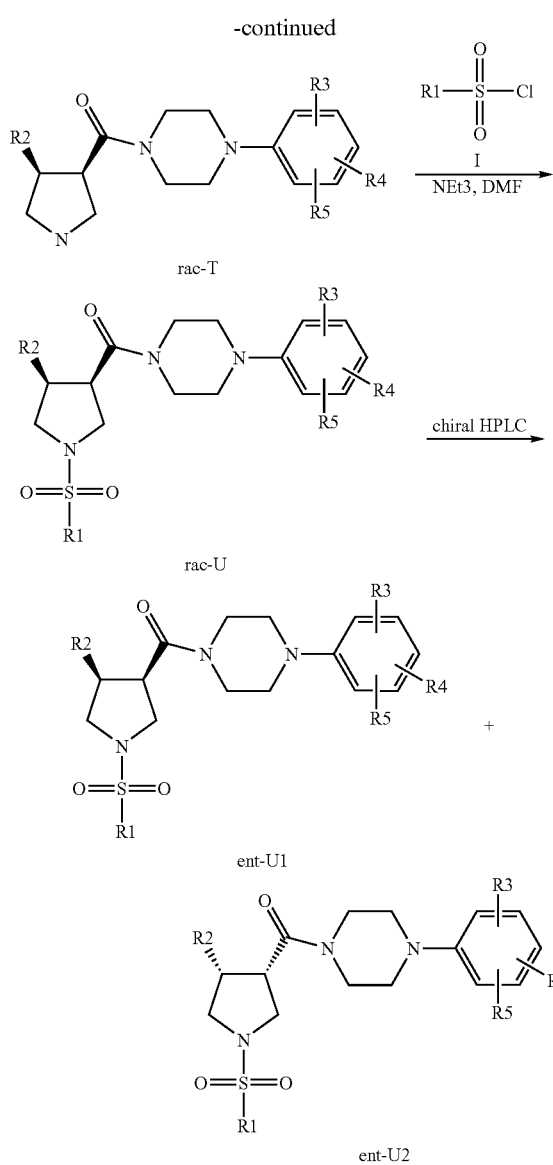

rac-T rac-U ent-U1 ent-U2

An aldehyde of the general formula C, in which R2 has the meaning described above, is reacted with methyl [bis-(2,2,2-trifluoroethoxy)phosphoryl]acetate in a polar aprotic solvent such as, for example, tetrahydrofuran in the presence of a base such as potassium bis(trimethylsilyl)amide to give the α,β-unsaturated ester with the cis configuration of the general formula P. The ester is cleaved with a base such as lithium hydroxide in a polar solvent mixture such as tetrahydrofuran and water to the free carboxylic acid of the general formula Q. The carboxylic acid is reacted with N-(methoxymethyl)-N-(trimethylsilylmethyl)-benzylamine in a nonpolar aprotic solvent such as, for example, dichloromethane in the presence of an acid such as, for example, trifluoroacetic acid to give the pyrrolidine-3-carboxylic acid with the cis configuration of the general formula R. By the action of a coupling reagent such as, for example, O-(7-azabenzotrialol-1-yl)-N,N,N',N'-tetramethyluronium hexafluorophosphate in the presence of a base such as, for example, triethylamine in a polar aprotic solvent such as N,N-dimethylformamide, the carboxylic acid of the general formula R is reacted with the piperazine of the general formula B, in which R3, R4 and R5 have the meanings described above, to give the amide of the general formula S. The action of hydrogen in the presence of a catalyst such as, for example, palladium hydroxide in a polar solvent such as methanol or, if R2 comprises a substituent which is sensitive to hydrogenolysis, by reaction with 2,2,2-trichloroethoxycarbonyl chloride in a solvent such as, for example, acetonitrile and subsequent cleavage of the resulting carbamate by the action of zinc in acetic acid on the benzyl-protected pyrrolidine of the general formula S results in the unprotected pyrrolidine of the general formula T. Reaction with a sulfonyl chloride of the general formula I, in which R1 has the meaning described above, results in the sulfonylpyrrolidine of the general formula U. If U is purified by RP-HPLC with acetonitrile/water+0.1% trifluoroacetic acid as eluent, the result is the trifluoroacetate salt of U. The racemic mixture U can be separated by chiral HPLC into the enantiopure forms of the general formulae U1 and U2.

Examples 117 to 120 were synthesized by this method.
The abbreviations used stand for:

| | |
|---|---|
| Ac | acetyl |
| Bn | benzyl |
| iBu | isobutyl |
| tBu | tert-butyl |
| BuLi | n-butyllithium |
| DCI | direct chemical ionization (in MS) |
| DCM | dichloromethane |
| DMAP | 4-N,N-dimnethylaminopyridine |
| DMF | N,N-dimethylformamide |
| DMSO | dimethyl sulfoxide |
| EA | ethyl acetate |
| ent | enantiomer/enantiomer pure |
| EI | electron impact ionization (in MS) |
| eq | equivalent |
| ESI | electron spray ionization (in MS) |
| HPLC | high pressure, high performance liquid chromatography |
| LC-MS | coupled liquid chromatography-mass spectroscopy |
| m | meta |
| Me | methyl |
| MS | mass spectroscopy |
| NMR | nuclear magnetic resonance spectroscopy |
| o | ortho |
| p | para |
| Pd/C | palladium on carbon |
| iPr | isopropyl |
| nPr | n-propyl |
| rac | racemic/racemic mixture |
| Rf | retention time (in TLC) |
| TLC | thin-layer chromatography |

Syntheses of Building Blocks by Method A:

1-(2,5-Dimethoxyphenyl)piperazine

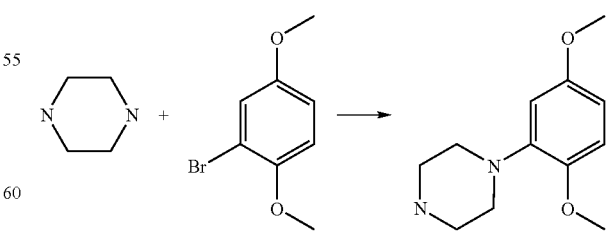

1.98 g of piperazine, 1.0 g of 1-bromo-2,5-dimethoxybenzene, 800 mg of 9,9-dimethyl-4,5-bis(diphenylphosphino)xanthene, 310 mg of palladium(II) acetate and 2.25 g of cesium carbonate are dissolved in 30 ml of 1,4-dioxane and stirred at 100° C. under an argon atmosphere for 24 hours. The reaction mixture is extracted with 50 ml of saturated sodium bicarbonate solution and 50 ml of saturated sodium chloride solution, and the combined aqueous phases are basified with 2N sodium hydroxide solution and extracted five times with 50 ml of dichloromethane each time. The combined organic phases are dried over MgSO4 and then the solvent is removed in vacuo. 500 mg of 1-(2,5-dimethoxyphenyl)piperazine are obtained as an amorphous solid.

C12H18N2O2 (222.29), LCMS (ESI): 223.3 (M+H$^+$).

Dimethyl 2-piperazin-1-ylterephthalate

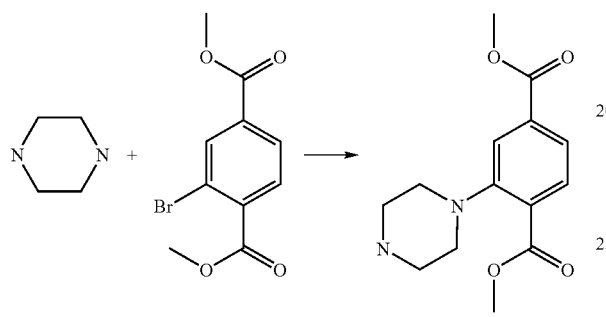

1.80 g of piperazine, 1.0 g of dimethyl 2-bromoterephthalate, 720 mg of 9,9-diemthyl-4,5-bis(diphenylphosphino)xanthene, 280 mg of palladium(II) acetate and 2.20 g of cesium carbonate are dissolved in 40 ml of 1,4-dioxane and stirred at 100° C. under an argon atmosphere for 24 hours. The reaction mixture is diluted with 100 ml of dichloromethane and extracted with 50 ml of saturated sodium bicarbonate solution and 50 ml of saturated sodium chloride solution. The organic phases is dried over MgSO4 and then the solvent is removed in vacuo. 330 mg of dimethyl 2-piperazin-1-yl terephthalate are obtained as an oil.

C14H18N2O4 (278.31), LCMS (ESI): 279.3 (M+H$^+$).

Examples of Syntheses by Method B:

EXAMPLE 1

[1-(3,5-Dimethylisoxazole-4-sulfonyl-3,4-trans-4-p-tolylpyrrolidin-3-yl]-[4-(2,5-dimethylphenyl)piperazin-1-yl]methanone trifluoroacetate

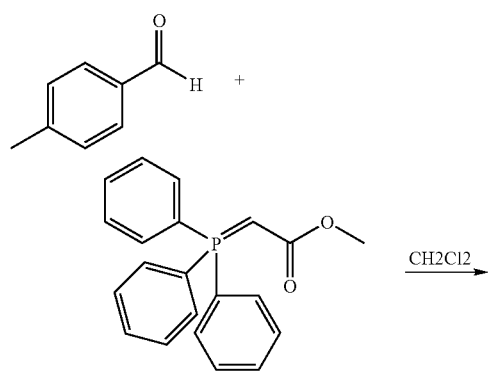

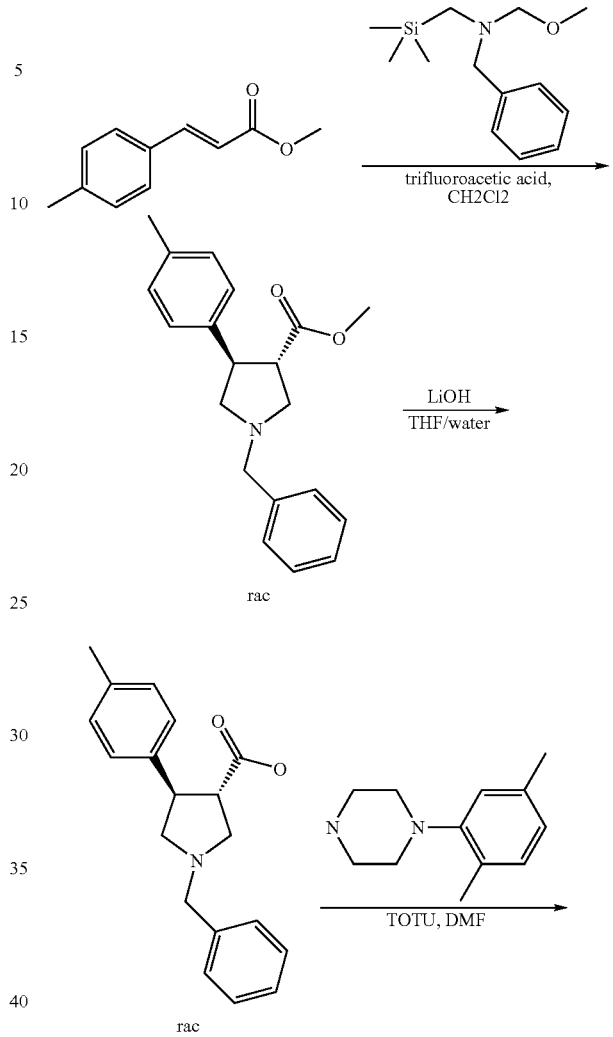

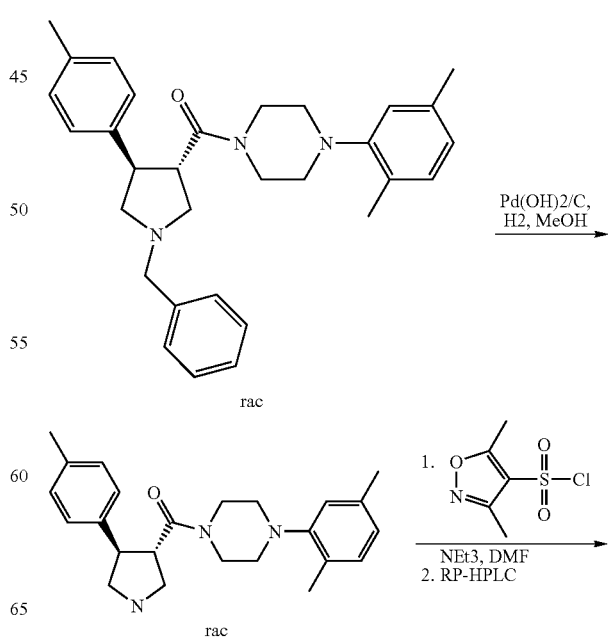

-continued

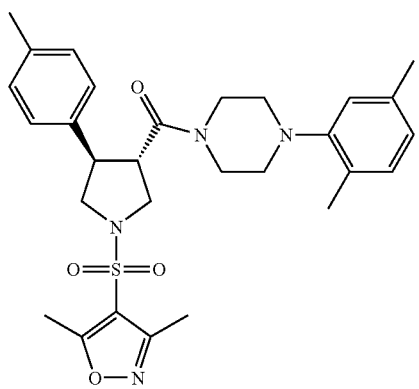

rac
Example 1

Methyl trans-3-p-tolylacrylate

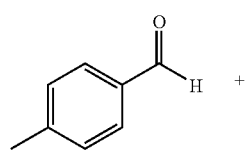

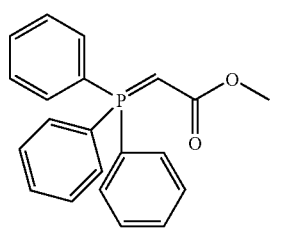

CH2Cl2 →

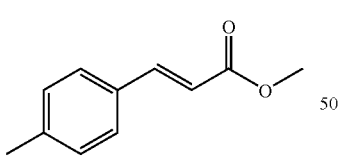

2.0 g of methyl (triphenylphosphoranylidene)acetate and 720 mg of p-toluenealdehyde are dissolved in 10 ml of dichloromethane and stirred at room temperature for twelve hours. Then, 4 g of kieselguhr are added, and the solvent is removed in vacuo. The resulting residue is purified on silica gel with n-heptane:ethyl acetate=4:1 as eluent. 850 mg of methyl trans-3-p-tolylacrylate are obtained as an oil.

C11H12O2 (176.22), LCMS (ESI): 177.2 (M+H$^+$), Rf(n-heptane:ethyl acetate=2:1)=0.71.

Methyl 1-benzyl-3,4-trans-4-p-tolylpyrrolidine-3-carboxylate

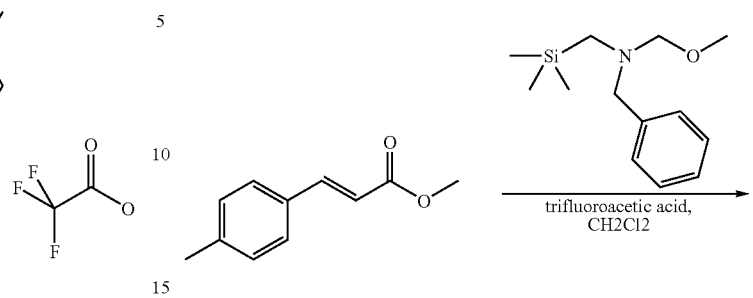

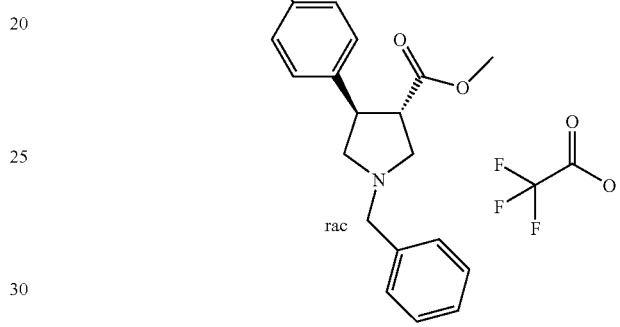

1 ml of a one molar solution of trifluoroacetic acid in dichloromethane is added dropwise at 0° C. to a solution of 1.36 ml of N-(methoxymethyl)-N-(trimethylsilylmethyl) benzylamine and 850 mg of methyl trans-3-p-tolylacrylate in 10 ml of dichloromethane. Stirring at room temperature for twelve hours is followed by removal of the solvent in vacuo and purification of the residue by RP-HPLC. 1.18 g of methyl 1-benzyl-3,4-trans-4-p-tolylpyrrolidine-3-carboxylate trifluoroacetate are obtained as a colorless oil.

C20H23NO2.C2HF3O2 (423.43), LCMS (ESI): 310.4 (M+H$^+$).

1-Benzyl-3,4-trans-4-p-tolylpyrrolidine-3-carboxylic acid

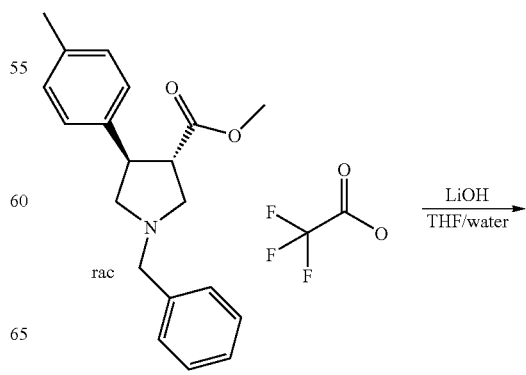

-continued

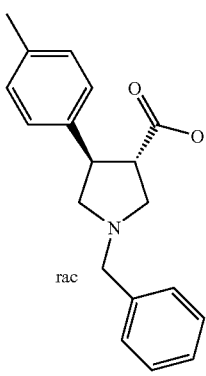

1.18 g of methyl 1-benzyl-3,4-trans-4-p-tolylpyrrolidine-3-carboxylate trifluoroacetate are dissolved in 8 ml of a mixture of tetrahydrofuran and water in the ratio five to three, and 632 mg of lithium hydroxide are added. The reaction mixture is stirred at 80° C. for two hours. After addition of dilute acetic acid, the reaction mixture is neutralized, the THF is removed in vacuo, and the residue is freeze dried. The resulting residue is purified on silica gel with dichloromethane:methanol=10:1→5:1 as eluent. 1.3 g of 1-benzyl-3,4-trans-4-p-tolylpyrrolidine-3-carboxylic acid are obtained as a colorless oil.

C19H21NO2 (295.38), LCMS (ESI): 296.4 (M+H$^+$).

(1-Benzyl-3,4-trans-4-p-tolylpyrrolidin-3-yl)-[4-(2,5-dimethylphenyl)-piperazin-1-yl]methanone

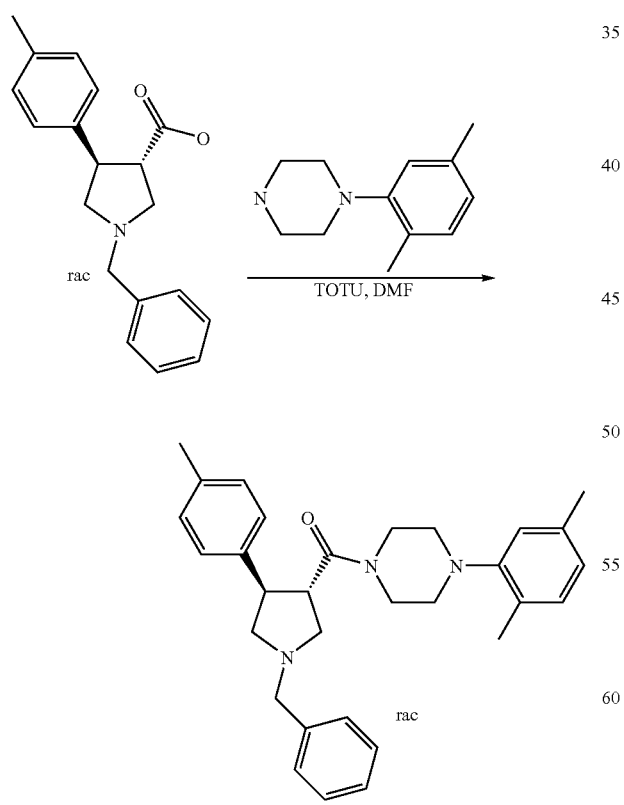

500 mg of 1-benzyl-3,4-trans-4-p-tolylpyrrolidine-3-carboxylic acid, 322 mg of commercially available 1-(2,5-dimethylphenyl)piperazine and 0.97 ml of triethylamine are dissolved in 30 ml of dimethylformamide. 555 mg of O-[cyano(ethoxycarbonyl)methyleneamino]-1,1,3,3-tetramethyluronium tetrafluoroborate are added, and the mixture is stirred at room temperature. After one hour, the reaction mixture is diluted by adding 100 ml of ethyl acetate and is washed five times with 30 ml of saturated sodium bicarbonate solution each time. The organic phase is dried over MgSO4 and then the solvent is removed in vacuo. 520 mg of (1-benzyl-3,4-trans-4-p-tolylpyrrolidin-3-yl)-[4-(2,5-dimethylphenyl)piperazin-1-yl]methanone are obtained as an oil.

C31H37N3O (467.66), LCMS (ESI): 468.7 (M+H$^+$).

[4-(2,5-Dimethylphenyl)piperazin-1-yl]-(3,4-trans-4-p-tolylpyrrolidin-3-yl)-methanone 520 mg of (1-benzyl-3,4-trans-4-p-tolylpyrrolidin-3-yl)-[4-(2,5-dimethyl-phenyl)piperazin-1-yl]methanone are dissolved in 15 ml of methanol, and 30 mg of palladium hydroxide on carbon are added. The mixture is stirred under an atmosphere of 5 bar of hydrogen for four hours. The reaction mixture is then filtered through Celite, and the filtrate is concentrated in vacuo. 360 mg of [4-(2,5-dimethylphenyl)piperazin-1-yl]-(3,4-trans-4-p-tolyl-pyrrolidin-3-yl)methanone are obtained as an oil.

C24H31N3O (377.53), LCMS (ESI): 378.5 (M+H⁺).

[1-(3,5-Dimethylisoxazole-4-sulfonyl)-3,4-trans-4-p-tolylpyrrolidin-3-yl]-[4-(2,5-dimethylphenyl)piperazin-1-yl]methanone trifluoroacetate

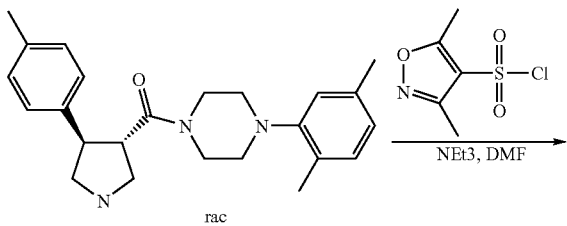

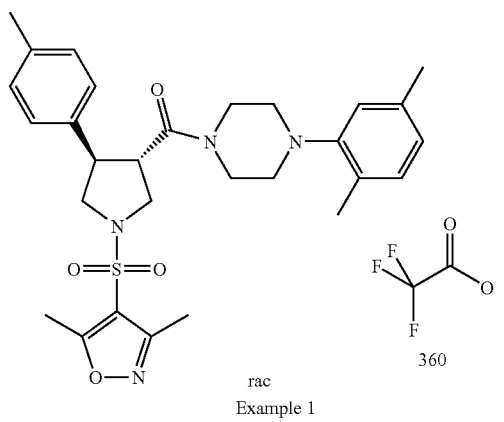

Example 1 mg of [4-(2,5-dimethylphenyl)piperazin-1-yl]-3,4-trans-4-p-tolyl pyrrolidin-3-yl)methanone and 0.56 ml of N,N-diisopropyl-N-ethylamine are dissolved in 10 ml of dimethylformamide, and 186 mg of 3,5-dimethylisoxazole-4-sulfonyl chloride are added. After 15 minutes, the reaction mixture is diluted by adding 50 ml of ethyl acetate and is washed with 20 ml of saturated sodium bicarbonate solution and three times with 20 ml of water each time. The organic phase is dried over MgSO4 and then the solvent is removed in vacuo. The residue is purified by RP-HPLC. 212 mg of [1-(3,5-dimethyl-isoxazole-4-sulfonyl)-3,4-trans-4-p-tolylpyrrolidin-3-yl]-2,5-dimethylphenyl)-piperazin-1-yl]methanone trifluoroacetate are obtained as a colorless lyophilizate.

C29H36O4S.C2HF3O2 (650.72), LCMS (ESI): (M+H⁺).

EXAMPLE 2

[1-(Biphenyl-4-sulfonyl)-3,4-trans-4-phenylpyrrolidin-3-yl]-4-o-tolylpiperazin-1-yl)methanone

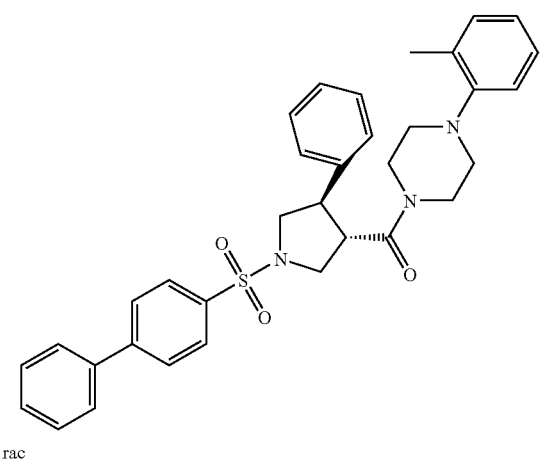

[1-(Biphenyl-4-sulfonyl)-3,4-trans-4-phenylpyrrolidin-3-yl]-4-o-tolylpiperazin-1-yl)methanone is obtained in analogy to example 1 from the commercially available reagents methyl (E)-cinnamate, N-(methoxymethyl)-N-(trimethylsilylmethyl)benzylamine, 1-o-tolylpiperazine and biphenyl-4-sulfonyl chloride.

C34H35N3O3S (565.74), LCMS (ESI): 566.8 (M+H⁺).

EXAMPLE 3

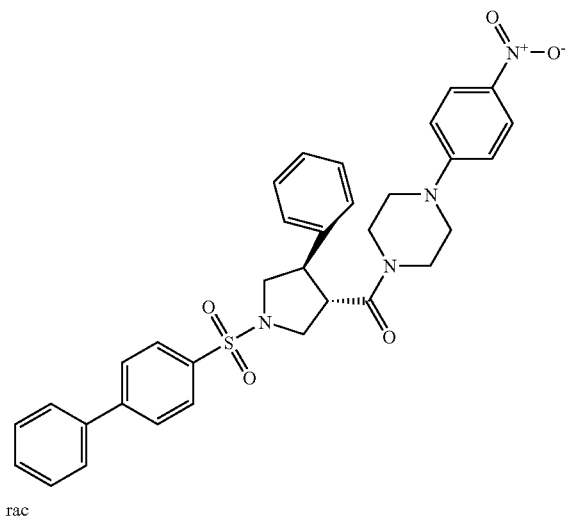

[1-(Biphenyl-4-sulfonyl)-3,4-trans-4-phenylpyrrolidin-3-yl]-[4-(4-nitrophenyl)piperazin-1-yl]methanone is obtained in analogy to example 1 from the commercially available reagents methyl (E)-cinnamate, N-(methoxymethyl)-N-(trimethylsilylmethyl)benzylamine, 1-(1-nitropyridin-4-yl)piperazine and biphenyl-4-sulphonyl chloride. C33H32N4O5S (596.71), LCMS (ESI): 597.7 (M+H⁺).

EXAMPLE 4

[1-(2,5-Dichlorobenzenesulfonyl)-3,4-trans-4-phenylpyrrolidin-3-yl]-[4-(3-trifluoromethylphenyl)piperazin-1-yl]methanone

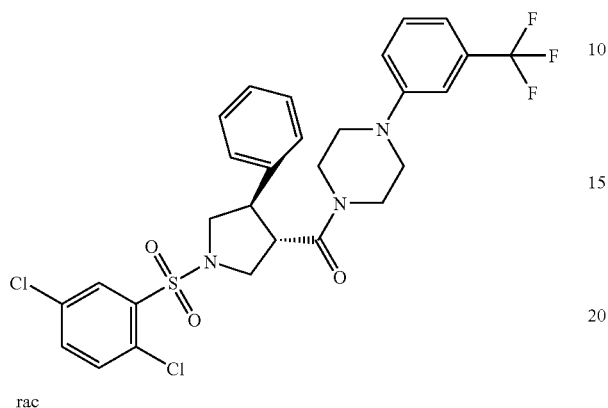

rac

[1-(2,5-Dicholorbenzenesulfonyl)-3,4-trans-4-phenylpyrrolidin-3-yl]-[4-(3-trifluoromethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(3-trifluoromethylphenyl)piperazine and 2,5-dichlorobenzenesulfonyl chloride.

C28H26Cl2F3N3O3S (612.50), LCMS (ESI): 612.1, 614.1 (M+H$^+$).

EXAMPLE 5

[1-(2,5-Dimethoxybenzenesulfonyl)-3,4-trans-4-phenylpyrrolidin-3-yl]-(4-phenylpiperazin-1-yl)methanone

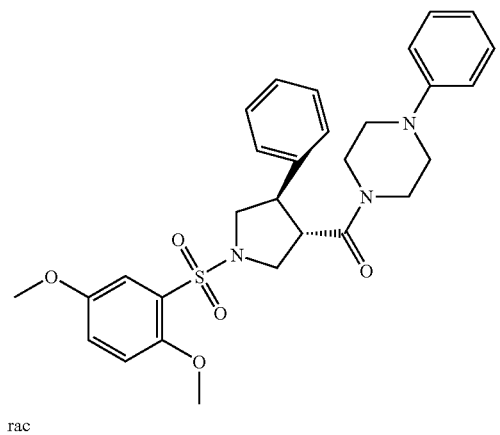

rac

[1-(2,5-Dimethoxybenzenesulfonyl)-3,4-trans-4-phenylpyrrolidin-3-yl]-(4-phenylpiperazin-1-yl)methanone is obtained in analogy to example 1 from the commercially available reagents methyl (E)-cinnamate, N-(methoxymethyl)-N-(trimethylsilylmethyl)benzylamine, 1-phenylpiperazine and 2,5-dimethoxybenzenesulfonyl chloride.

C29H33N3O5S (535.67), LCMS (ESI): 536.7 (M+H$^+$).

EXAMPLE 6

(4-Phenylpiperazin-1-yl)-[3,4-trans-4-phenyl-1-(2,4,6-triisopropylbenzenesulfonyl)pyrrolidin-3-yl]methanone

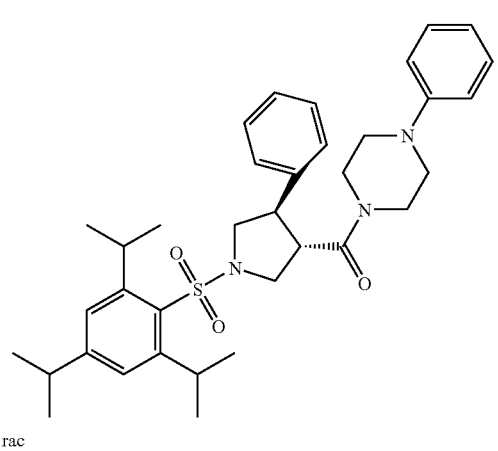

rac (4-Phenylpiperazin-1-yl)-[3,4-trans-4-phenyl-1-(2,4,6-triisopropylbenzenesulfonyl)pyrrolidin-3-yl]methanone is obtained in analogy to example 1 from the commercially available reagents methyl (E)-cinnamate, N-(methoxymethyl)-N-(trimethylsilylmethyl)benzylamine, 1-phenylpiperazine and 2,4,6-triisopropylbenzenesulfonyl chloride.

C36H47N3O3S (601.86), LCMS (ESI): 602-9 (M+H$^+$).

EXAMPLE 7

1-(4-{4-[3,4-trans-4-Phenyl-1-(thiophene-2-sulfonyl)pyrrolidine-3-carbonyl]-piperazin-1-yl}phenyl)ethanone

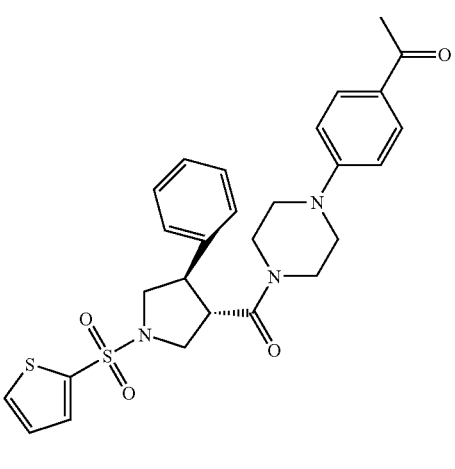

rac 1-(4-{4-[3,4-trans-4-Phenyl-1-(thiophene-2-sulfonyl)pyrrolidine-3-carbonyl]-piperazin-1-yl}phenyl)ethanone is obtained in analogy to example 1 from the commercially available reagents methyl (E)-cinnamate, N-(methoxymethyl)-N-(trimethylsilylmethyl)benzylamine, 1-(4-piperazin-1-ylphenyl)ethanone and thiophene-2-sulfonyl chloride.

C27H29N3O4S2 (523.68), LCMS (ESI): 524.7 ((M+H⁺).

EXAMPLE 8

[1-(4-Chlorobenzenesulfonyl)-3,4-trans-4-phenylpyrrolidin-3-yl]-[4-(2,5-dimethylphenyl)piperazin-1-yl]methanone

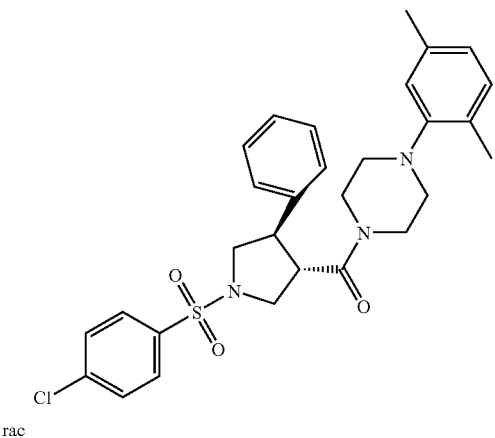

rac

[1-(4-Chlorobenzenesulfonyl)-3,4-trans-4-phenylpyrrolidin-3-yl]-[4-(2,5-dimethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(2,5-dimethylphenyl)piperazine and 5-chlorothiophene-2-sulfonyl chloride.

C29H32ClN3O3S (538.11), LCMS (ESI): 538.1 (M+H⁺).

EXAMPLE 9

[4-(2,3-Dimethylphenyl)piperazin-1-yl]-[3,4-trans-4-phenyl-1-(4-propylbenzenesulfonyl)pyrrolidin-3-yl]methanone

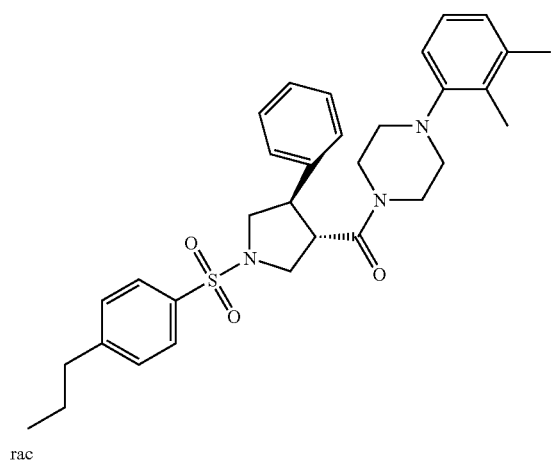

rac

[4-(2,3-Dimethylphenyl)piperazin-1-yl]-[3,4-trans-4-phenyl-1-(4-propylbenzenesulfonyl)pyrrolidin-3-yl]methanone is obtained in analogy to example 1 from the commercially available reagents methyl (E)-cinnamate, N-(methoxymethyl)-N-(trimethylsilylmethyl)benzylamine, 1-(2,3-dimethylphenyl)piperazine and 4-propylbenzenesulfonyl chloride.

C32H39N3O3S (545.75), LCMS (ESI): 546.8 (M+H⁺).

EXAMPLE 10

[1-(3-Chloro-4-fluorobenzenesulfonyl)-3,4-trans-4-phenylpyrrolidin-3-yl]-[4-(2,5-dimethylphenyl)piperazin-1-yl]methanone

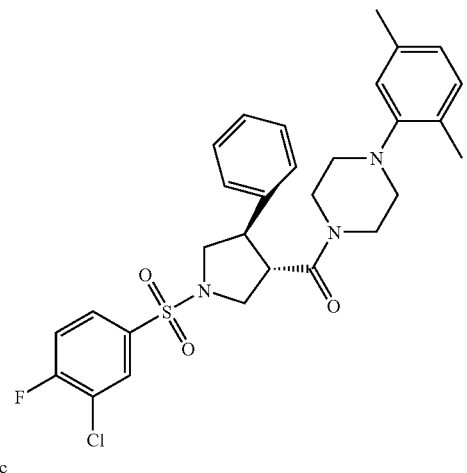

rac

[1-(3-Chloro-4-fluorobenzenesulfonyl)-3,4-trans-4-phenylpyrrolidin-3-yl]-[4-(2,5-dimethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(2,5-dimethyl-phenyl)piperazine and 3-chloro-4-fluorobenzenesulfonyl chloride.

C29H31ClFN3O3S (556.10), LCMS (ESI): 556.3 (M+H⁺).

EXAMPLE 11

[4-(2-Chlorophenyl)piperazin-1-yl]-[3,4-trans-4-phenyl-1-(quinolin-8-sulfonyl)pyrrolidin-3-yl]methanone

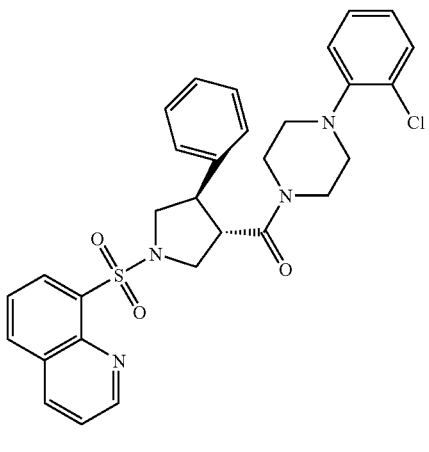

rac

[4-(2-Chlorophenyl)piperazin-1-yl]-[3,4-trans-4-phenyl-1-(quinolin-8-sulfonyl)pyrrolidin-3-yl]methanone is obtained in analogy to example 1 from the commercially available reagents methyl (E)-cinnamate, N-(methoxymethyl)-N-(trimethylsilylmethyl)benzylamine, 1-(2-chlorophenyl)-piperazine and quinolin-8-sulfonyl chloride.

C30H29ClN4O3S (561.11), LCMS (ESI): 561.1 (M+H$^+$).

EXAMPLE 12

[4-(4-Chlorophenyl)piperazin-1-yl]-(3,4-trans-4-phenyl-1-phenylmethane-sulfonylpyrrolidin-3-yl)methanone

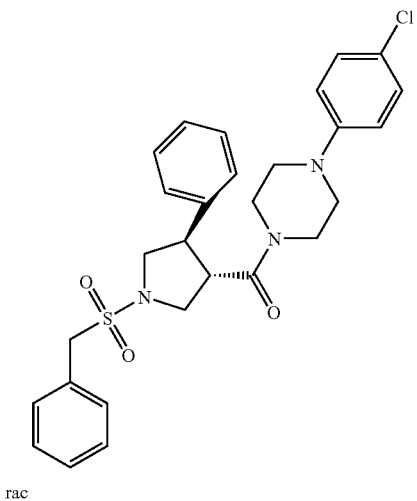

rac

[4-(4-Chlorophenyl)piperazin-1-yl]-(3,4-trans-4-phenyl-1-phenylmethane-sulfonylpyrrolidin-3-yl)methanone is obtained in analogy to example 1 from the commercially available reagents methyl (E)-cinnamate, N-(methoxymethyl)-N-(trimethylsilylmethyl)benzylamine, 1-(4-chlorophenyl)-piperazine and phenylmethanesulfonyl chloride.

C28H30ClN3O3S (524.09), LCMS (ESI): 524.1 (M+H$^+$).

EXAMPLE 13

[4-(4-Methoxyphenyl)piperazin-1-yl]-[3,4-trans-4-phenyl-1-(2-phenyl-(E)-ethenesulfonyl)pyrrolidin-3-yl]methanone

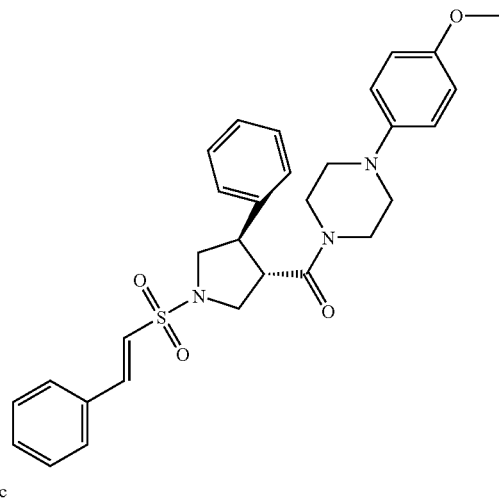

rac

[4-(4-Methoxyphenyl)piperazin-1-yl]-[3,4-trans-4-phenyl-1-(2-phenyl-(E)-ethenesulfonyl)pyrrolidin-3-yl]methanone is obtained in analogy to example 1 from the commercially available reagents methyl (E)-cinnamate, N-(methoxymethyl)-N-(trimethylsilylmethyl)benzylamine, 1-(4-methoxyphenyl)piperazine and (E)-3-phenylprop-2-ene-1-sulfonyl chloride.

C30H33N3O4S (531.68), LCMS (ESI): 532.7 (M+H$^+$).

EXAMPLE 14

[4-(2-Chlorophenyl)piperazin-1-yl]-[3,4-trans-4-phenyl-1-(4-trifluoro-methoxybenzenesulfonyl)pyrrolidin-3-yl]methanone

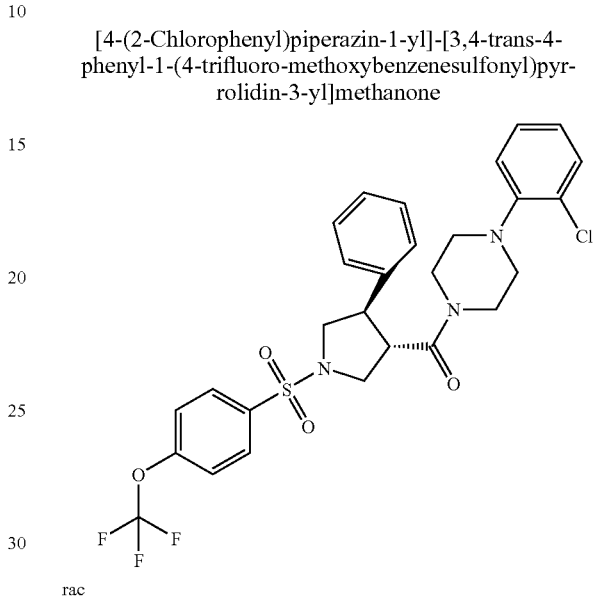

rac

[4-(2-Chlorophenyl)piperazin-1-yl]-[3,4-trans-4-phenyl-1-(4-trifluoro-methoxybenzenesulfonyl)pyrrolidin-3-yl]methanone is obtained in analogy to example 1 from the commercially available reagents methyl (E)-cinnamate, N-(methoxymethyl)-N-(trimethylsilylmethyl)benzylamine, 1-(2-chlorophenyl)piperazine and 4-trifluoromethoxybenzenesulfonyl chloride.

C28H27ClF3N3O4S (594.06), LCMS (ESI): 594.1 (M+H$^+$).

EXAMPLE 15

1-(4-Chlorophenyl)piperazine and 4-nitrobenzenesulfonyl chloride; [4-(4-chlorophenyl)piperazin-1-yl]-[1-(4-nitrobenzenesulfonyl)-3,4-trans-4-phenyl-pyrrolidin-3-yl]methanone

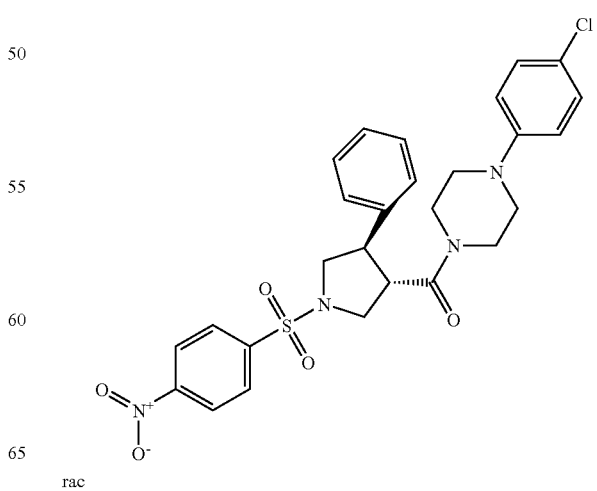

rac

[4-(4-Chlorophenyl)piperazin-1-yl]-[1-(4-nitrobenzenesulfonyl)-3,4-trans-4-phenylpyrrolidin-3-yl]methanone is obtained in analogy to example 1 from the commercially available reagents methyl (E)-cinnamate, N-(methoxymethyl)-N-(trimethylsilylmethyl)benzylamine, 1-(4-chlorophenyl)-piperazine and 4-nitrobenzenesulfonyl chloride.

C27H27ClN4O5S (555.06), LCMS (ESI): 555.1 (M+H$^+$).

EXAMPLE 16

[1-(4-tert-Butylbenzenesulfonyl)-3,4-trans-4-phenylpyrrolidin-3-yl]-[4-(4-methoxyphenyl)piperazin-1-yl]methanone

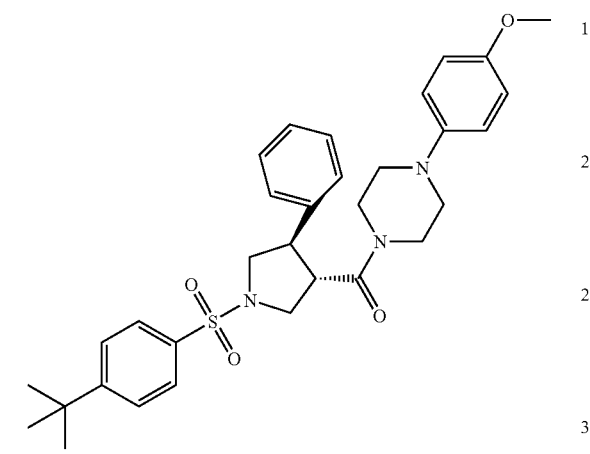

rac

[1-(4-tert-Butylbenzenesulfonyl)-3,4-trans-4-phenylpyrrolidin-3-yl]-[4-(4-methoxyphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(4-methoxy-phenyl)piperazine and 4-tert-butylbenzenesulfonyl chloride.

C32H39N3O4S (561.75), LCMS (ESI): 562.8 (M+H$^+$).

EXAMPLE 17

[4-(4-Methoxyphenyl)piperazin-1-yl]-[3,4-trans-4-phenyl-1-(3-trifluoromethylbenzenesulfonyl)pyrrolidin-3-yl]methanone

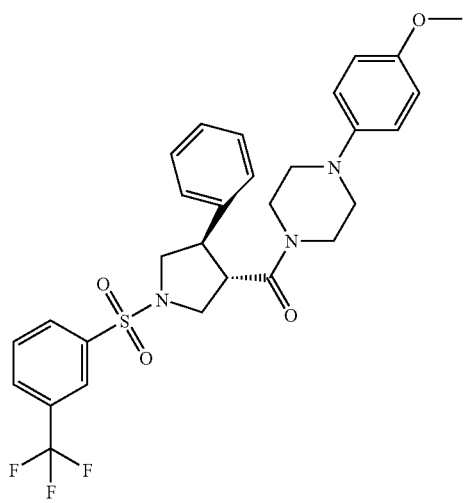

[4-(4-Methoxyphenyl)piperazin-1-yl]-[3,4-trans-4-phenyl-1-(3-trifluoromethylbenzenesulfonyl)pyrrolidin-3-yl] methanone is obtained in analogy to example 1 from the commercially available reagents methyl (E)-cinnamate, N-(methoxymethyl)-N-(trimethylsilylmethyl)benzylamine, 1-(4-methoxyphenyl)piperazine and 3-trifluoromethylbenzenesulfonyl chloride.

C29H30F3N3O4S (573.64), LCMS (ESI): 574.6 (M+H$^+$).

EXAMPLE 18

[4-(2-Ethoxyphenyl)piperazin-1-yl]-[1-(naphthalene-2-sulfonyl)-3,4-trans-4-phenylpyrrolidin-3-yl]methanone

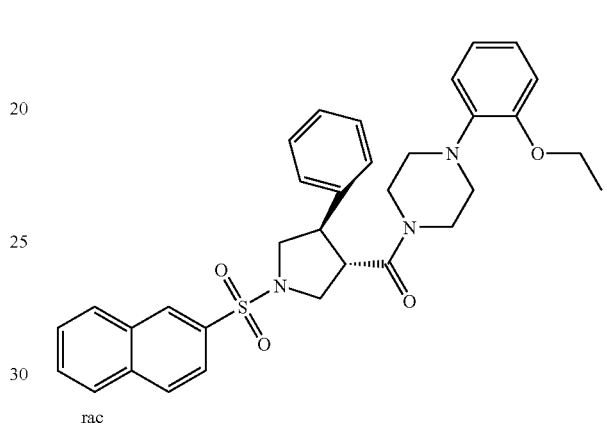

rac

[4-(2-Ethoxyphenyl)piperazin-1-yl]-[1-(naphthalene-2-sulfonyl)-3,4-trans-4-phenylpyrrolidin-3-yl]methanone is obtained in analogy to example 1 from the commercially available reagents methyl (E)-cinnamate, N-(methoxymethyl)-N-(trimethylsilylmethyl)benzylamine, 1-(2-ethoxyphenyl)-piperazine and naphthalene-2-sulfonyl chloride.

C33H35N3O4S (569.73), LCMS (ESI): 570.7 (M+H$^+$).

EXAMPLE 19

[1-(4,5-Dibromothiophene-2-sulfonyl)-3,4-trans-4-phenylpyrrolidin-3-yl]-[4-(2-fluorophenyl)piperazin-1-yl]methanone

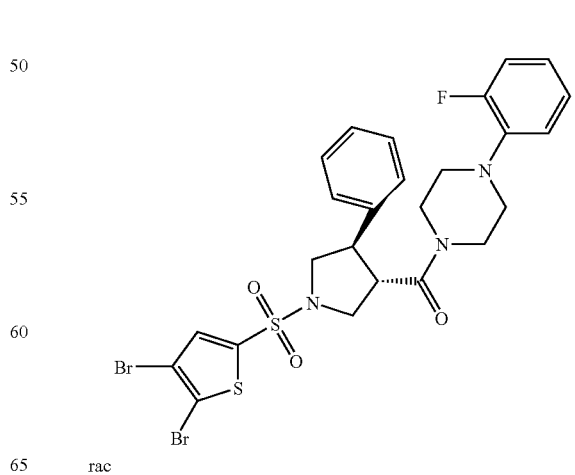

rac

[1-(4,5-Dibromothiophene-2-sulfonyl)-3,4-trans-4-phenylpyrrolidin-3-yl]-[4-(2-fluorophenyl)piperazin-1-yl]methanone is obtained in analogy to example 1 from the commercially available reagents methyl (E)-cinnamate, N-(methoxymethyl)-N-(trimethylsilylmethyl)benzylamine, 1-(2-fluorophenyl)-piperazine and 4,5-dibromothiophene-2-sulfonyl chloride.

C25H24Br2FN3O3S2 (657.42), LCMS (ESI): 656.1, 660.1 (M+H$^+$).

EXAMPLE 20

1-(5-Chlorothiophene-2-sulfonyl)-3,4-trans-4-phenylpyrrolidin-3-yl]-(4-phenylpiperazin-1-yl)methanone

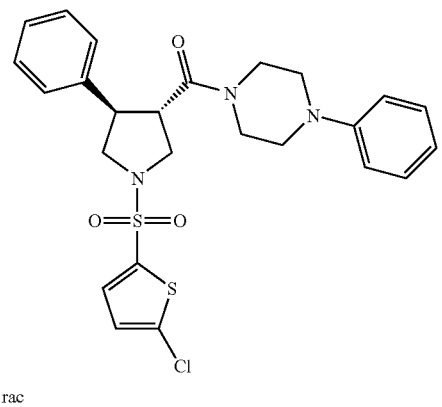

rac phenylpiperazin-1-yl)methanone is obtained in analogy to example 1 from the commercially available reagents methyl (E)-cinnamate, N-(methoxymethyl)-N-(trimethylsilylmethyl)benzylamine, 1-phenylpiperazine and 5-chlorothiophene-2-sulfonyl chloride.

C25H26ClN3O3S2 (516.09), LCMS (ESI): 516.1 (M+H$^+$).

EXAMPLE 21

[1-(4,5-Dichlorothiophene-2-sulfonyl)-3,4-trans-4-phenylpyrrolidin-3-yl]-(4-phenylpiperazin-1-yl)methanone

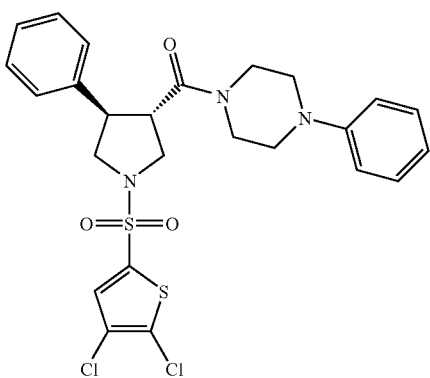

rac

[1-(4,5-Dichlorothiophene-2-sulfonyl)-3,4-trans-4-phenylpyrrolidin-3-yl]-(4-phenylpiperazin-1-yl)methanone is obtained in analogy to example 1 from the commercially available reagents methyl (E)-cinnamate, N-(methoxymethyl)-N-(trimethylsilylmethyl)benzylamine, 1-phenylpiperazine and 4,5-dichlorothiophene-2-sulfonyl chloride.

C25H25Cl2N3O3S2 (550.53), LCMS (ESI): 550.1 (M+H$^+$).

EXAMPLE 22

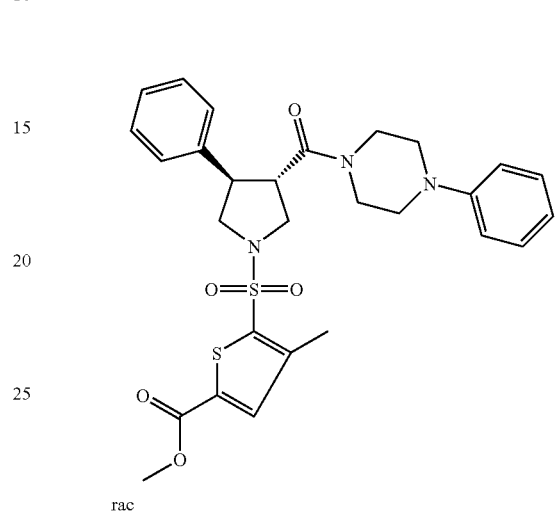

rac

Methyl 4-methyl-5-[3,4-trans-3-phenyl-4-(4-phenylpiperazine-1-carbonyl)-pyrrolidine-1-sulfonyl]thiophene-2-carboxylate is obtained in analogy to example 1 from the commercially available reagents methyl (E)-cinnamate, N-(methoxymethyl)-N-(trimethylsilylmethyl)benzylamine, 1-phenylpiperazine and methyl 5-chlorosulfonyl-4-methylthiophene-2-carboxylate.

C28H31N3O5S2 (553.70), LCMS (ESI): 554.1 (M+H$^+$).

EXAMPLE 23

[1-(5-Chloro-3-methylbenzo[b]thiophene-2-sulfonyl)-3,4-trans-4-phenyl-pyrrolidin-3-yl]-(4-phenylpiperazin-1-yl)methanone

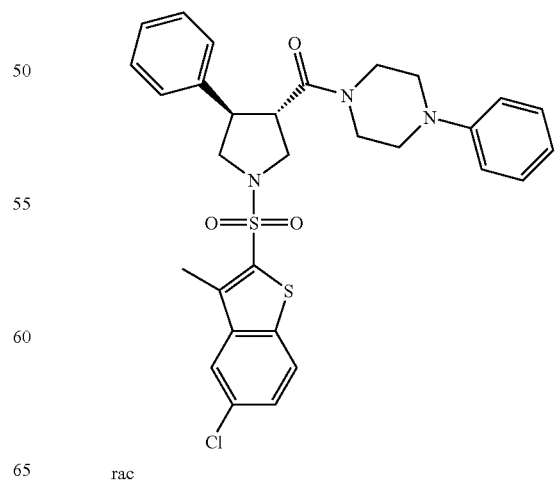

rac

[1-(5-Chloro-3-methylbenzo[b]thiophene-2-sulfonyl)-3,4-trans-4-phenyl-pyrrolidin-3-yl]-(4-phenylpiperazin-1-yl) methanone is obtained in analogy to example 1 from the commercially available reagents methyl (E)-cinnamate, N-(methoxymethyl)-N-(trimethylsilylmethyl)benzylamine, 1-phenylpiperazine and 5-chloro-3-methylbenzo[b] thiophene-2-sulfonyl chloride.

C30H30Cl3O3S2 (580.17), LCMS (ESI): 580.2 (M+H+).

EXAMPLE 24

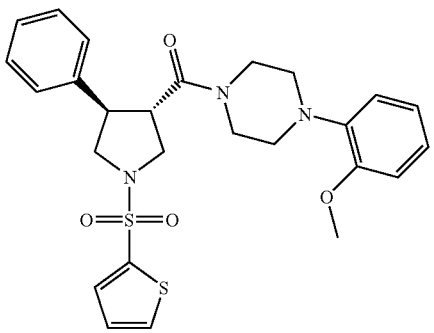

rac

[4-(2-Methoxyphenyl)piperazin-1-yl]-[3,4-trans-4-phenyl-1-(thiophene-2-sulfonyl)pyrrolidin-3-yl]methanone is obtained in analogy to example 1 from the commercially available reagents methyl (E)-cinnamate, N-(methoxymethyl)-N-(trimethylsilylmethyl)benzylamine, 1-(2-methoxyphenyl)piperazine and thiophene-2-sulfonyl chloride.

C26H29N3O4S2 (511.67), LCMS (ESI): 512.1 (M+H+).

EXAMPLE 25

[1-(4,5-Dibromothiophene-2-sulfonyl)-3,4-trans-4-phenylpyrrolidin-3-yl]-[4-(2-methoxyphenyl)piperazin-1-yl]methanone

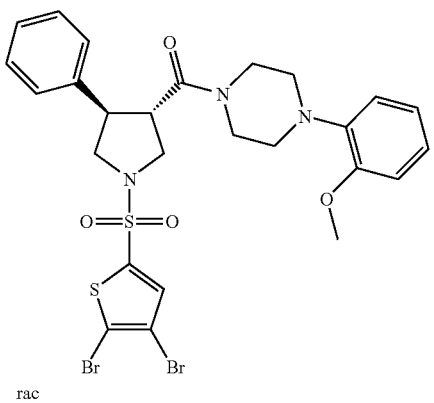

rac

[1-(4,5-Dibromothiophene-2-sulfonyl)-3,4-trans-4-phenylpyrrolidin-3-yl]-[4-(2-methoxyphenyl)piperazin-1-yl] methanone is obtained in analogy to example 1 from the commercially available reagents methyl (E)-cinnamate, N-(methoxymethyl)-N-(trimethylsilylmethyl)benzylamine, 1-(2-methoxyphenyl)piperazine and 4,5-dibromothiophene-2-sulfonyl chloride.

C26H27Br2N3O4S2 (669.46), LCMS (ESI): 669.9, 671.9 (M+H+).

EXAMPLE 26

[1-(5-Chlorothiophene-2-sulfonyl)-3,4-trans-4-phenylpyrrolidin-3-yl]-[4-(2-methoxyphenyl)piperazin-1-yl]methanone

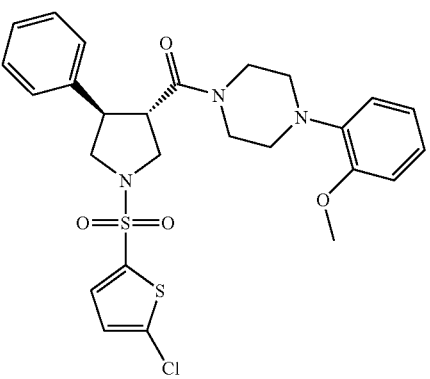

rac

[1-(5-Chlorothiophene-2-sulfonyl)-3,4-trans-4-phenylpyrrolidin-3-yl]-[4-(2-methoxyphenyl)piperazin-1-yl] methanone is obtained in analogy to example 1 from the commercially available reagents methyl (E)-cinnamate, N-(methoxymethyl)-N-(trimethylsilylmethyl)benzylamine, 1-(2-methoxyphenyl)piperazine and 5-chlorothiophene-2-sulfonyl chloride.

C26H28ClN3O4S2 (546.11), LCMS (ESI): 546.0 (M+H+).

EXAMPLE 27

[1-(4,5-Dichlorothiophene-2-sulfonyl)-3,4-trans-4-phenylpyrrolidin-3-yl]-[4-(2-methoxyphenyl)piperazin-1-yl]methanone

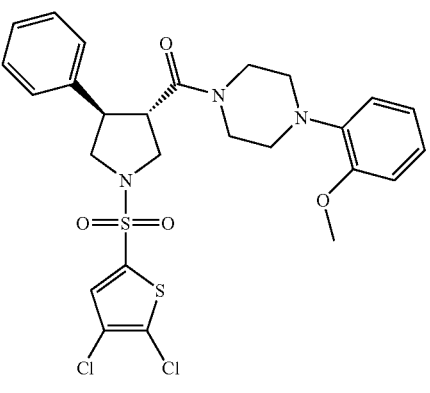

rac

[1-(4,5-Dichlorothiophene-2-sulfonyl)-3,4-trans-4-phenylpyrrolidin-3-yl]-[4-(2-methoxyphenyl)piperazin-1-yl] methanone is obtained in analogy to example 1 from the commercially available reagents methyl (E)-cinnamate, N-(methoxymethyl)-N-(trimethylsilylmethyl)benzylamine, 1-(2-methoxyphenyl)piperazine and 4,5-dichlorothiophene-2-sulfonyl chloride.

C26H27Cl2N3O4S2 (580.56), LCMS (ESI): 580.0 (M+H$^+$).

EXAMPLE 28

Methyl [5-{3,4-trans-3-[4-(2-methoxyphenyl)piperazine-1-carbonyl]-4-phenylpyrrolidine-1-sulfonyl}-4-methylthiophene-2-carboxylate

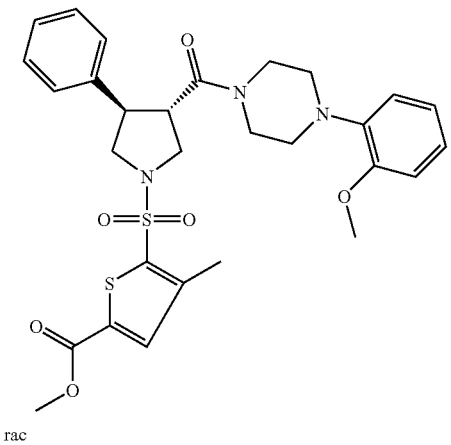

rac

Methyl [5-{3,4-trans-3-[4-(2-methoxyphenyl)piperazine-1-carbonyl]-4-phenylpyrrolidine-1-sulfonyl}-4-methylthiophene-2-carboxylate is obtained in analogy to example 1 from the commercially available reagents methyl (E)-cinnamate, N-(methoxymethyl)-N-(trimethylsilylmethyl)benzylamine, 1-(2-methoxyphenyl)piperazine and methyl 5-chlorosulfonyl-4-methylthiophene-2-carboxylate.

C29H33N3O6S2 (583.73), LCMS (ESI): 584.1 (M+H$^+$).

EXAMPLE 29

[1-(5-Chloro-3-methylbenzo[b]thiophene-2-sulfonyl)-3,4-trans-4-phenyl-pyrrolidin-3-yl]-[4-(2-methoxyphenyl)piperazin-1-yl]methanone

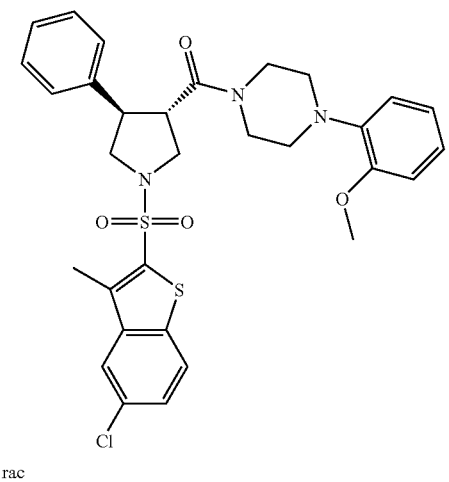

rac

[1-(5-Chloro-3-methylbenzo[b]thiophene-2-sulfonyl)-3,4-trans-4-phenyl-pyrrolidin-3-yl]-[4-(2-methoxyphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(2-methoxyphenyl)piperazine and 5-chloro-3-methylbenzo[b]thiophene-2-sulfonyl chloride.

C31H32ClN3O4S2 (610.20), LCMS(ESI): 610.2 (M+H$^+$).

EXAMPLE 30

[3,4-trans-4-Phenyl-1-(thiophene-2-sulfonyl)pyrrolidin-3-yl]-[4-(3-trifluoromethylphenyl)piperazin-1-yl]methanone

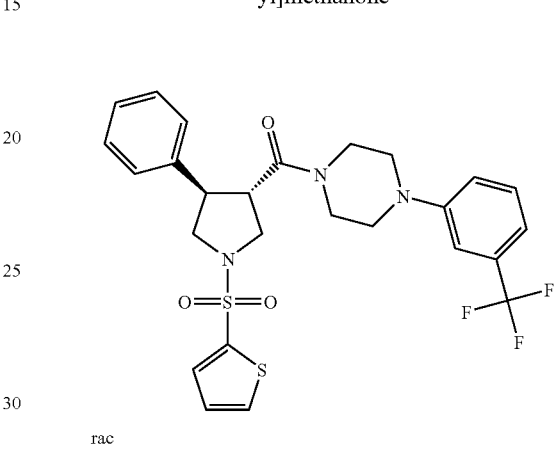

rac

[3,4-trans-4-Phenyl-1-(thiophene-2-sulfonyl)pyrrolidin-3-yl]-[4-(3-trifluoro-methylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-3-trifluoromethyl-phenyl)piperazine and thiophene-2-sulfonyl chloride.

C26H26F3N3O3S2 (549.64), LCMS(ESI): 550.1 (M+H$^+$).

EXAMPLE 31

[1-(4,5-Dibromothiophene-2-sulfonyl)-3,4-trans-4-phenylpyrrolidin-3-yl]-[4-(3-trifluoromethylphenyl)piperazin-1-yl]methanone

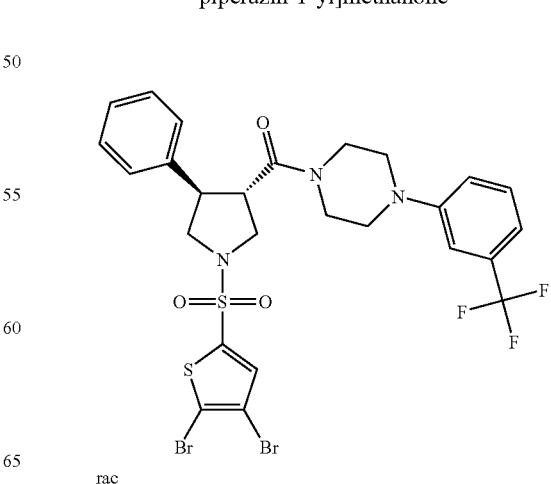

rac

[1-(4,5-Dibromothiophene-2-sulfonyl)-3,4-trans-4-phenylpyrrolidin-3-yl]-[4-(3-trifluoromethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(3-trifluoromethylphenyl)piperazine and 4,5-dibromothiophene-2-sulfonyl chloride.

C26H24Br2F3N3O3S2 (707.43), LCMS(ESI): 708.0 (M+H⁺).

EXAMPLE 32

[1-(5-Chlorothiophene-2-sulfonyl)-3,4-trans-4-phenylpyrrolidin-3-yl]-[4-(3-trifluoromethylphenyl)piperazin-1-yl]methanone

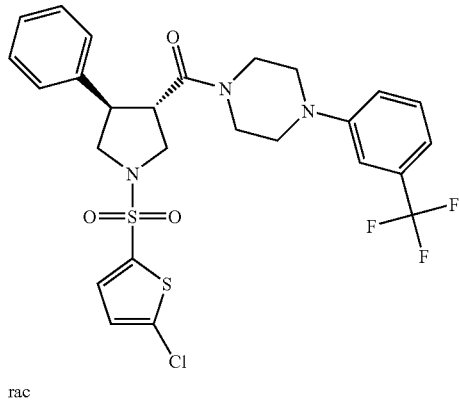

rac

[1-(5-Chlorothiophene-2-sulfonyl)-3,4-trans-4-phenylpyrrolidin-3-yl]-[4-(3-trifluoromethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(3-trifluoromethylphenyl)piperazine and 5-chlorothiophene-2-sulfonyl chloride.

C26H25ClF3N3O3S2 (584.08), LCMS(ESI): 584.1 (M+H⁺).

EXAMPLE 33

[1-(4,5-Dichlorothiophene-2-sulfonyl)-3,4-trans-4-phenylpyrrolidin-3-yl]-[4-(3-trifluoromethylphenyl)piperazin-1-yl]methanone

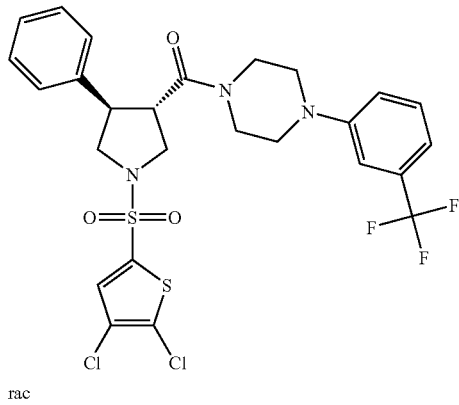

rac

[1-(4,5-Dichlorothiophene-2-sulfonyl)-3,4-trans-4-phenylpyrrolidin-3-yl]-[4-(3-trifluoromethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(3-trifluoromethylphenyl)piperazine and 4,5-dichlorothiophene-2-sulfonyl chloride.

C26H24Cl2F3N3O3S2 (618.53), LCMS(ESI): 618.1 (M+H⁺).

EXAMPLE 34

Methyl 4-methyl-5-{3,4-trans-3-phenyl-4-[4-(3-trifluoromethylphenyl)-piperazine-1-carbonyl]pyrrolidine-1-sulfonyl}thiophene-2-carboxylate

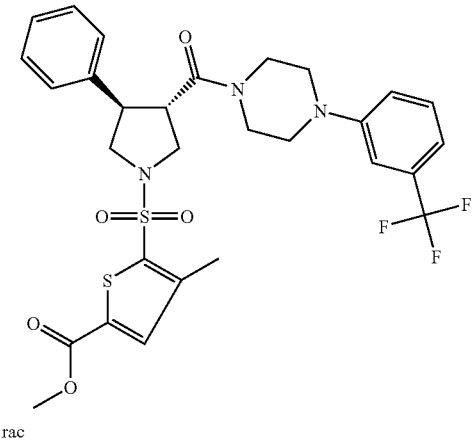

rac

Methyl 4-methyl-5-{3,4-trans-3-phenyl-4-[4-(3-trifluoromethylphenyl)-piperazine-1-carbonyl]pyrrolidine-1-sulfonyl}thiophene-2-carboxylate is obtained in analogy to example 1 from the commercially available reagents methyl (E)-cinnamate, N-(methoxymethyl)-N-(trimethylsilylmethyl)benzylamine, 1-(3-trifluoromethylphenyl)piperazine and methyl 5-chlorosulfonyl-4-methylthiophene-2-carboxylate.

C29H30F3N3O5S2 (621.70), LCMS(ESI): 622.2 (M+H⁺).

EXAMPLE 35

[1-(5-Chloro-3-methylbenzo[b]thiophene-2-sulfonyl)-3,4-trans-4-phenyl-pyrrolidin-3-yl]-[4-(3-trifluoromethylphenyl)piperazin-1-yl]methanone

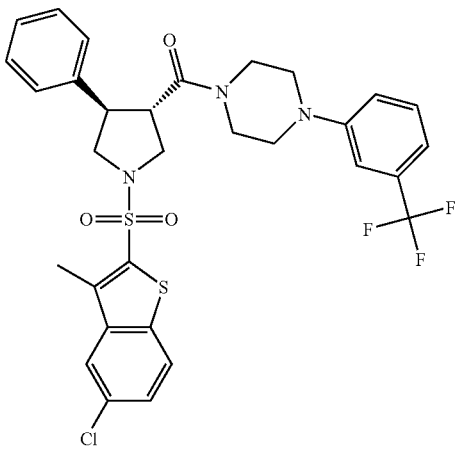

rac

[1-(5-Chloro-3-methylbenzo[b]thiophene-2-sulfonyl)-3,4-trans-4-phenyl-pyrrolidin-3-yl]-[4-(3-trifluoromethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(3-trifluoromethylphenyl)piperazine and 5-chloro-3-methylbenzo[b]thiophene-2-sulfonyl chloride.

C31H29ClF3N3O3S2 (648.17), LCMS(ESI): 648.1 (M+H+).

EXAMPLE 36

[4-(2,4-Dimethylphenyl)piperazin-1-yl]-[3,4-trans-4-phenyl-1-(thiophene-2-sulfonyl)pyrrolidin-3-yl]methanone

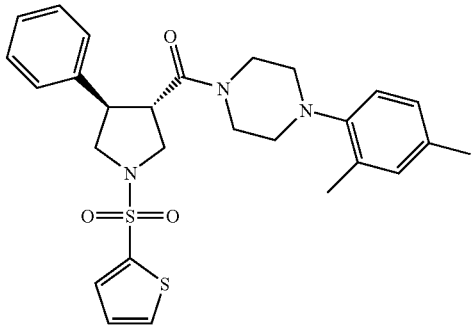

rac

[4-(2,4-Dimethylphenyl)piperazin-1-yl]-[3,4-trans-4-phenyl-1-(thiophene-2-sulfonyl)pyrrolidin-3-yl]methanone is obtained in analogy to example 1 from the commercially available reagents methyl (E)-cinnamate, N-(methoxymethyl)-N-(trimethylsilylmethyl)benzylamine, 1-(2,4-dimethyl-phenyl)piperazine and thiophene-2-sulfonyl chloride.

C27H31N3O3S2 (509.69), LCMS(ESI): 510.2 (M+H+).

EXAMPLE 37

[1-(4,5-Dibromothiophene-2-sulfonyl)-3,4-trans-4-phenylpyrrolidin-3-yl]-[4-(2,4-dimethylphenyl)piperazin-1-yl]methanone

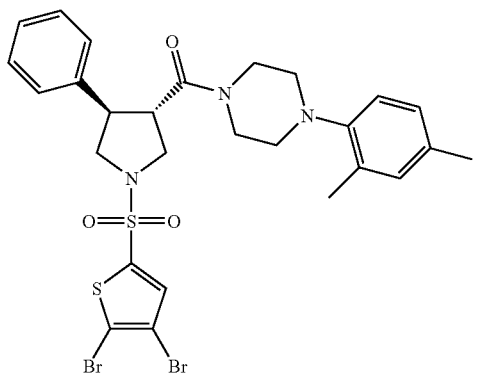

rac

[1-(4,5-Dibromothiophene-2-sulfonyl)-3,4-trans-4-phenylpyrrolidin-3-yl]-[4-(2,4-dimethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(2,4-dimethyl-phenyl)piperazine and 4,5-dibromothiophene-2-sulfonyl chloride.

C27H29Br2N3O3S2 (667.49), LCMS(ESI): 668.0 (M+H+).

EXAMPLE 38

[1-(5-Chlorothiophene-2-sulfonyl)-3,4-trans-4-phenylpyrrolidin-3-yl]-[4-(2,4-dimethylphenyl)piperazin-1-yl]methanone

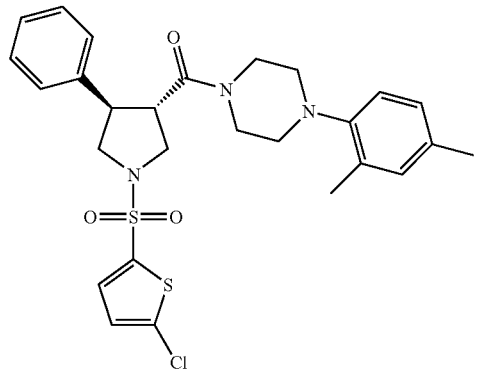

rac

[1-(5-Chlorothiophene-2-sulfonyl)-3,4-trans-4-phenylpyrrolidin-3-yl]-[4-(2,4-dimethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(2,4-dimethyl-phenyl)piperazine and 5-chlorothiophene-2-sulfonyl chloride.

C27H30ClN3O3S2 (544.14), LCMS(ESI): 544.2 (M+H+).

EXAMPLE 39

[1-(4,5-Dichlorothiophene-2-sulfonyl)-3,4-trans-4-phenylpyrrolidin-3-yl]-4-(2,4-dimethylphenyl)piperazin-1-yl]methanone

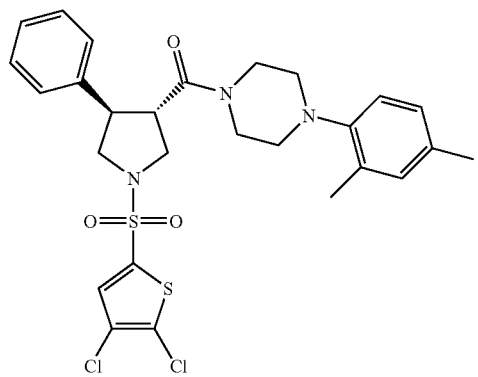

rac

[1-(4,5-Dichlorothiophene-2-sulfonyl)-3,4-trans-4-phenylpyrrolidin-3-yl]-4-(2,4-dimethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(2,4-dimethyl-phenyl)piperazine and 4,5-dichlorothiophene-2-sulfonyl chloride.

C27H29Cl2N3O3S2 (578.58), LCMS(ESI): 578.1 (M+H$^+$).

EXAMPLE 40

Methyl 5-{3,4-trans-3-[4-(2,4-dimethylphenyl)piperazine-1-carbonyl-4-phenylpyrrolidine-1-sulfonyl}-4-methylthiophene-2-carboxylate

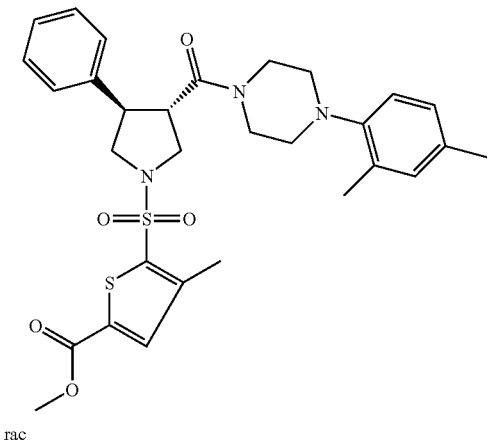

rac

Methyl 5-{3,4-trans-3-[4-(2,4-dimethylphenyl)piperazine-1-carbonyl-4-phenylpyrrolidine-1-sulfonyl}-4-methylthiophene-2-carboxylate is obtained in analogy to example 1 from the commercially available reagents methyl (E)-cinnamate, N-(methoxymethyl)-N-(trimethylsilylmethyl)benzylamine, 1-(2,4-dimethylphenyl)piperazine and methyl 5-chlorosulfonyl-4-methylthiophene-2-carboxylate.

C30H35N3O5S2 (581.76), LCMS(ESI): 582.2 (M+H$^+$).

EXAMPLE 41

[1-(5-Chloro-3-methylbenzo[b]thiophene-2-sulfonyl)-3,4-trans-4-phenyl-pyrrolidin-3-yl]-[4-(2,4-dimethylphenyl)piperazin-1-yl]methanone

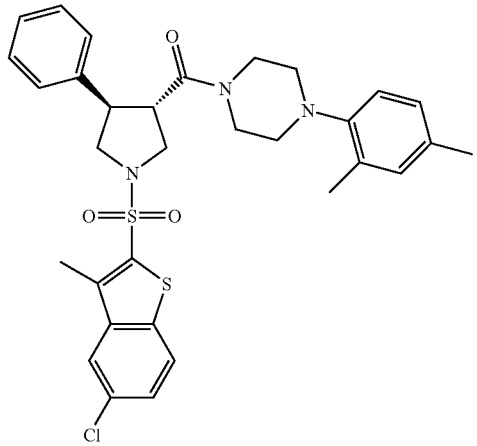

rac

[1-(5-Chloro-3-methylbenzo[b]thiophene-2-sulfonyl)-3,4-trans-4-phenyl-pyrrolidin-3-yl]-[4-(2,4-dimethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(2,4-dimethylphenyl)piperazine and 5-chloro-3-methylbenzo[b]thiophene-2-sulfonyl chloride.

C32H34ClN3O3S2 (608.23), LCMS(ESI): 608.2 (M+H$^+$).

EXAMPLE 42

[4-(3,4-Dimethylphenyl)piperazin-1-yl]-[3,4-trans-4-phenyl-1-(thiophene-2-sulfonyl)pyrrolidin-3-yl)methanone

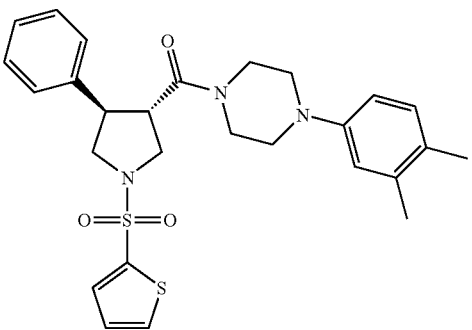

rac

[4-(3,4-Dimethylphenyl)piperazin-1-yl]-[3,4-trans-4-phenyl-1-(thiophene-2-sulfonyl)pyrrolidin-3-yl)methanone is obtained in analogy to example 1 from the commercially available reagents methyl (E)-cinnamate, N-(methoxymethyl)-N-(trimethylsilylmethyl)benzylamine, 1-(3,4-dimethyl-phenyl)piperazine and thiophene-2-sulfonyl chloride.

C27H31N3O3S2 (509.69), LCMS(ESI): 510.1 (M+H$^+$).

EXAMPLE 43

[1-(4,5-Dibromothiophene-2-sulfonyl)-3,4-trans-4-phenylpyrrolidin-3-yl]-[4-(3,4-dimethylphenyl)piperazin-1-yl]methanone

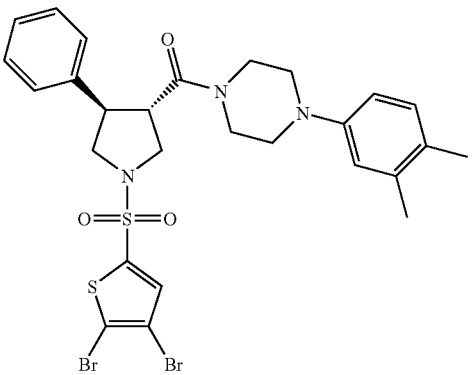

rac

[1-(4,5-Dibromothiophene-2-sulfonyl)-3,4-trans-4-phenylpyrrolidin-3-yl]-[4-(3,4-dimethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(3,4-dimethyl-phenyl)piperazine and 4,5-dibromothiophene-2-sulfonyl chloride.

C27H29Br2N3O3S2 (667.49), LCMS(ESI): 668.0 (M+H$^+$).

EXAMPLE 44

[1-(5-Chlorothiophene-2-sulfonyl)-3,4-trans-4-phenylpyrrolidin-3-yl]-[4-(3,4-dimethylphenyl)piperazin-1-yl]methanone

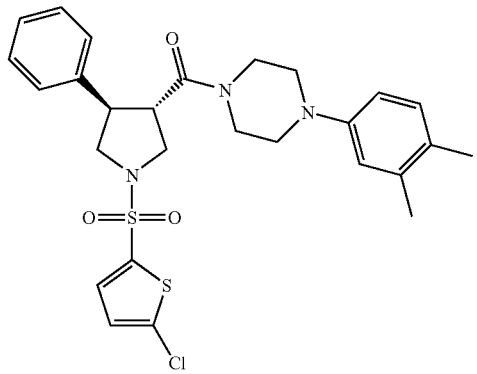

rac

[1-(5-Chlorothiophene-2-sulfonyl)-3,4-trans-4-phenylpyrrolidin-3-yl]-[4-(3,4-dimethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(3,4-dimethyl-phenyl)piperazine and 5-chlorothiophene-2-sulfonyl chloride.

C27H30ClN3O3S2 (544.14), LCMS(ESI): 544.1 (M+H$^+$).

EXAMPLE 45

[1-(4,5-Dichlorophene-2-sulfonyl)-3,4-trans-4-phenylpyrrolidin-3-yl]-4-(3,4-dimethylphenyl)piperazin-1-yl]methanone

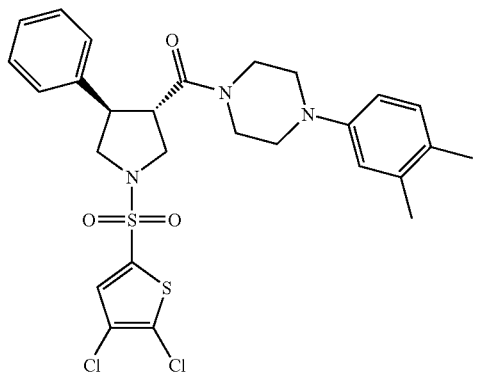

rac

[1-(4,5-Dichlorophene-2-sulfonyl)-3,4-trans-4-phenylpyrrolidin-3-yl]-4-(3,4-dimethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(3,4-dimethylphenyl)piperazine and 4,5-dichlorothiophene-2-sulfonyl chloride.

C27H29Cl2N3O3S2 (578.58), LCMS(ESI): 578.1 (M+H$^+$).

EXAMPLE 46

Methyl 5-{3,4-trans-3-[4-(3,4-dimethylphenyl)piperazine-1-carbonyl]-4-phenylpyrrolidine-1-sulfonyl}-4-methylthiophene-2-carboxylate

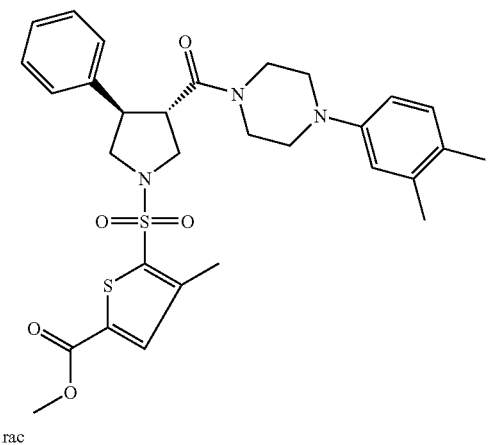

rac

Methyl 5-{3,4-trans-3-[4-(3,4-dimethylphenyl)piperazine-1-carbonyl]-4-phenylpyrrolidine-1-sulfonyl}-4-methylthiophene-2-carboxylate is obtained in analogy to example 1 from the commercially available reagents methyl (E)-cinnamate, N-(methoxymethyl)-N-(trimethylsilylmethyl)benzylamine, 1-(3,4-dimethylphenyl)piperazine and methyl 5-chlorosulfonyl-4-methylthiophene-2-carboxylate.

C30H35N3O5S2 (581.76), LCMS(ESI): 582.2 (M+H$^+$).

EXAMPLE 47

[1-(5-Chloro-3-methylbenzo[b]thiophene-2-sulfonyl)-3,4-trans-4-phenyl-pyrrolidin-3-yl]-[4-(3,4-dimethylphenyl)piperazin-1-yl]methanone

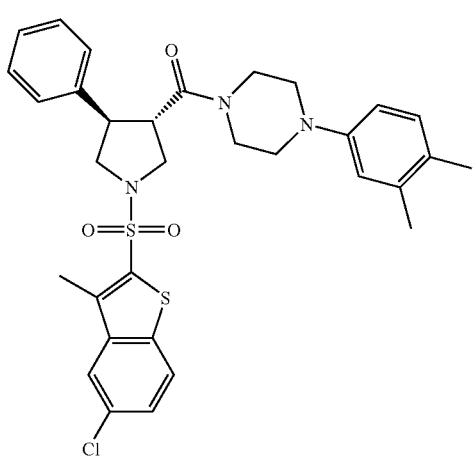

rac

[1-(5-Chloro-3-methylbenzo[b]thiophene-2-sulfonyl)-3,4-trans-4-phenyl-pyrrolidin-3-yl]-[4-(3,4-dimethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(3,4-dimethylphenyl)piperazine and 5-chloro-3-methylbenzo[b]thiophene-2-sulfonyl chloride.

C32H34ClN3O3S2 (608.23, LCMS(ESI): 608.2 (M+H+).

EXAMPLE 48

[1-(5-Chlorothiophen-2-sulfonyl)-3,4-trans-4-phenylpyrrolidin-3-yl]-[4-(2,5-dimethylphenyl)piperazin-1-yl]methanone

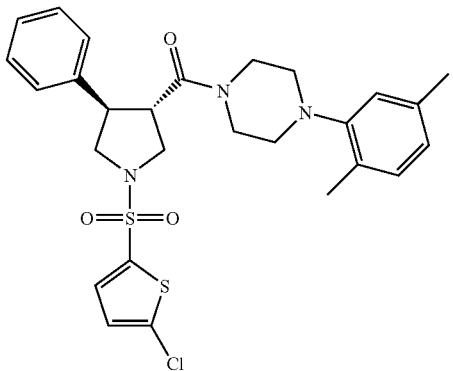

rac

[1-(5-Chlorothiophen-2-sulfonyl)-3,4-trans-4-phenylpyrrolidin-3-yl]-[4-(2,5-dimethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(2,5-dimethylphenyl)piperazine and 5-chlorothiophene-2-sulfonyl chloride.

C27H30ClN3O3S2 (544.14), LCMS(ESI): 544.1 (M+H+).

EXAMPLE 49

[1-(4,5-Dichlorothiophene-2-sulfonyl)-3,4-trans-4-phenylpyrrolidin-3-yl]-[4-(2,5-dimethylphenyl)piperazin-1-yl]methanone

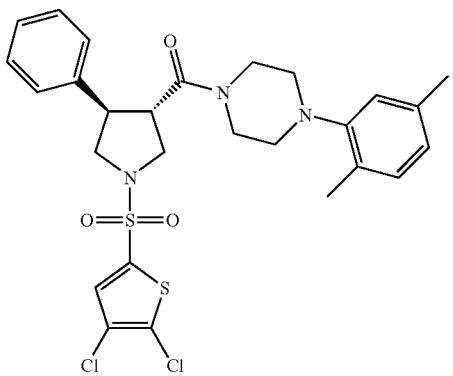

rac

[1-(4,5-Dichlorothiophene-2-sulfonyl)-3,4-trans-4-phenylpyrrolidin-3-yl]-[4-(2,5-dimethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(2,5-dimethyl-phenylpiperazine and 4,5-dichlorothiophene-2-sulfonyl chloride.

C27H29C12N3O3S2 (578.58), LCMS(ESI): 578.1 (M+H+).

EXAMPLE 50

Methyl 5-{3,4-trans-3-[4-(2,5-dimethylphenyl)piperazine-1-carbonyl]-4-phenylpyrrolidine-1-sulfonyl}-4-methylthiophene-2-carboxylate

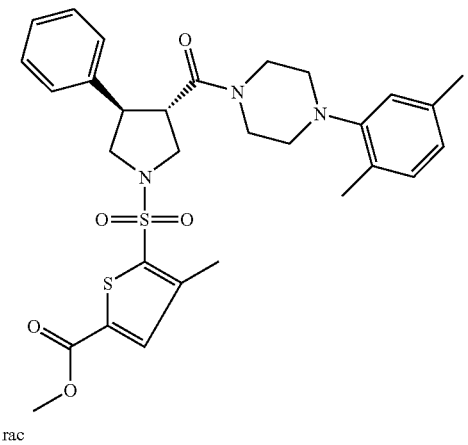

rac

Methyl 5-{3,4-trans-3-[4-(2,5-dimethylphenyl)piperazine-1-carbonyl]-4-phenylpyrrolidine-1'-sulfonyl}-4-methylthiophene-2-carboxylate is obtained in analogy to example 1 from the commercially available reagents methyl (E)-cinnamate, N-(methoxymethyl)-N-(trimethylsilylmethyl)benzylamine, 1-(2,5-dimethylphenyl)piperazine and methyl 5-chlorosulfonyl-4-methylthiophene-2-carboxylate.

C30H35N3O5S3 (581.76), LCMS(ESI): 582.2 (M+H+).

EXAMPLE 51

[1-(5-Chloro-3-methylbenzo[b]thiophene-2-sulfonyl)-3,4-trans-4-phenyl-pyrrolidin-3-yl]-[4-(2,5-dimethylphenyl)piperazin-1-yl]methanone

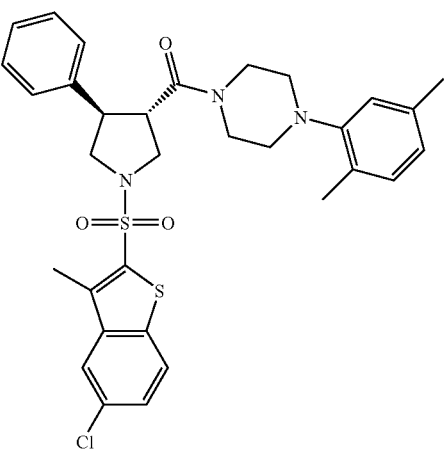

rac

[1-(5-Chloro-3-methylbenzo[b]thiophene-2-sulfonyl)-3,4-trans-4-phenyl-pyrrolidin-3-yl]-[4-(2,5-dimethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(2,5-dimethylphenyl)piperazine and 5-chloro-3-methylbenzo[b]thiophene-2-sulfonyl chloride.

C32H34ClN3O3S2 (608.23), LCMS(ESI): 608.2 (M+H+).

EXAMPLE 52

[4-(2,3-Dimethylphenyl)piperazin-1-yl]-3,4-trans-4-phenyl-1-(thiophene-2-sulfonyl)pyrrolidin-3-yl]methanone

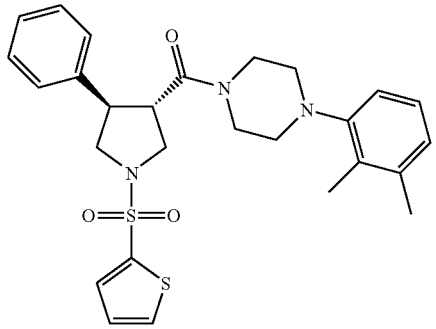

rac

[4-(2,3-Dimethylphenyl)piperazin-1-yl]-3,4-trans-4-phenyl-1-(thiophene-2-sulfonyl)pyrrolidin-3-yl]methanone is obtained in analogy to example 1 from the commercially available reagents methyl (E)-cinnamate, N-(methoxymethyl)-N-(trimethylsilylmethyl)benzylamine, 1-(2,3-dimethyl-phenyl)piperazine and thiophene-2-sulfonyl chloride.

C27H31N3O3S2 (509.69), LCMS(ESI): 510.2 (M+H+).

EXAMPLE 53

[1-(4,5-Dibromothiophene-2-sulfonyl)-3,4-trans-4-phenylpyrrolidin-3-yl]-[4-(2,3-dimethylphenyl)piperazin-1-yl]methanone

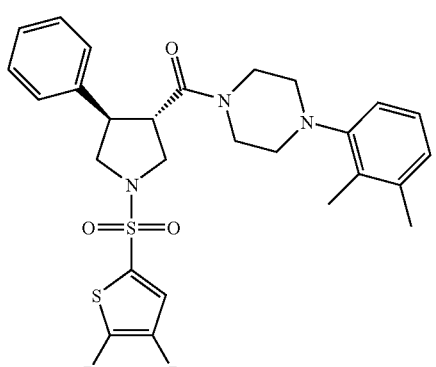

rac

[1-(4,5-Dibromothiophene-2-sulfonyl)-3,4-trans-4-phenylpyrrolidin-3-yl]-[4-(2,3-dimethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(2,3-dimethyl-phenyl)piperazine and 4,5-dibromothiophene-2-sulfonyl chloride.

C27H29Br2N3O3S2 (667.49), LCMS(ESI): 668.1 (M+H+).

EXAMPLE 54

[1-(5-Chlorothiophene-2-sulfonyl)-3,4-trans-4-phenylpyrrolidin-3-yl]-[4-(2,3-dimethylphenyl)piperazin-1-yl]methanone

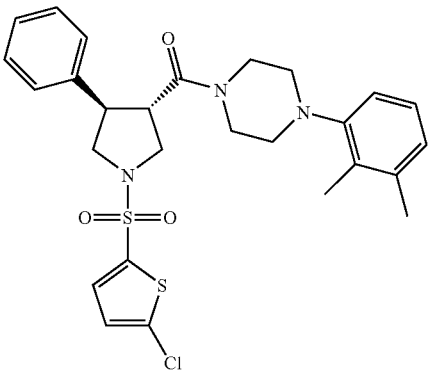

rac

[1-(5-Chlorothiophene-2-sulfonyl)-3,4-trans-4-phenylpyrrolidin-3-yl]-[4-(2,3-dimethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(2,3-dimethyl-phenyl)piperazine and 5-chlorothiophene-2-sulfonyl chloride.

C27H30ClN3O3S2 (544.14), LCMS(ESI): 544.2 (M+H+).

EXAMPLE 55

[1-(4,5-Dichlorothiophene-2-sulfonyl)-3,4-trans-4-phenylpyrrolidin-3-yl]-[4-(2,3-dimethylphenyl)piperazin-1-yl]methanone

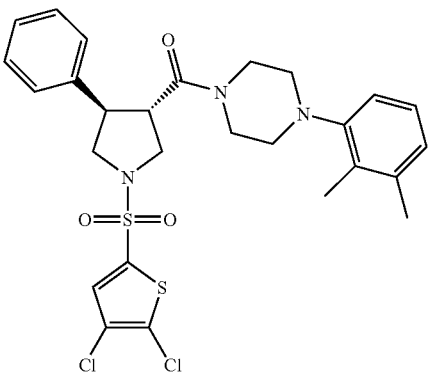

rac

[1-(4,5-Dichlorothiophene-2-sulfonyl)-3,4-trans-4-phenylpyrrolidin-3-yl]-[4-(2,3-dimethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(2,3-dimethylphenyl)piperazine and 4,5-dichlorothiophene-2-sulfonyl chloride.

C27H29Cl2N3O3S2 (578.58), LCMS(ESI): 578.1 (M+H$^+$).

EXAMPLE 56

Methyl 5-{3,4-trans-3-[4-(2,3-dimethylphenyl)piperazine-1-carbonyl]-4-phenylpyrrolidine-1-sulfonyl}-4-methylthiophene-2-carboxylate

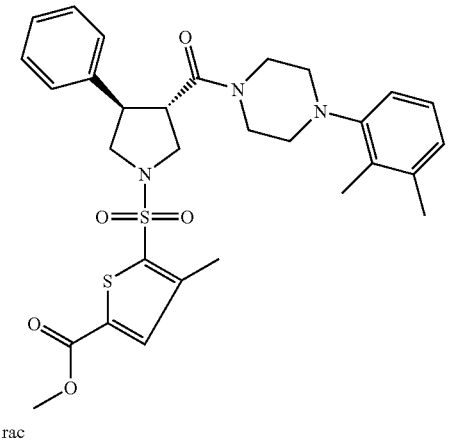

rac

Methyl 5-{3,4-trans-3-[4-(2,3-dimethylphenyl)piperazine-1-carbonyl]-4-phenylpyrrolidine-1-sulfonyl}-4-methylthiophene-2-carboxylate is obtained in analogy to example 1 from the commercially available reagents methyl (E)-cinnamate, N-(methoxymethyl)-N-(trimethylsilylmethyl)benzylamine, 1-(2,3-dimethylphenyl)piperazine and methyl 5-chlorosulfonyl-4-methyl-thiophene-2-carboxylate.

C30H35N3O5S2 (581.76), LCMS(ESI): 582.2 (M+H$^+$).

EXAMPLE 57

[1-(5-Chloro-3-methylbenzo[b]thiophene-2-sulfonyl)-3,4-trans-4-phenyl-pyrrolidin-3-yl]-[4-(2,3-dimethylphenyl)piperazin-1-yl]methanone

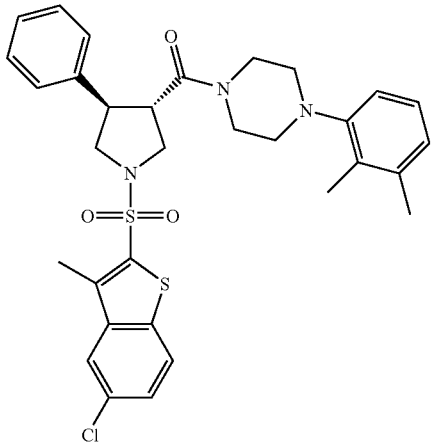

rac

[1-(5-Chloro-3-methylbenzo[b]thiophene-2-sulfonyl)-3,4-trans-4-phenyl-pyrrolidin-3-yl]-[4-(2,3-dimethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(2,3-dimethylphenyl)piperazine and 5-chloro-3-methylbenzo[b]thiophene-2-sulfonyl chloride.

C32H34ClN3O3S2 (608.23), LCMS(ESI): 608.2 (M+H$^+$).

EXAMPLE 58

[4-(4-Methoxyphenyl)piperazin-1-yl]-[3,4-trans-4-phenyl-1-(thiophene-2-sulfonyl)pyrrolidin-3-yl]methanone

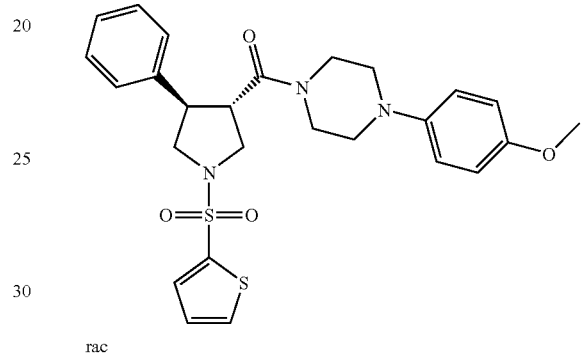

rac

[4-(4-Methoxyphenyl)piperazin-1-yl]-[3,4-trans-4-phenyl-1-(thiophene-2-sulfonyl)pyrrolidin-3-yl]methanone is obtained in analogy to example 1 from the commercially available reagents methyl (E)-cinnamate, N-(methoxymethyl)-N-(trimethylsilylmethyl)benzylamine, 1-(4-methoxyphenyl)piperazine and thiophene-2-sulfonyl chloride.

C26H29N3O4S2 (511.67) LCMS(ESI): 512.1 (M+H$^+$).

EXAMPLE 59

1-(4,5-Dibromothiophene-2-sulfonyl)-3,4-trans-4-phenylpyrrolidin-3-yl]-[4-(4-methoxyphenyl)piperazin-1-yl]methanone

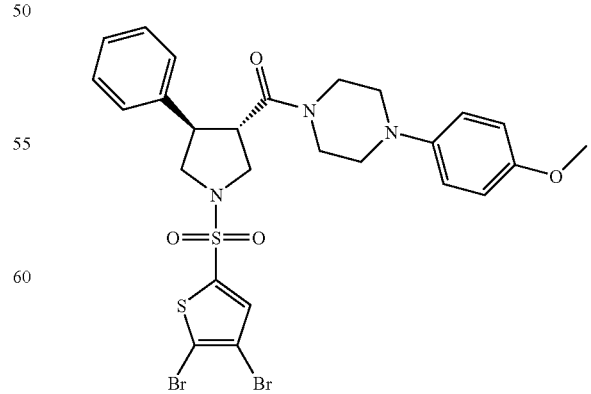

rac 1-(4,5-Dibromothiophene-2-sulfonyl)-3,4-trans-4-phenylpyrrolidin-3-yl]-[4-(4-methoxyphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(4-methoxy-phenyl)piperazine and 4,5-dibromothiophene-2-sulfonyl chloride.

C26H27Br2N3O4S2 (669.46), LCMS(ESI): 669.9 (M+H+).

EXAMPLE 60

[1-(5-Chlorothiophene-2-sulfonyl)-3,4-trans-4-phenylpyrrolidin-3-yl]-[4-(4-methoxyphenyl)piperazin-1-yl]methanone

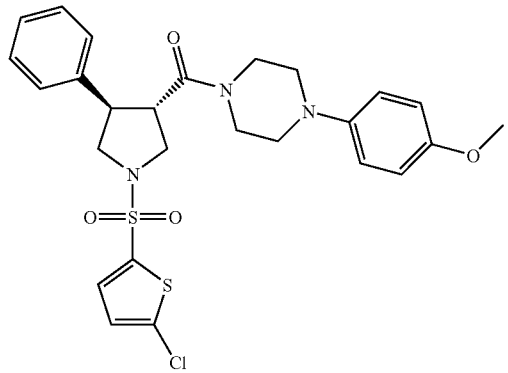

rac

[1-(5-Chlorothiophene-2-sulfonyl)-3,4-trans-4-phenylpyrrolidin-3-yl]-[4-(4-methoxyphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(4-methoxy-phenyl)piperazine and 5-chlorothiophene-2-sulfonyl chloride.

C26H28ClN3O4S2 (546.11), LCMS(ESI): 546.1 (M+H+).

EXAMPLE 61

[1-(4,5-Dichlorothiophene-2-sulfonyl)-3,4-trans-4-phenylpyrrolidin-3-yl]-[4-(4-methoxyphenyl)piperazin-1-yl]methanone

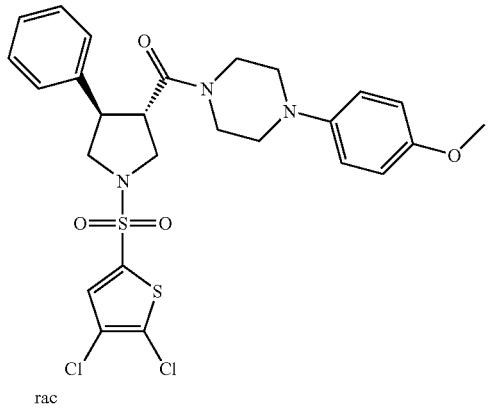

rac

[1-(4,5-Dichlorothiophene-2-sulfonyl)-3,4-trans-4-phenylpyrrolidin-3-yl]-[4-(4-methoxyphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(4-methoxy-phenyl)piperazine and 4,5-dichlorothiophene-2-sulfonyl chloride.

C26H27Cl2N3O4S2 (580.56), LCMS(ESI): 580.0 (M+H+)

EXAMPLE 62

Methyl [5-{3,4-trans-3-[4-(4-methoxyphenyl)piperazine-1-carbonyl]-4-phenylpyrrolidine-1-sulfonyl}-4-methylthiophene-2-carboxylate

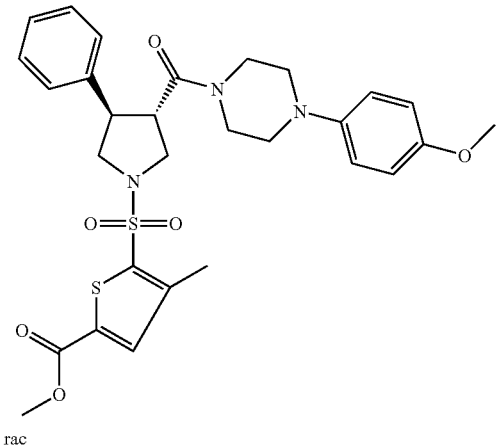

rac

Methyl [5-{3,4-trans-3-[4-(4-methoxyphenyl)piperazine-1-carbonyl]-4-phenylpyrrolidine-1-sulfonyl}-4-methylthiophene-2-carboxylate is obtained in analogy to example 1 from the commercially available reagents methyl (E)-cinnamate, N-(methoxymethyl)-N-(trimethylsilylmethyl)benzylamine, 1-(4-methoxyphenyl)piperazine and methyl 5-chlorosulfonyl-4-methylthiophene-2-carboxylate.

C29H33N3O6S2 (583.73), LCMS(ESI): 584.1 (M+H+).

EXAMPLE 63

[1-(5-Chloro-3-methylbenzo[b]thiophene-2-sulfonyl)-3,4-trans-4-phenyl-pyrrolidin-3-yl]-[4-(4-methoxyphenyl)piperazin-1-yl]methanone

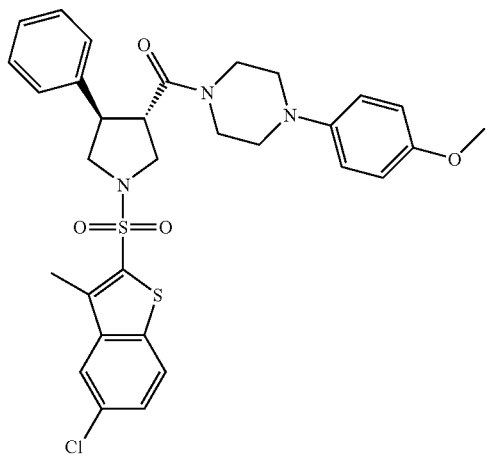

rac

[1-(5-Chloro-3-methylbenzo[b]thiophene-2-sulfonyl)-3,4-trans-4-phenyl-pyrrolidin-3-yl]-[4-(4-methoxyphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(4-methoxyphenyl)piperazine and 5-chloro-3-methylbenzo[b]thiophene-2-sulfonyl chloride.

C31H32ClN3O4S2 (610.20), LCMS(ESI): 610.1 (M+H⁺).

EXAMPLE 64

[1-(4,5-Dibromothiophene-2-sulfonyl)-3,4-trans-4-phenylpyrrolidin-3-yl]-(4-phenylpiperazin-1-yl)methanone

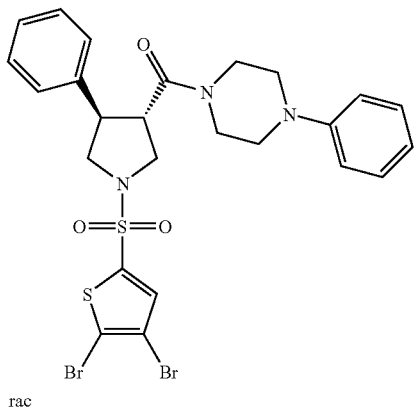

rac

[1-(4,5-Dibromothiophene-2-sulfonyl)-3,4-trans-4-phenylpyrrolidin-3-yl]-(4-phenylpiperazin-1-yl)methanone is obtained in analogy to example 1 from the commercially available reagents methyl (E)-cinnamate, N-(methoxymethyl)-N-(trimethylsilylmethyl)benzylamine, 1-phenylpiperazine and 4,5-dibromothiophene-2-sulfonyl chloride.

C25H25Br2N3O3S2 (639.43), LCMS(ESI): 640.0 (M+H⁺).

EXAMPLE 65

Dimethyl 2-{4-[3,4-trans-4-phenyl-1-(thiophene-2-sulfonyl)pyrrolidine-3-carbonyl]piperazin-1-yl}terephthalate trifluoroacetate

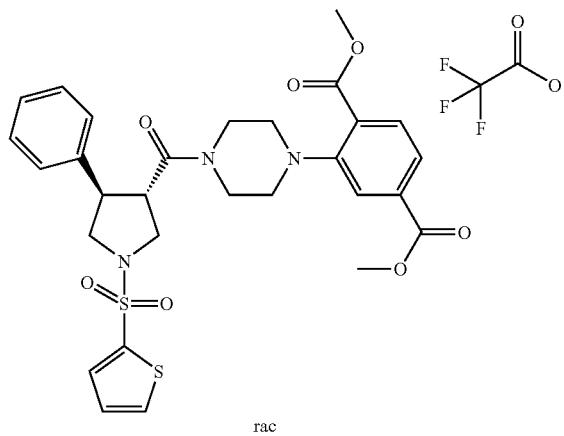

rac

Dimethyl 2-{4-[3,4-trans-4-phenyl-1-(thiophene-2-sulfonyl)pyrrolidine-3-carbonyl]piperazin-1-yl}terephthalate trifluoroacetate is obtained in analogy to example 1 from dimethyl 2-piperazin-1-ylterephthalate and the commercially available reagents methyl (E)-cinnamate, N-(methoxymethyl)-N-(trimethylsilylmethyl)benzylamine and thiophene-2-sulfonyl chloride.

C29H31N3O7S2.C2HF3O2 (711.73), LCMS(ESI): 597.9 (M+H⁺).

EXAMPLE 66

[4-(2,5-Dichlorophenyl)piperazin-1-yl]-[3,4-trans-4-phenyl-1-(thiophene-2-sulfonyl)pyrrolidin-3-yl]methanone trifluoroacetate

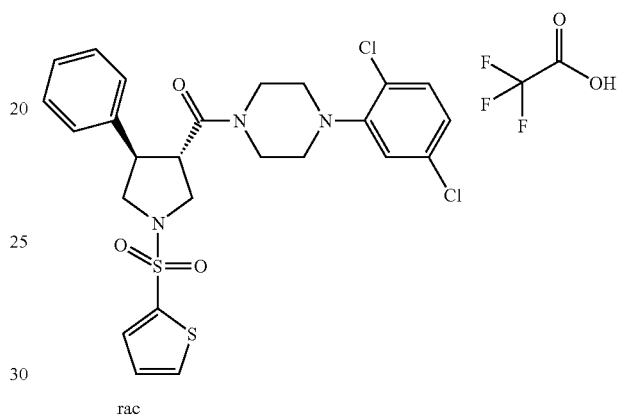

rac

[4-(2,5-Dichlorophenyl)piperazin-1-yl]-[3,4-trans-4-phenyl-1-(thiophene-2-sulfonyl)pyrrolidin-3-yl]methanone trifluoroacetate is obtained in analogy to example 1 from the commercially available reagents methyl (E)-cinnamate, N-(methoxymethyl)-N-(trimethylsilylmethyl)benzylamine, 1-(2,5-dichlorophenylpiperazine and thiophene-2-sulfonyl chloride.

C25H25Cl2N3O3S2.C2HF3O2 (664.55), LCMS(ESI): 550.0 (M+H⁺).

EXAMPLE 67

[4-(2,5-Dimethylphenyl)piperazin-1-yl]-[3,4-trans-4-phenyl-1-(thiophene-2-sulfonyl)pyrrolidin-3-yl]methanone

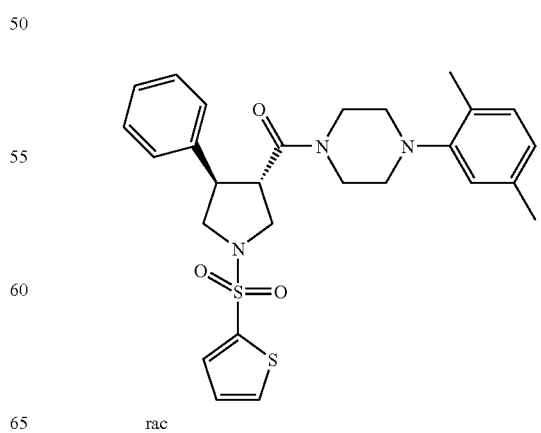

rac

[4-(2,5-Dimethylphenyl)piperazin-1-yl]-[3,4-trans-4-phenyl-1-(thiophene-2-sulfonyl)pyrrolidin-3-yl]methanone is obtained in analogy to example 1 from the commercially available reagents methyl (E)-cinnamate, N-(methoxymethyl)-N-(trimethylsilylmethyl)benzylamine, 1-(2,5-dimethyl-phenyl)piperazine and thiophene-2-sulfonyl chloride.

27H31N3O3S2 (509.69), LCMS(ESI): 510.3 (M+H+).

The racemate of [4-(2,5-dimethylphenyl)piperazin-1-yl]-[3,4-trans-4-phenyl-1-(thiophene-2-sulfonyl)pyrrolidin-3-yl]methanone was fractionated into the enantiomers by chiral phase chromatography. [4-(2,5-Dimethylphenyl)-piperazin-1-yl]-[(3S,4R)/(3R,4S)-4-phenyl-1-(thiophene-2-sulfonyl)-pyrrolidin-3-yl]methanone Example 67A (Chiracel OJ/37 250×4.6 mm, eluent methanol, Rt=8.4 min) and [4-(2,5-dimethylphenyl)piperazin-1-yl]-[(3R,4S)/(3S,4R)-4-phenyl-1-(thiophene-2-sulfonyl)pyrrolidin-3-yl]-methanone Example 67B (Chiracel OJ/37 250×4.6 mm, eluent methanol, Rt=10.3 min) are obtained.

EXAMPLE 68

[1-(Benzene[1,2,5-oxadiazol-4-sulfonyl)-3,4-trans-4-phenylpyrrolidin-3-yl]-[4-(2,5-dimethylphenyl)piperazin-1-yl]methanone trifluoroacetate

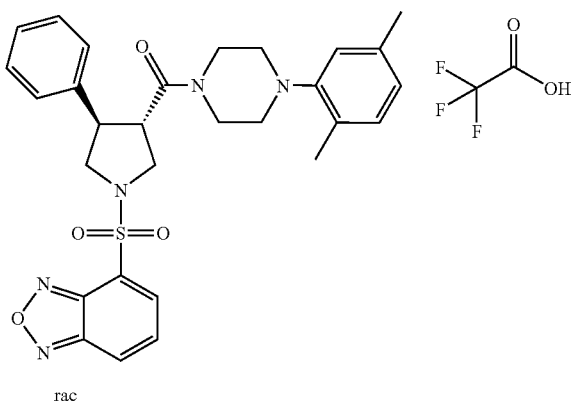

rac

[1-(Benzene[1,2,5-oxadiazol-4-sulfonyl)-3,4-trans-4-phenylpyrrolidin-3-yl]-[4-(2,5-dimethylphenyl)piperazin-1-yl]methanone trifluoroacetate is obtained in analogy to example 1 from the commercially available reagents methyl (E)-cinnamate, N-(methoxymethyl)-N-(trimethylsilylmethyl)-benzylamine, 1-(2,5-dimethylphenyl)piperazine and benzo[1,2,5]oxadiazole-4-sulfonyl chloride.

C29H31N5O4S.C2HF3O2 (659.69), LCMS(ESI): 546.1 (M+H+).

EXAMPLE 69

[4-(2,5-Dimethylphenyl)piperazin-1-yl]-[1-(3-methoxybenzenesulfonyl)-3,4-trans-4-phenylpyrrolidin-3-yl]methanone

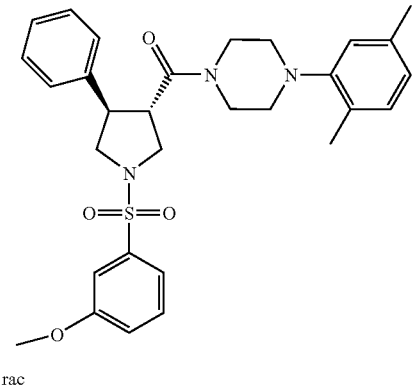

rac

[4-(2,5-Dimethylphenyl)piperazin-1-yl]-[1-(3-methoxybenzenesulfonyl)-3,4-trans-4-phenylpyrrolidin-3-yl]methanone is obtained in analogy to example 1 from the commercially available reagents methyl (E)-cinnamate, N-(methoxymethyl)-N-(trimethylsilylmethyl)benzylamine, 1-(2,5-dimethylphenyl)piperazine and 3-methoxybenzenesulfonyl chloride.

C30H35N3O4S (533.70), LCMS(ESI): 534.2 (M+H+).

The racemate of [4-(2,5-dimethylphenyl)piperazin-1-yl]-[1-(3-methoxy-benzenesulfonyl)-3,4-trans-4-phenylpyrrolidin-3-yl]methanone was fractionated into the enantiomers by chiral phase chromatography. [4-(2,5-Dimethylphenyl)piperazin-1-yl]-[1-(3-methoxybenzenesulfonyl)-(3S,4R)/(3R,4S)-4-phenylpyrrolidin-3-yl]methanone Example 69A (Chirapak AD-22 250×4.6 mm, eluent ethanol:methanol=1:1, Rt=7.6 min) and [4-(2,5-dimethylphenyl)piperazin-1-yl]-[1-(3-methoxybenzenesulfonyl)-(3R,4S)/(3S,4R)-4-phenylpyrrolidin-3-yl]methanone Example 69B (Chirapak AD-22 250×4.6 mm, eluent ethanol:methanol=1:1, Rt=13.6 min) are obtained.

EXAMPLE 70

[4-(2,5-Dimethylphenyl)piperazin-1-yl]-[3,4-trans-4-phenyl-1-(propan-2-sulfonyl)pyrrolidin-3-yl]methanone trifluoroacetate

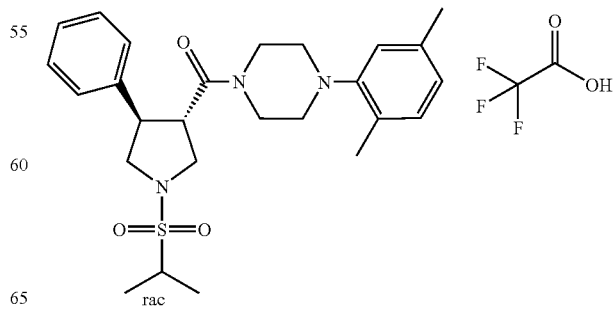

rac

[4-(2,5-Dimethylphenyl)piperazin-1-yl]-[3,4-trans-4-phenyl-1-(propane-2-sulfonyl)pyrrolidin-3-yl]methanone trifluoroacetate is obtained in analogy to example 1 from the commercially available reagents methyl (E)-cinnamate, N-(methoxymethyl)-N-(trimethylsilylmethyl)benzylamine, 1-(2,5-dimethyl-phenyl)piperazine and isopropylsulfonyl chloride.

C26H35N3O3S.C2HF3O2 (583.68), LCMS(ESI): 470.2 (M+H$^+$).

EXAMPLE 71

[1-(3,5-Dimethylisoxazole-4-sulfonyl)-3,4-trans-4-phenylpyrrolidin-3-yl]-[4-(2,5-dimethylphenyl)piperazin-1-yl]methanone

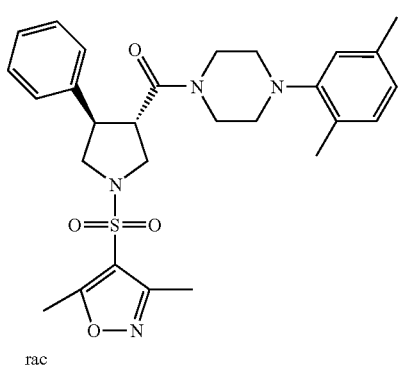

[1-(3,5-Dimethyl isoxazole-4-sulfonyl)-3,4-trans-4-phenylpyrrolidin-3-yl]-[4-(2,5-dimethylphenyl)piperazin-1-yl]methanone is obtained in analogy to example 1 from the commercially available reagents methyl (E)-cinnamate, N-(methoxymethyl)-N-(trimethylsilylmethyl)benzylamine, 1-(2,5-dimethyl-phenyl)piperazine and 3,5-dimethylisoxazole-4-sulfonyl chloride.

C28H34N4O4S (522.67), LCMS(ESI): 523.3 (M+H$^+$).

The racemate of [1-(3,5-dimethylisoxazole-4-sulfonyl)-3,4-trans-4-phenyl-pyrrolidin-3-yl]-[4-(2,5-dimethylphenyl)piperazin-1-yl]methanone was fractionated into the enantiomers by chiral phase chromatography. [1-(3,5-Dimethylisoxazole-4-sulfonyl)-(3S,4R/(3R,4S)-phenylpyrrolidin-3-yl]-[4-(2,5-dimethylphenyl)piperazin-1-yl]methanone example 71A (Chirapak AD-22 250×4.6 mm, eluent ethanol:methanol=1:1, Rt=6.5 min) and [1-(3,5-dimethylisoxazol-4-sulfonyl)-(3R,4S)/(3S,4R)-4-phenylpyrrolidin-3-yl]-[4-(2,5-dimethylphenyl)piperazin-1-yl]methanone example 71B (Chirapak AD-22 250×4.6 mm, eluent ethanol:methanol=1:1, Rt=9.1 min) are obtained.

EXAMPLE 72

[4-(2,5-Dimethylphenyl)piperazin-1-yl]-[3,4-trans-4-phenyl-1-(pyridine-3-sulfonyl)pyrrolidin-3-yl]methanone trifluoroacetate

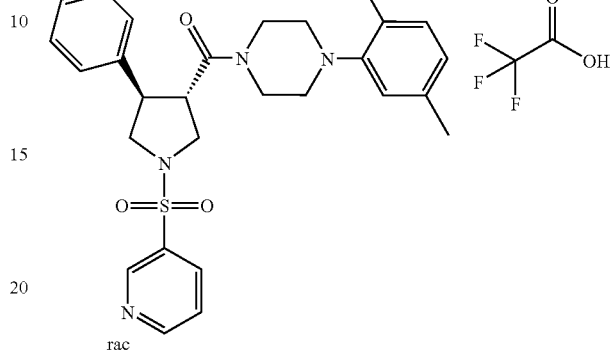

[4-(2,5-Dimethylphenyl)piperazin-1-yl]-[3,4-trans-4-phenyl-1-(pyridine-3-sulfonyl)pyrrolidin-3-yl]methanone trifluoroacetate is obtained in analogy to example 1 from the commercially available reagents methyl (E)-cinnamate, N-(methoxymethyl)-N-(trimethylsilylmethyl)benzylamine, 1-(2,5-dimethyl-phenyl)piperazine and pyridine-3-sulfonyl chloride.

C28H32N4O3S.2C2HF3O2 (732.70), LCMS(ESI): 505.1 (M+H$^+$).

EXAMPLE 73

[4-(2,5-Dichlorophenyl)piperazin-1-yl]-[3,4-trans-4-phenyl-1-(pyridine-3-sulfonyl)pyrrolidin-3-yl]methanone trifluoroacetate

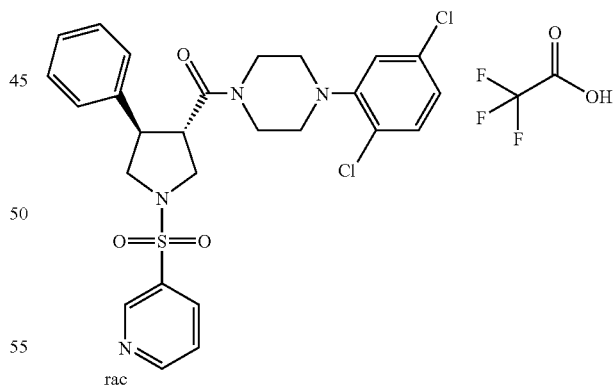

[4-(2,5-Dichlorophenyl)piperazin-1-yl]-[3,4-trans-4-phenyl-1-(pyridine-3-sulfonyl)pyrrolidin-3-yl]methanone trifluoroacetate is obtained in analogy to example 1 from the commercially available reagents methyl (E)-cinnamate, N-(methoxymethyl)-N-(trimethylsilylmethyl)benzylamine, 1-(2,5-dichloro-phenyl)piperazine and pyridine-3-sulfonyl chloride.

C26H26Cl2N4O3S.2C2HF3O2 (773.54), LCMS(ESI): 545.0 (M+H$^+$).

EXAMPLE 74

[4-(2,5-Dichlorophenyl)piperazin-1-yl]-[3,4-trans-4-phenyl-1-(toluene-3-sulfonyl)pyrrolidin-3-yl]methanone trifluoroacetate

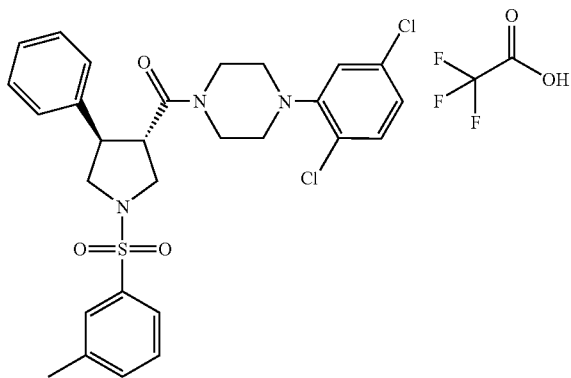

[4-2,5-Dichlorophenyl)piperazin-1-yl]-[3,4-trans-4-phenyl-1-(toluene-3-sulfonyl)pyrrolidin-3-yl]methanone trifluoroacetate is obtained in analogy to example 1 from the commercially available reagents methyl (E)-cinnamate, N-(methoxymethyl)-N-(trimethylsilylmethyl)benzylamine, 1-(2,5-dichlorophenyl)piperazine and 3-methylbenzenesulfonyl chloride.

C28H29Cl2N3O3S.C2HF3O2 (672.56), LCMS(ESI): 558.2 (M+H+).

EXAMPLE 75

[4-(2,5-Dichlorophenyl)piperazin-1-yl]-[1-(4-methoxybenzenesulfonyl)-3,4-trans-4-phenyl pyrrolidin-3-yl]methanone trifluoroacetate

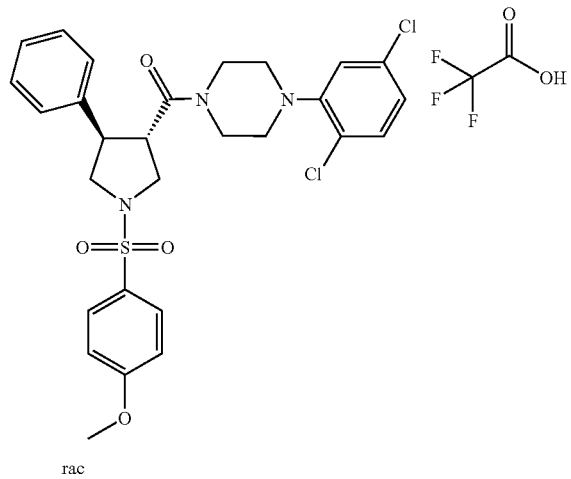

[4-(2,5-Dichlorophenyl)piperazin-1-yl]-[1-(4-methoxybenzenesulfonyl)-3,4-trans-4-phenylpyrrolidin-3-yl]methanone trifluoroacetate is obtained in analogy to example 1 from the commercially available reagents methyl (E)-cinnamate, N-(methoxymethyl)-N-(trimethylsilylmethyl)benzylamine, 1-(2,5-dichlorophenyl)piperazine and 4-methoxybenzenesulfonyl chloride.

C28H29Cl2N3O4S.C2HF3O2 (688.56), LCMS(ESI): 574.2 (M+H+).

EXAMPLE 76

[4-(2,5-Dimethoxyphenyl)piperazin-1-yl]-[3,4-trans-4-phenyl-1-(2,2,2-trifluoroethanesulfonyl)pyrrolidin-3-yl]methanone trifluoroacetate

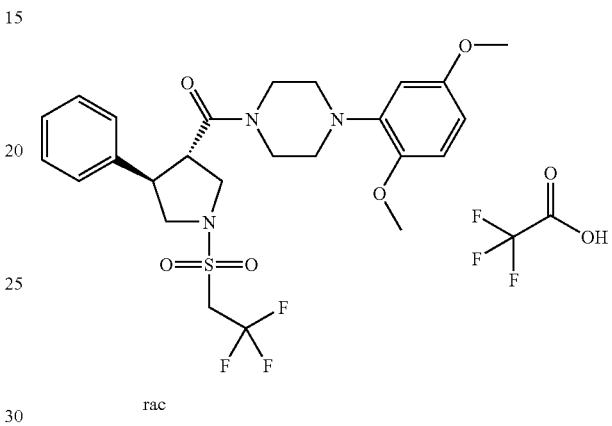

[4-(2,5-Dimethoxyphenyl)piperazin-1-yl]-[3,4-trans-4-phenyl-1-(2,2,2-trifluoroethanesulfonyl)pyrrolidin-3-yl]methanone trifluoroacetate is obtained in analogy to example 1 from the commercially available reagents methyl (E)-cinnamate, N-(methoxymethyl)-N-(trimethylsilylmethyl)benzylamine, 1-(2,5-dimethoxyphenyl)piperazine and 2,2,2-trifluoroethanesulfonyl chloride.

C25H30F3N3O5S.C2HF3O2 (655.62), LCMS(ESI): 542.3 (M+H+).

EXAMPLE 77

[4-(2,5-Dimethoxyphenyl)piperazin-1-yl]-[3,4-trans-4-phenyl-1-(pyridine-3-sulfonyl)pyrrolidin-3-yl]methanone trifluoroacetate

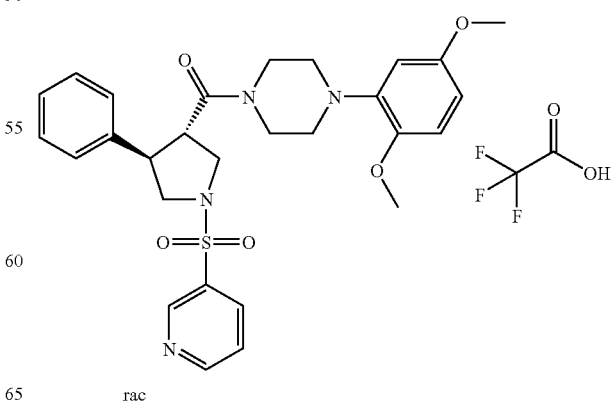

[4-(2,5-Dimethoxyphenyl)piperazin-1-yl]-[3,4-trans-4-phenyl-1-(pyridine-3-sulfonyl)pyrrolidin-3-yl]methanone trifluoroacetate is obtained in analogy to example 1 from the commercially available reagents methyl (E)-cinnamate, N-(methoxymethyl)-N-(trimethylsilylmethyl)benzylamine, 1-(2,5-dimethoxyphenyl)piperazine and pyridine-3-sulfonyl chloride.

C28H32N4O5S.2C2HF3O2 (764.70), LCMS(ESI): 537.3 (M+H+).

EXAMPLE 78

[4-(2,5-Dimethoxyphenyl)piperazin-1-yl]-[3,4-trans-4-phenyl-1-(propane-2-sulfonyl)pyrrolidin-3-yl]methanone trifluoroacetate

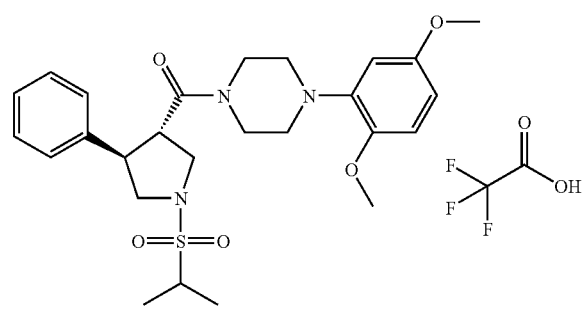

rac

[4-(2,5-Dimethoxyphenyl)piperazin-1-yl]-[3,4-trans-4-phenyl-1-(propane-2-sulfonyl)pyrrolidin-3-yl]methanone trifluoroacetate is obtained in analogy to example 1 from the commercially available reagents methyl (E)-cinnamate, N-(methoxymethyl)-N-(trimethylsilylmethyl)benzylamine, 1-(2,5-dimethoxyphenyl)piperazine and isopropylsulfonyl chloride.

C26H35N3O5S.C2HF3O2 (615.67) LCMS(ESI): 502.3 (M+H+).

[4-(2,5-Dimethoxyphenyl)piperazin-1-yl]-[1-(4-methoxybenzenesulfonyl)-3,4-trans-4-phenylpyrrolidin-3-yl]methanone trifluoroacetate is obtained in analogy to example 1 from the commercially available reagents methyl (E)-cinnamate, N-(methoxymethyl)-N-(trimethylsilylmethyl)benzylamine, 1-(2,5-dimethoxyphenyl)piperazine and 4-methoxybenzenesulfonyl chloride.

C30H35N3O6S.C2HF3O2 (679.72), LCMS(ESI): 566.0 (M+H+).

EXAMPLE 79

[4-(2,5-Dimethoxyphenyl)piperazin-1-yl]-[1-(4-methoxybenzenesulfonyl)-3,4-trans-4-phenylpyrrolidin-3-yl]methanone trifluoroacetate

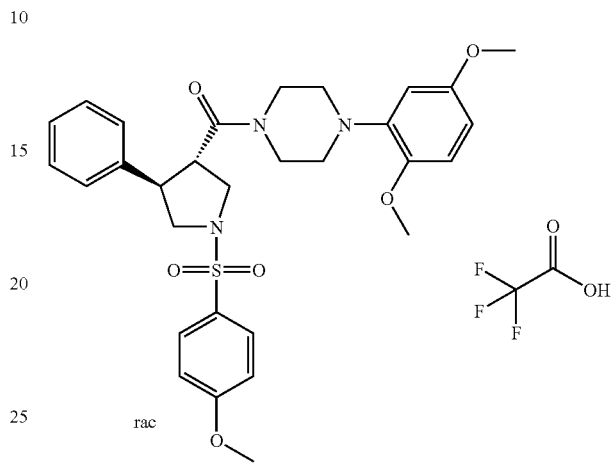

rac

EXAMPLE 80

[4-2,5-Dimethoxyphenyl)piperazin-1-yl]-[3,4-trans-4-phenyl-1-(toluene-3-sulfonyl)pyrrolidin-3-yl]methanone trifluoroacetate

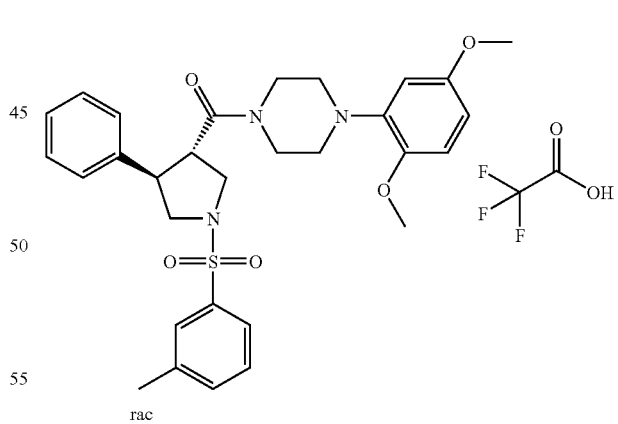

rac

[4-2,5-Dimethoxyphenyl)piperazin-1-yl]-[3,4-trans-4-phenyl-1-(toluene-3-sulfonyl)pyrrolidin-3-yl]methanone trifluoroacetate is obtained in analogy to example 1 from the commercially available reagents methyl (E)-cinnamate, N-(methoxymethyl)-N-(trimethylsilylmethyl)benzylamine, 1-(2,5-dimethoxyphenyl)piperazine and 3-methylbenzenesulfonyl chloride.

C30H35N3O5S.C2HF3O2 (663.72), LCMS(ESI): 550.0 (M+H+).

EXAMPLE 81

[1-(3,5-Dimethoxyisoxazole-4-sulfonyl)-3,4-trans-4-phenylpyrrolidin-3-yl]-[4-(2,5-dimethylphenyl)piperazin-1-yl]methanone trifluoroacetate

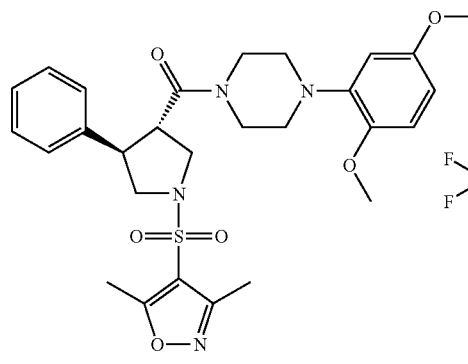

rac

[1-(3,5-Dimethoxyisoxazole-4-sulfonyl)-3,4-trans-4-phenylpyrrolidin-3-yl]-[4-(2,5-dimethylphenyl)piperazin-1-yl]methanone trifluoroacetate is obtained in analogy to example 1 from the commercially available reagents methyl (E)-cinnamate, N-(methoxymethyl)-N-(trimethylsilylmethyl)benzylamine, 1-(2,5-dimethoxyphenyl)piperazine and 3,5-dimethylisoxazole-4-sulfonyl chloride.

C28H34N4O6S.C2HF3O2 (668.69), LCMS(ESI): 555.0 (M+H$^+$).

EXAMPLE 82

[4-(2,5-Dimethoxyphenyl)piperazin-1-yl]-[1-(3-methoxybenzenesulfonyl)-3,4-trans-4-phenylpyrrolidin-3-yl]methanone trifluoroacetate

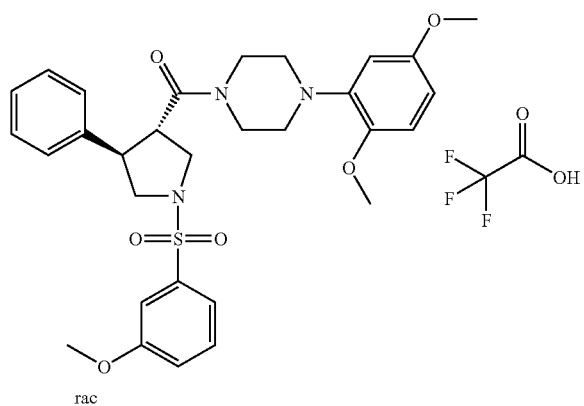

rac

[4-(2,5-Dimethoxyphenyl)piperazin-1-yl]-[1-(3-methoxybenzenesulfonyl)-3,4-trans-4-phenylpyrrolidin-3-yl]methanone trifluoroacetate is obtained in analogy to example 1 from the commercially available reagents methyl (E)-cinnamate, N-(methoxymethyl)-N-(trimethylsilylmethyl)benzylamine, 1-(2,5-dimethoxyphenyl)piperazine and 3-methoxybenzenesulfonyl chloride.

C30H35N3O6S.C2HF3O2 (679.72), LCMS(ESI): 566.0 (M+H$^+$).

EXAMPLE 83

[1-(Benzo[1,2,5]oxadiazole-4-sulfonyl)-3,4-trans-4-phenylpyrrolidin-3-yl]-[4-1-(2,5-dimethoxyphenyl)piperazin-1-yl]methanone trifluoroacetate

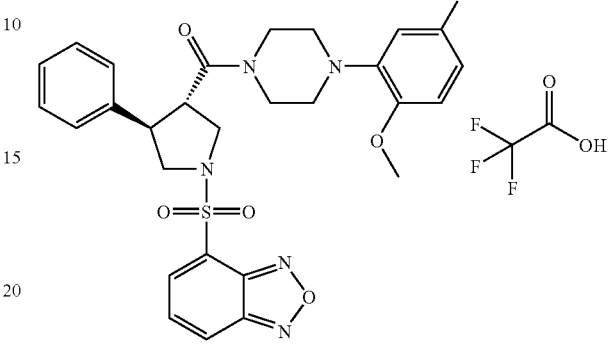

rac

[1-(Benzo[1,2,5]oxadiazole-4-sulfonyl)-3,4-trans-4-phenylpyrrolidin-3-yl]-[4-(2,5-dimethoxyphenyl)piperazin-1-yl]methanone trifluoroacetate is obtained in analogy to example 1 from the commercially available reagents methyl (E)-cinnamate, N-(methoxymethyl)-N-(trimethylsilylmethyl)benzylamine, 1-1-(2,5-dimethoxyphenyl)piperazine and benzo[1,2,5]oxadiazole-4-sulfonyl chloride.

C29H31N5O6S.C2HF3O2 (691.69), LCMS(ESI): 578.0 (M+H$^+$).

EXAMPLE 84

[4-(2,5-Dimethoxyphenyl)piperazin-1-yl]-[3,4-trans-4-phenyl-1-(thiophene-2-sulfonyl)pyrrolidin-3-yl]methanone trifluoroacetate

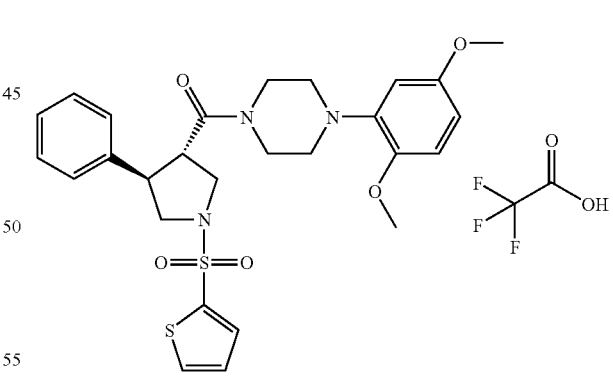

rac

[4-(2,5-Dimethoxyphenyl)piperazin-1-yl]-[3,4-trans-4-phenyl-1-(thiophene-2-sulfonyl)pyrrolidin-3-yl]methanone trifluoroacetate is obtained in analogy to example 1 from the commercially available reagents methyl (E)-cinnamate, N-(methoxymethyl)-N-(trimethylsilylmethyl)benzylamine, 1-(2,5-dimethoxyphenyl)piperazine and thiophene-2-sulfonyl chloride.

C27H31N3O5S2.C2HF3O2 (655.72), LCMS(ESI): 542.0 (M+H$^+$).

EXAMPLE 85

[[4-(2,5-Dichlorophenyl)piperazin-1-yl]-[3,4-trans-4-phenyl-1-(toluene-2-sulfonyl)pyrrolidin-3-yl]methanone trifluoroacetate

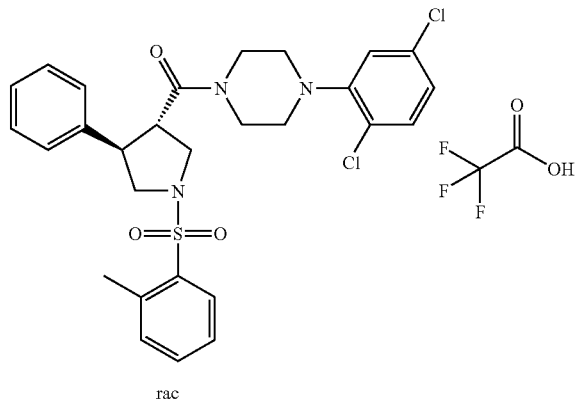

rac

[[4-(2,5-Dimethoxyphenyl)piperazin-1-yl]-[3,4-trans-4-phenyl-1-(thiophene-2-sulfonyl)pyrrolidin-3-yl]methanone trifluoroacetate is obtained in analogy to example 1 from the commercially available reagents methyl (E)-cinnamate, N-(methoxymethyl)-N-(trimethylsilylmethyl)benzylamine, 1-(2,5-dichlorophenyl)piperazine and 2-methylbenzenesulfonyl chloride.

28H29C12N3O3S.C2HF3O2 (672.56), LCMS(ESI): 558.1 (M+H$^+$).

EXAMPLE 86

[4-(2,6-Dimethoxyphenyl)piperazin-1-yl]-[1-(3-methoxybenzenesulfonyl)-3,4-trans-4-phenylpyrrolidin-3-yl]methanone

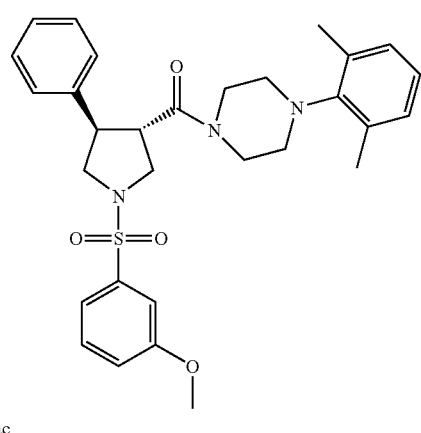

rac

[4-(2,6-Dimethoxyphenyl)piperazin-1-yl]-[1-(3-methoxybenzenesulfonyl)-3,4-trans-4-phenylpyrrolidin-3-yl]methanone is obtained in analogy to example 1 from the commercially available reagents methyl (E)-cinnamate, N-(methoxymethyl)-N-(trimethylsilylmethyl)benzylamine, 1-(2,6-dimethoxy-phenyl)piperazine and 3-methoxybenzenesulfonyl chloride.

C30H35N3O4S (533.70), LCMS(ESI): 534.4 (M+H$^+$).

EXAMPLE 87

[3,4-trans-4-Benzo[1,3]dioxol-5-yl-1-(3,5-dimethylisoxazole-4-sulfonyl)-pyrrolidin-3-yl]-[4-(2,5-dimethylphenyl)piperazin-1-yl]methanone trifluoroacetate

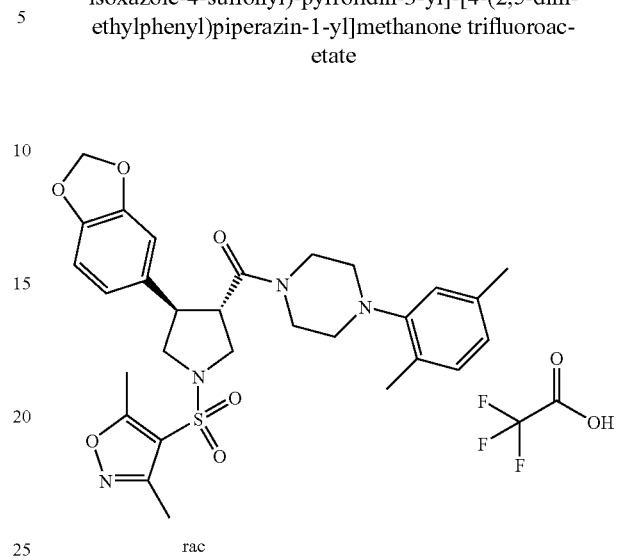

rac

[3,4-trans-4-Benzo[1,3]dioxol-5-yl-1-(3,5-dimethylisoxazole-4-sulfonyl)-pyrrolidin-3-yl]-[4-(2,5-dimethylphenyl)piperazin-1-yl]methanone trifluoroacetate is obtained in analogy to example 1 from the commercially available reagents benzo[1,3]dioxole-5-carbaldehyde, methyl (triphenylphosphoranylidene)acetate, N-(methoxymethyl)-N-(trimethylsilylmethyl)benzylamine, 1-(2,5-dimethylphenyl)piperazine and 3,5-dimethylisoxazole-4-sulfonyl chloride.

C29H34N4O6S.C2HF3O2 (680.71), LCMS(ESI): 567.3 (M+H$^+$).

EXAMPLE 88

[3,4-trans-4-Benzo[1,3]dioxol-5-yl-1-(3-methoxybenzenesulfonyl)pyrrolidin-3-yl]-[4-(2,5-dimethylphenyl)piperazin-1-yl]methanone trifluoroacetate

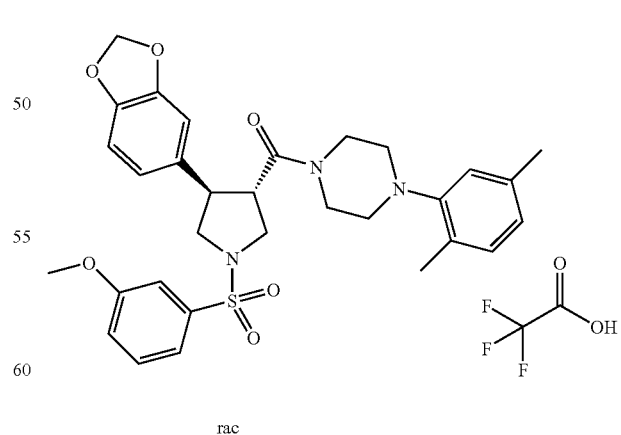

rac

[3,4-trans-4-Benzo[1,3]dioxol-5-yl-1-(3-methoxybenzenesulfonyl)pyrrolidin-3-yl]-[4-(2,5-dimethylphenyl)piperazin-1-yl]methanone trifluoroacetate is obtained in analogy to example 1 from the commercially available reagents benzo[1,3]dioxole-5-carbaldehyde, methyl (triphenylphosphoranylidene)-acetate, N-(methoxymethyl)-N-(trimethylsilylmethyl)benzylamine, 1-(2,5-dimethylphenyl)piperazine and 3-methoxybenzenesulfonyl chloride.

C31H35N3O6S.C2HF3O2 (691.73), LCMS(ESI): 578.4 (M+H⁺).

EXAMPLE 89

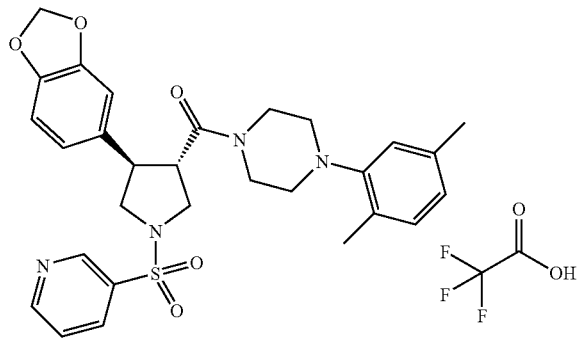

[3,4-trans-4-Benzo[1,3]dioxol-5-yl-1-(pyridine-3-sulfonyl)pyrrolidin-3-yl]-[4-(2,5-dimethylphenyl)piperazin-1-yl]methanone trifluoroacetate is obtained in analogy to example 1 from the commercially available reagents benzo[1,3]dioxole-5-carbaldehyde, methyl (triphenylphosphoranylidene)-acetate, N-(methoxymethyl)-N-(trimethylsilylmethyl)benzylamine, 1-(2,5-dimethylphenyl)piperazine and pyridine-3-sulfonyl chloride.

C29H32N4O5S.C2HF3O2 (662.69), LCMS(ESI): 549.3 (M+H⁺).

EXAMPLE 90

[[1-(3,5-Dimethylisoxazole-4-sulfonyl)-3,4-trans-4-methylpyrrolidin-3-yl]-[4-(2,5-dimethylphenyl)piperazin-1-yl]methanone trifluoroacetate

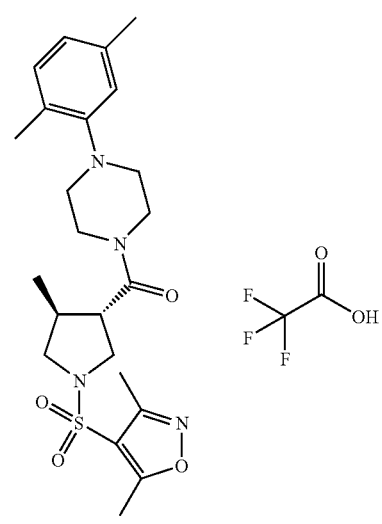

[[1-(3,5-Dimethylisoxazole-4-sulfonyl)-3,4-trans-4-methylpyrrolidin-3-yl]-[4-(2,5-dimethylphenyl)piperazin-1-yl]methanone trifluoroacetate is obtained in analogy to example 1 from the commercially available reagents acetaldehyde, methyl (triphenylphosphoranylidene)acetate, N-(methoxymethyl)-N-(trimethylsilylmethyl)benzylamine, 1-(2,5-dimethylphenyl)piperazine and 3,5-dimethylisoxazole-4-sulfonyl chloride.

C23H32N4O4S.C2HF3O2 (574.62), LCMS(ESI): 461.2 (M+H⁺).

EXAMPLE 91

[3,4-trans-4-(2,5-Dimethylphenyl)piperazin-1-yl]-[1-(3-methoxybenzene-sulfonyl)-4-methylpyrrolidin-3-yl]methanone trifluoroacetate

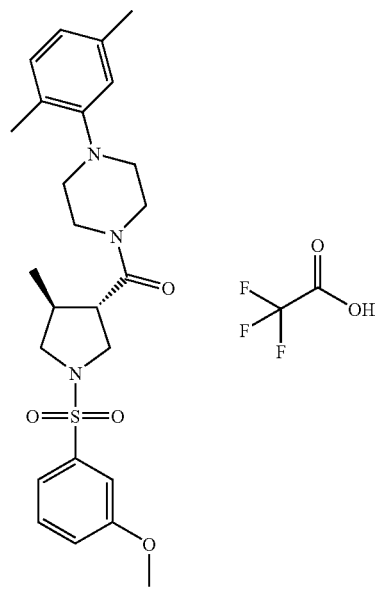

[3,4-trans-4-(2,5-Dimethylphenyl)piperazin-1-yl]-[1-(3-methoxybenzene-sulfonyl)-4-methylpyrrolidin-3-yl]methanone trifluoroacetate is obtained in analogy to example 1 from the commercially available reagents acetaldehyde, methyl (triphenylphosphoranylidene)acetate, N-(methoxymethyl)-N-(trimethylsilylmethyl)benzylamine, 1-(2,5-dimethyl-phenyl)piperazine and 3-methoxybenzenesulfonyl chloride.

C25H33N3O4S.C2HF3O2 (585.65), LCMS(ESI): 472.2 (M+H⁺).

EXAMPLE 92

[3,4-trans-4-(2,5-Dimethylphenyl)piperazin-1-yl]-[4-methyl-1-(pyridine-3-sulfonyl)pyrrolidin-3-yl]methanone trifluoroacetate

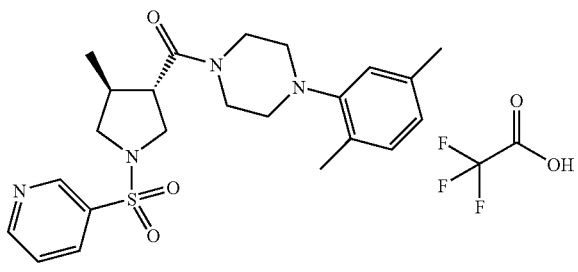

[3,4-trans-4-(2,5-Dimethylphenyl)piperazin-1-yl]-[4-methyl-1-(pyridine-3-sulfonyl)pyrrolidin-3-yl]methanone trifluoroacetate is obtained in analogy to example 1 from the commercially available reagents acetaldehyde, methyl (triphenylphosphoranylidene)acetate, N-(methoxymethyl)-N-(trimethylsilylmethyl)benzylamine, 1-(2,5-dimethylphenyl)piperazine and pyridine-3-sulfonyl chloride.

C23H30N4O3S.C2HF3O2 (556.60), LCMS(ESI): 443.2 (M+H$^+$).

EXAMPLE 93

[3,4-trans-4-Benzyl-1-(3,5-dimethylisoxazole-4-sulfonyl)pyrrolidin-3-yl]-[4-(2,5-dimethylphenyl)piperazin-1-yl]methanone trifluoroacetate

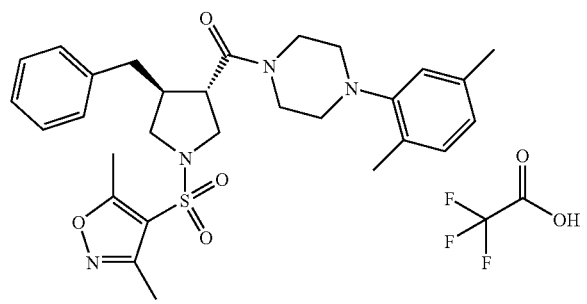

[3,4-trans-4-Benzyl-1-(3,5-dimethylisoxazole-4-sulfonyl)pyrrolidin-3-yl]-[4-(2,5-dimethylphenyl)piperazin-1-yl]methanone trifluoroacetate is obtained in analogy to example 1 from the commercially available reagents phenylacetaldehyde, methyl (triphenylphosphoranylidene)acetate, N-(methoxymethyl)-N-(trimethylsilylmethyl)benzylamine, 1-(2,5-dimethylphenyl)piperazine and 3,5-dimethylisoxazole-4-sulfonyl chloride.

C29H36N4O4S.C2HF3O2 (650.72), LCMS(ESI): 537.3 (M+H$^+$).

EXAMPLE 94

[3,4-trans-4-Benzyl-1-(3-methoxybenzenesulfonyl)pyrrolidin-3-yl]-[4-(2,5-dimethylphenyl)piperazin-1-yl]methanone trifluoroacetate

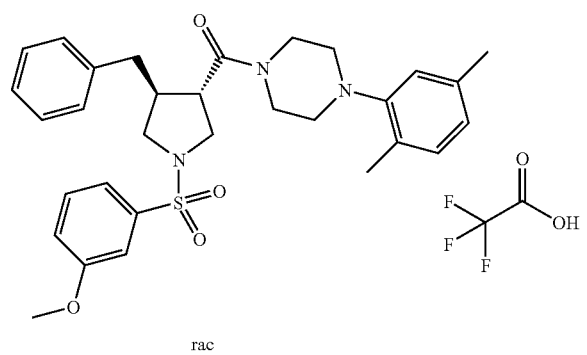

[3,4-trans-4-Benzyl-1-(3-methoxybenzenesulfonyl)pyrrolidin-3-yl]-[4-(2,5-dimethylphenyl)piperazin-1-yl]methanone trifluoroacetate is obtained in analogy to example 1 from the commercially available reagents phenylacetaldehyde, methyl (triphenylphosphoranylidene)acetate, N-(methoxymethyl)-N-(trimethylsilylmethyl)benzylamine, 1-(2,5-dimethyl-phenyl)piperazine and 3-methoxybenzenesulfonyl chloride.

C31H37N3O4S.C2HF3O2 (661.75), LCMS(ESI): 548.3 (M+H$^+$).

EXAMPLE 95

[1-(3,5-Dimethyl isoxazole-4-sulfonyl)-3,4-trans-4-isopropylpyrrolidin-3-yl]-[4-(2,5-dimethylphenyl)piperazin-1-yl]methanone trifluoroacetate

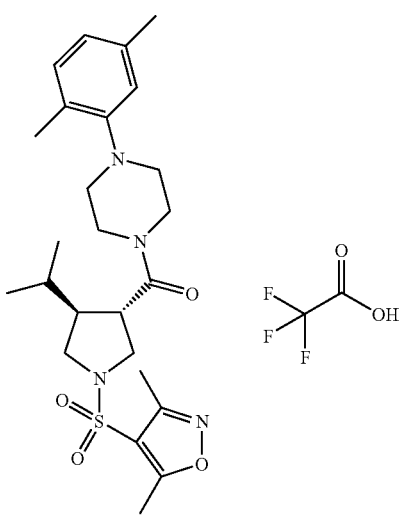

[1-(3,5-Dimethyl isoxazole-4-sulfonyl)-3,4-trans-4-isopropylpyrrolidin-3-yl]-[4-(2,5-dimethylphenyl)piperazin-1-yl]methanone trifluoroacetate is obtained in analogy to example 1 from the commercially available reagents 2-methylpropionaldehyde, methyl (triphenylphosphoranylidene)acetate, N-(methoxymethyl)-N-(trimethylsilylmethyl)benzylamine, 1-(2,5-dimethylphenyl)piperazine and 3,5-dimethylisoxazole-4-sulfonyl chloride.

C25H36N4O4S.C2HF3O2 (602.78), LCMS(ESI): 489.3 (M+H$^+$).

EXAMPLE 96

[4-(2,5-Dimethylphenyl)piperazin-1-yl]-[3,4-trans-4-isopropyl-1-(3-methoxy-benzenesulfonyl)pyrrolidin-3-yl]methanone trifluoroacetate

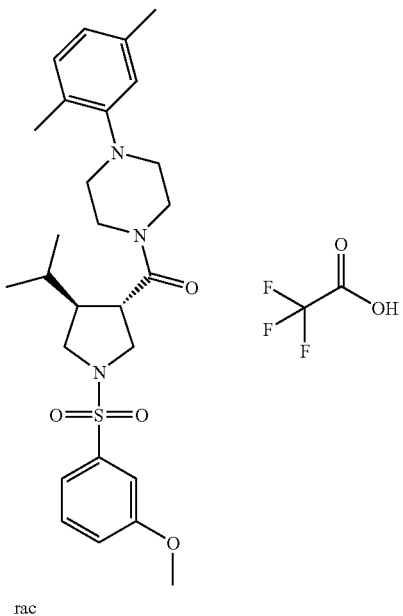

rac

[4-(2,5-Dimethylphenyl)piperazin-1-yl]-[3,4-trans-4-isopropyl-1-(3-methoxy-benzenesulfonyl)pyrrolidin-3-yl]methanone trifluoroacetate is obtained in analogy to example 1 from the commercially available reagents acetaldehyde, methyl (triphenylphosphoranylidene)acetate, N-(methoxymethyl)-N-(trimethylsilylmethyl)benzylamine, 1-(2,5-dimethyl-phenyl)piperazine and 3-methoxybenzenesulfonyl chloride.

C27H37N3O4S.C2HF3O2 (613.70), LCMS(ESI): 500.3 (M+H$^+$).

EXAMPLE 97

[1-(3,5-Dimethylisoxazole-4-sulfonyl)-3,4-trans-4-(tetrahydrofuran-3-yl)-pyrrolidin-3-yl]-[4-(2,5-dimethylphenyl)piperazin-1-yl]methanone trifluoroacetate

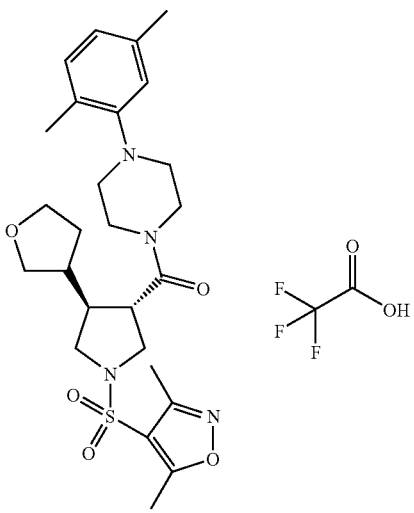

rac

[1-(3,5-Dimethylisoxazole-4-sulfonyl)-3,4-trans-4-(tetrahydrofuran-3-yl)-pyrrolidin-3-yl]-[4-(2,5-dimethylphenyl)piperazin-1-yl]methanone trifluoroacetate is obtained in analogy to example 1 from the commercially available reagents furan-2-carbaldehyde, methyl (triphenylphosphoranylidene)acetate, N-(methoxymethyl)-N-(trimethylsilylmethyl)benzylamine, 1-(2,5-dimethylphenyl)piperazine and 3,5-dimethylisoxazole-4-sulfonyl chloride.

C26H36N4O5S.C2HF3O2 (630.69), LCMS(ESI): 517.3 (M+H$^+$).

EXAMPLE 98 sulfonyl chloride [1-(3,5-Dimethylisoxazole-4-sulfonyl)-3,4-trans-4-o-tolyl-pyrrolidin-3-yl]-[4-(2,5-dimethylphenyl)piperazin-1-yl]methanone trifluoroacetate

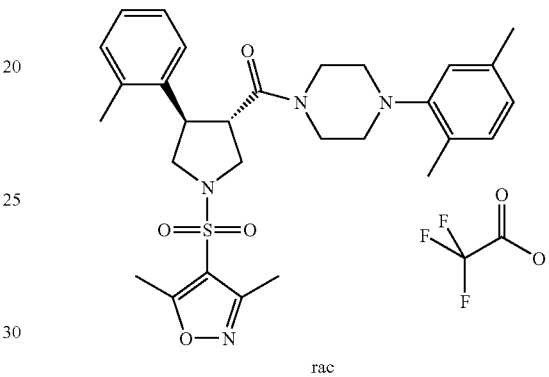

rac

[1-(3,5-Dimethylisoxazole-4-sulfonyl)-3,4-trans-4-o-tolylpyrrolidin-3-yl]-[4-(2,5-dimethylphenyl)piperazin-1-yl]methanone trifluoroacetate is obtained in analogy to example 1 from the commercially available reagents 2-methyl-benzaldehyde, methyl (triphenylphosphoranylidene)acetate, N-(methoxymethyl)-N-(trimethylsilylmethyl)benzylamine, 1-(2,5-dimethylphenyl)piperazine and 3,5-dimethylisoxazole-4-sulfonyl chloride.

C29H36N4O4S.C2HF3O2 (650.72), LCMS(ESI): 537.3 (M+H$^+$).

EXAMPLE 99

[4-(2,5-Dimethylphenyl)piperazin-1-yl]-[1-(3-methoxybenzenesulfonyl)-3,4-trans-4-o-tolylpyrrolidin-3-yl]methanone trifluoroacetate

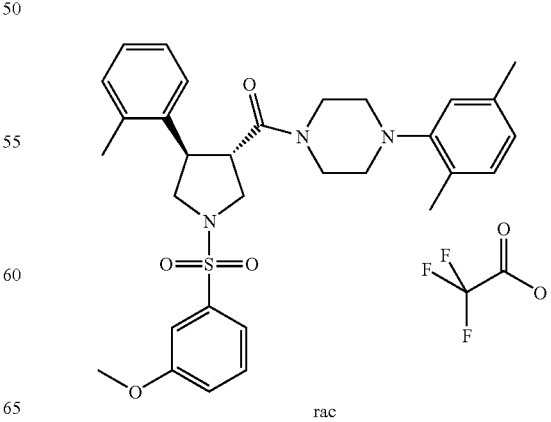

rac

[4-(2,5-Dimethylphenyl)piperazin-1-yl]-[1-(3-methoxy-benzenesulfonyl)-3,4-trans-4-o-tolylpyrrolidin-3-yl]methanone trifluoroacetate is obtained in analogy to example 1 from the commercially available reagents 2-methyl-benzaldehyde, methyl (triphenylphosphoranylidene)acetate, N-(methoxymethyl)-N-(trimethylsilylmethyl)benzylamine, 1-(2,5-dimethyl-phenyl)piperazine and 3-methoxybenzenesulfonyl chloride.

C31H37N3O4S.C2HF3O2 (661.75), LCMS(ESI): 548.3 (M+H⁺).

EXAMPLE 100

[4-(2,5-Dimethylphenyl)piperazin-1-yl]-[1-(pyridine-3-sulfonyl)-3,4-trans-4-o-tolylpyrrolidin-3-yl]methanone trifluoroacetate

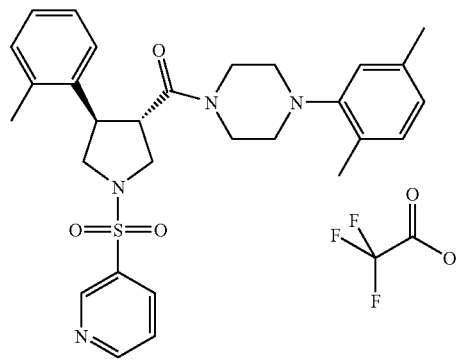

rac

[4-(2,5-Dimethylphenyl)piperazin-1-yl]-[1-(pyridine-3-sulfonyl)-3,4-trans-4-o-tolylpyrrolidin-3-yl]methanone trifluoroacetate is obtained in analogy to example 1 from the commercially available reagents 2-methyl-benzaldehyde, methyl (triphenylphosphoranylidene)acetate, N-(methoxymethyl)-N-(trimethylsilylmethyl)benzylamine, 1-(2,5-dimethyl-phenyl)piperazine and pyridine-3-sulfonyl chloride.

C29H34N4O3S.C2HF3O2 (632.71), LCMS(ESI): 519.3 (M+H⁺).

EXAMPLE 101

[1-(3,5-Dimethylisoxazole-4-sulfonyl)-3,4-trans-4-m-tolylpyrrolidin-3-yl]-[4-(2,5-dimethylphenyl)piperazin-1-yl]methanone trifluoroacetate

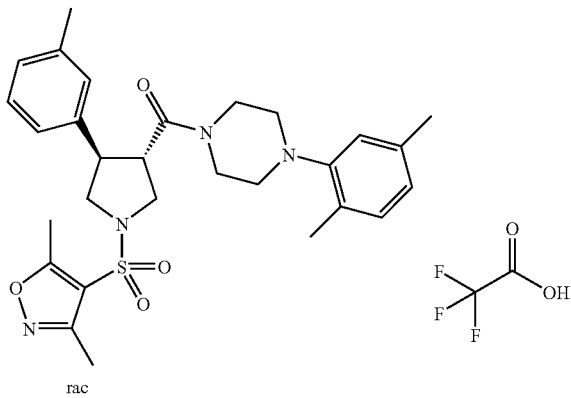

rac

[1-(3,5-Dimethyl isoxazole-4-sulfonyl)-3,4-trans-4-m-tolylpyrrolidin-3-yl]-[4-(2,5-dimethylphenyl)piperazin-1-yl]methanone trifluoroacetate is obtained in analogy to example 1 from the commercially available reagents 3-methyl-benzaldehyde, methyl (triphenylphosphoranylidene)acetate, N-(methoxymethyl)-N-(trimethylsilylmethyl)benzylamine, 1-(2,5-dimethylphenyl)piperazine and 3,5-dimethylisoxazole-4-sulfonyl chloride.

C29H36N4O4S.C2HF3O2 (650.72), LCMS(ESI): 537.3 (M+H⁺).

EXAMPLE 102

[4-(2,5-Dimethylphenyl)piperazin-1-yl]-[1-(3-methoxybenzenesulfonyl)-3,4-trans-4-m-tolylpyrrolidin-3-yl]methanone trifluoroacetate

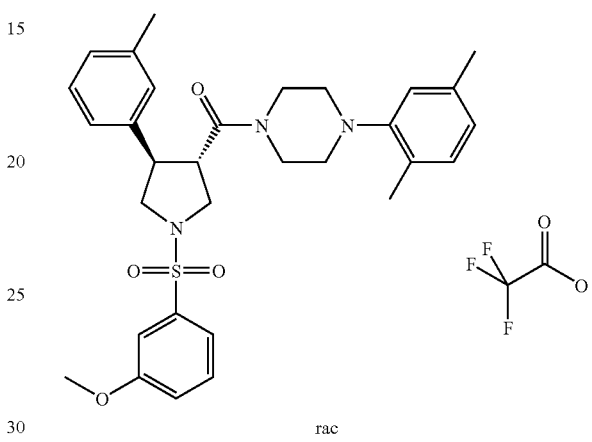

rac

[4-(2,5-Dimethylphenyl)piperazin-1-yl]-[1-(3-methoxybenzenesulfonyl)-3,4-trans-4-m-tolylpyrrolidin-3-yl]methanone trifluoroacetate is obtained in analogy to example 1 from the commercially available reagents 3-methyl-benzaldehyde, methyl (triphenylphosphoranylidene)acetate, N-(methoxymethyl)-N-(trimethylsilylmethyl)benzylamine, 1-(2,5-dimethyl-phenyl)piperazine and 3-methoxybenzenesulfonyl chloride.

C31H37N3O4S.C2HF3O2 (661.75), LCMS(ESI): 548.3 (M+H⁺).

EXAMPLE 103

[1-(3,5-Dimethylisoxazole-4-sulfonyl)-3,4-trans-4-(3,5-dimethylisoxazol-4-yl)pyrrolidin-3-yl]-[4-(2,5-dimethylphenyl)piperazin-1-yl]methanone trifluoroacetate

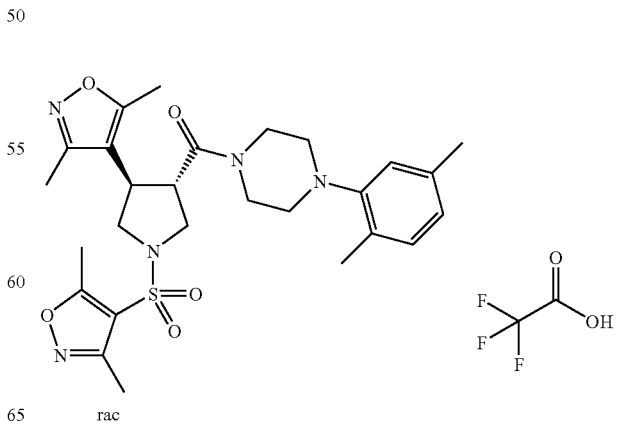

rac

[1-(3,5-Dimethylisoxazole-4-sulfonyl)-3,4-trans-4-(3,5-dimethylisoxazol-4-yl)pyrrolidin-3-yl]-[4-(2,5-dimethylphenyl)piperazin-1-yl]methanone trifluoroacetate is obtained in analogy to example 1 from the commercially available reagents 3,5-dimethylisoxazole-4-carbaldehyde, methyl (triphenylphosphoranylidene)acetate, N-(methoxymethyl)-N-(trimethylsilylmethyl)benzylamine, 1-(2,5-dimethylphenyl)piperazine and 3,5-dimethylisoxazole-4-sulfonyl chloride.

C27H35N5O5S.C2HF3O2 (655.70), LCMS(ESI): 542.3 (M+H$^+$).

EXAMPLE 104

[3,4-trans-4-(3,5-Dimethylisoxazol-4-yl)-1-(3-methoxybenzenesulfonyl)-pyrrolidin-3-yl]-[4-(2,5-dimethylphenyl)piperazin-1-yl]methanone trifluoroacetate

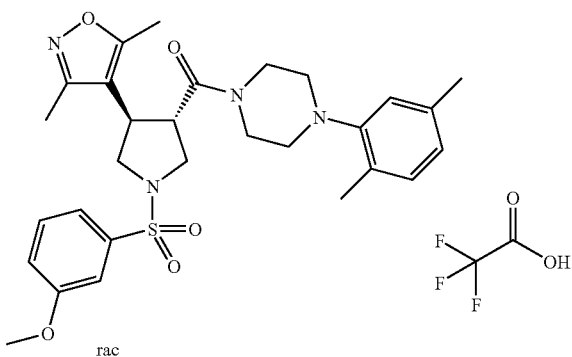

[3,4-trans-4-(3,5-Dimethylisoxazol-4-yl)-1-(3-methoxybenzenesulfonyl)-pyrrolidin-3-yl]-[4-(2,5-dimethylphenyl)piperazin-1-yl]methanone trifluoroacetate is obtained in analogy to example 1 from the commercially available reagents 3,5-dimethylisoxazole-4-carbaldehyde, methyl (triphenylphosphoranylidene)acetate, N-(methoxymethyl)-N-(trimethylsilylmethyl)benzylamine, 1-(2,5-dimethylphenyl)piperazine and 3-methoxybenzenesulfonyl chloride.

C29H36N4O5S.C2HF3O2.C2HF3O2 (666.72), LCMS(ESI): 553.3 (M+H$^+$).

EXAMPLE 105

[3,4-trans-4-(3,5-Dimethylisoxazol-4-yl)-1-(pyridine-3-sulfonyl)pyrrolidin-3-yl]-[4-(2,5-dimethylphenyl)piperazin-1-yl]methanone trifluoroacetate

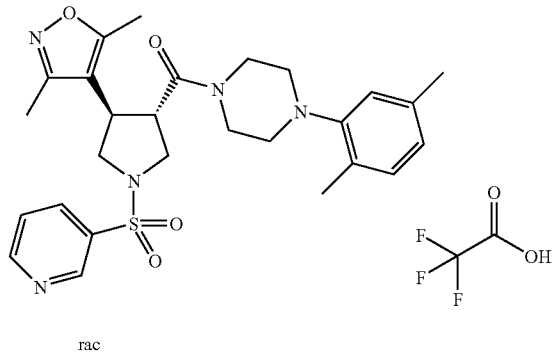

[3,4-trans-4-(3,5-Dimethylisoxazol-4-yl)-1-(pyridine-3-sulfonyl)pyrrolidin-3-yl]-[4-(2,5-dimethylphenyl)piperazin-1-yl]methanone trifluoroacetate is obtained in analogy to example 1 from the commercially available reagents 3,5-dimethylisoxazole-4-carbaldehyde, methyl (triphenylphosphoranylidene)acetate, N-(methoxymethyl)-N-(trimethylsilylmethyl)benzylamine, 1-(2,5-dimethylphenyl)piperazine and pyridine-3-sulfonyl chloride.

C27H33N5O4S.C2HF3O2 (637.68), LCMS(ESI): 524.2 (M+H$^+$).

EXAMPLE 106

[1-(3,5-Dimethylisoxazole-4-sulfonyl)-3,4-trans-4-(2,6-dimethylphenyl)pyrrolidin-3-yl]-[4-(2,5-dimethylphenyl)piperazin-1-yl]methanone trifluoroacetate

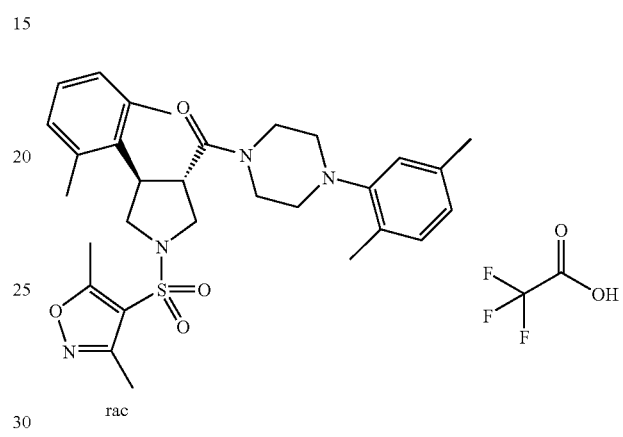

[1-(3,5-Dimethylisoxazole-4-sulfonyl)-3,4-trans-4-(2,6-dimethylphenyl)pyrrolidin-3-yl]-[4-(2,5-dimethylphenyl)piperazin-1-yl]methanone trifluoroacetate is obtained in analogy to example 1 from the commercially available reagents 2,3-dimethylbenzaldehyde, methyl (triphenylphosphoranylidene)acetate, N-(methoxymethyl)-N-(trimethylsilylmethyl)benzylamine, 1-(2,5-dimethylphenyl)piperazine and 3,5-dimethylisoxazole-4-sulfonyl chloride.

C30H38N4O4S.C2HF3O2 (664.75), LCMS(ESI): 551.3 (M+H$^+$).

EXAMPLE 107

[1-(3,5-Dimethyl isoxazole-4-sulfonyl)-3,4-trans-4-(4-methyl-3,4-dihydro-2H-benzo[1,4]oxazin-7-yl)pyrrolidin-3-yl]-[4-(2,5-dimethylphenyl)piperazin-1-yl]methanone trifluoroacetate

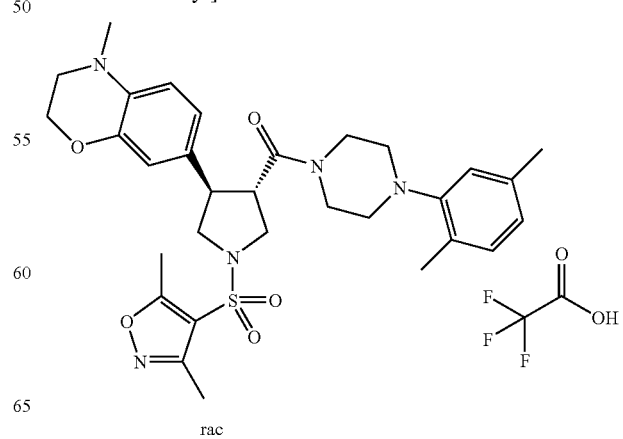

[1-(3,5-Dimethylisoxazole-4-sulfonyl)-3,4-trans-4-(4-methyl-3,4-dihydro-2H-benzo[1,4]oxazin-7-yl)pyrrolidin-3-yl]-[4-(2,5-dimethylphenyl)piperazin-1-yl]methanone trifluoroacetate is obtained in analogy to example 1 from the commercially available reagents 4-methyl-3,4-dihydro-2H-benzo[1,4]oxazine-7-carbaldehyde, methyl (triphenylphosphoranylidene)-acetate, N-(methoxymethyl)-N-(trimethylsilylmethyl)benzylamine, 1-(2,5-dimethylphenyl)piperazine and 3,5-dimethylisoxazole-4-sulfonyl chloride.

C31H39N5O5S.C2HF3O2 (707.76), LCMS(ESI): 594.2 (M+H$^+$).

EXAMPLE 108

[3,4-trans-4-Benzo[1,3]dioxol-4-yl-1-(3,5-dimethylisoxazole-4-sulfonyl)-pyrrolidin-3-yl]-[4-(2,5-dimethylphenyl)piperazin-1-yl]methanone trifluoroacetate

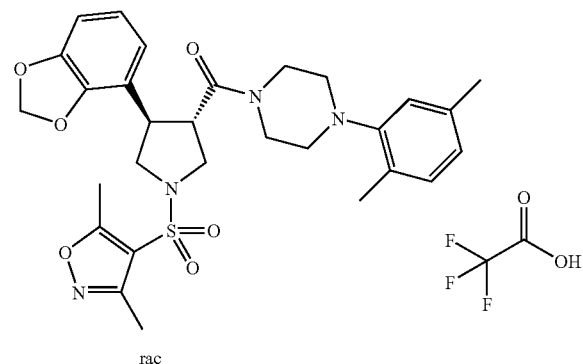

[3,4-trans-4-Benzo[1,3]dioxol-4-yl-1-(3,5-dimethylisoxazole-4-sulfonyl)-pyrrolidin-3-yl]-[4-(2,5-dimethylphenyl)piperazin-1-yl]methanone trifluoroacetate is obtained in analogy to example 1 from the commercially available reagents 4-methyl-3,4-dihydro-2H-benzo[1,4]oxazine-7-carbaldehyde, methyl (triphenylphosphoranylidene)acetate, N-(methoxymethyl)-N-(trimethylsilylmethyl)benzylamine, 1-(2,5-dimethyl-phenyl)piperazine and 3,5-dimethylisoxazole-4-sulfonyl chloride.

C29H34N4O6S.C2HF3O2 (680.71), LCMS(ESI): 567.2 (M+H$^+$).

EXAMPLE 109

[4-(2,5-Dimethylphenyl)piperazin-1-yl]-[1-(3-methoxybenzenesulfonyl)-3,4-trans-4-(4-methyl-3,4-dihydro-2H-benzo[1,4]oxazin-7-yl)pyrrolidin-3-yl]-methanone trifluoroacetate

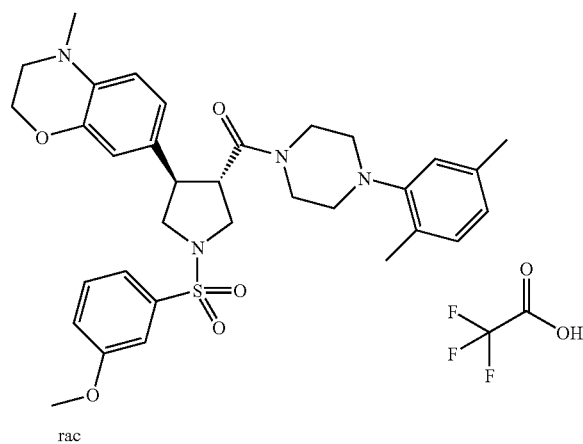

[4-(2,5-Dimethylphenyl)piperazin-1-yl]-[1-(3-methoxybenzenesulfonyl)-3,4-trans-4-(4-methyl-3,4-dihydro-2H-benzo[1,4]oxazin-7-yl)pyrrolidin-3-yl]-methanone trifluoroacetate is obtained in analogy to example 1 from the commercially available reagents 4-methyl-3,4-dihydro-2H-benzo[1,4]oxazine-7-carbaldehyde, methyl (triphenylphosphoranylidene)-acetate, N-(methoxymethyl)-N-(trimethylsilylmethyl)benzylamine, 1-(2,5-dimethylphenyl)piperazine and 3,5-dimethylisoxazole-4-sulfonyl chloride.

C33H40N4O5S.C2HF3O2 (718.80), LCMS(ESI): 605.2 (M+H$^+$).

Examples of Syntheses by Method B:

EXAMPLE 110

[4-(2,5-Dimethylphenyl)piperazin-1-yl]-[1-(3-methoxybenzenesulfonyl)-3,4-trans-4-thiophen-3-ylpyrrolidin-3-yl]methanone trifluoroacetate

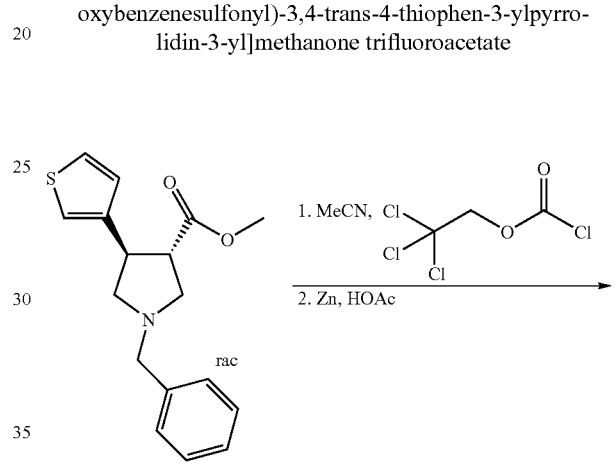

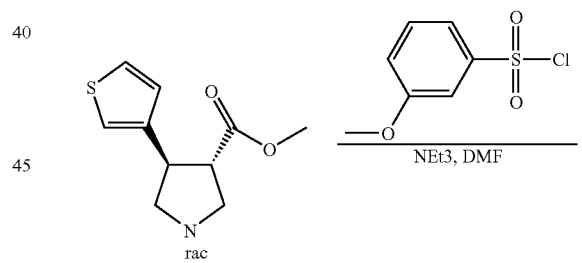

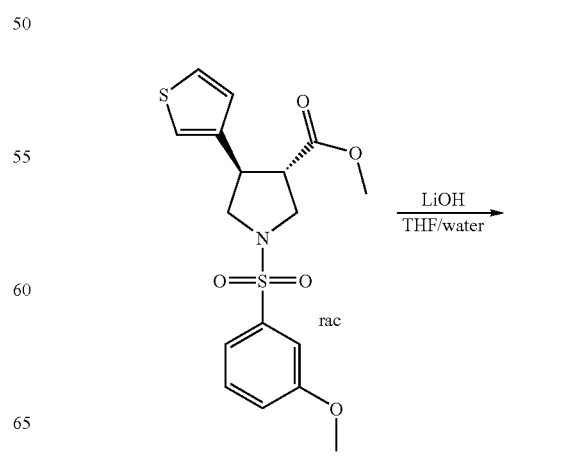

-continued

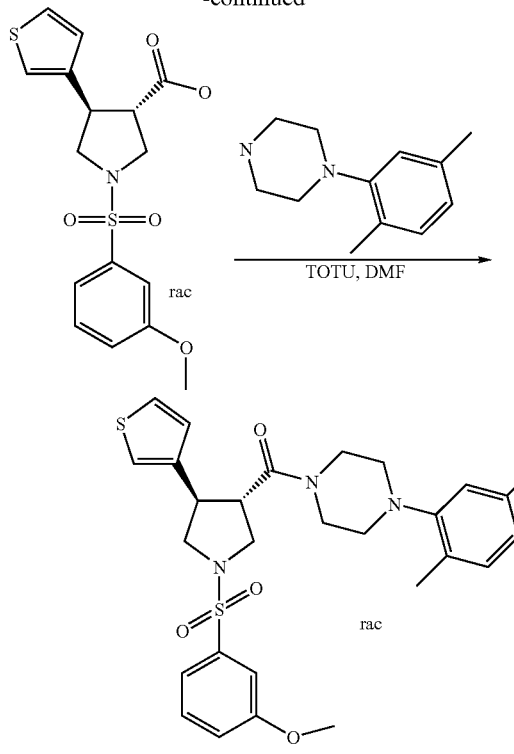

Example 110

Methyl 3,4-trans-4-thiophen-3-ylpyrrolidine-3-carboxylate trifluoroacetate

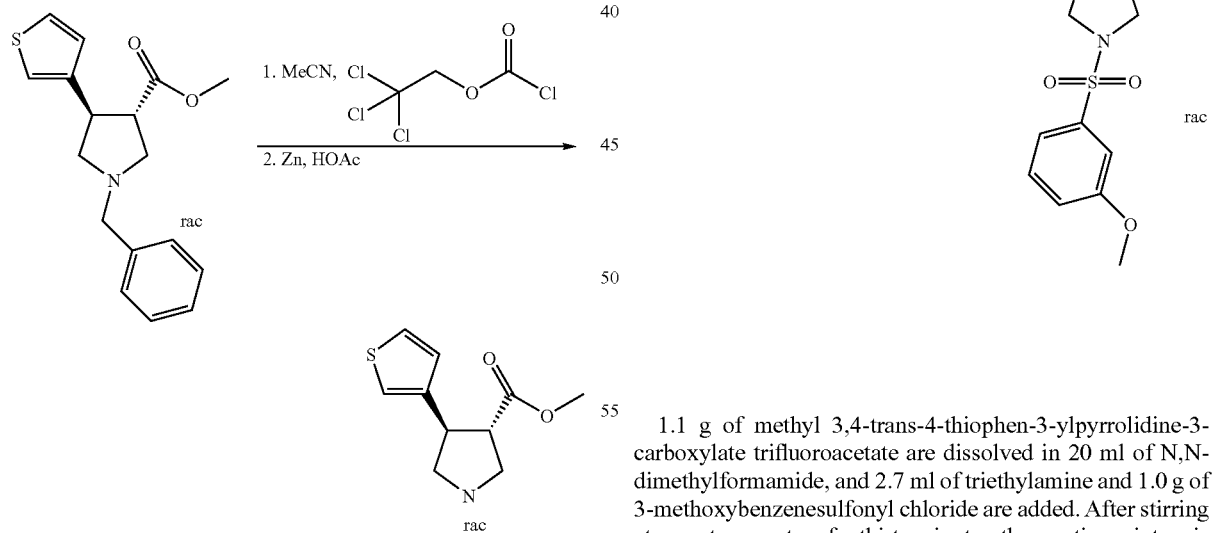

2.0 g of methyl 1-benzyl-4-thiophen-3-ylpyrrolidine-3-carboxylate (prepared in analogy to example 1 from the commercially available reagents thiophene-2-carbaldehyde, methyl (triphenylphosphoranylidene)acetate and N-(methoxymethyl)-N-(trimethylsilylmethyl)benzylamine) are dissolved in 30 ml of dry acetonitrile and, at room temperature, 0.90 ml of 2,2,2-trichloroethyl chloroformate is added. After stirring at room temperature for thirty minutes, the acetonitrile is removed in vacuo and the residue is taken up in 40 ml of glacial acetic acid. 845 mg of zinc are added, and the reaction mixture is stirred at room temperature. After two hours, the reaction mixture is filtered and washed with dichloromethane, and the filtrate is then concentrated in vacuo. The residue is mixed with 100 ml of toluene and concentrated in vacuo. The residue is purified by RP-HPLC. 2.2 g of methyl 3,4-trans-4-thiophen-3-ylpyrrolidine-3-carboxylate trifluoroacetate are obtained as an oil.

C10H13NO2S.C2HF3O2 (325.30), LCMS(ESI): 212.2 (M+H$^+$).

Methyl 1-(3-methoxybenzenesulfonyl)-3,4-trans-4-thiophen-3-ylpyrrolidine-3-carboxylate

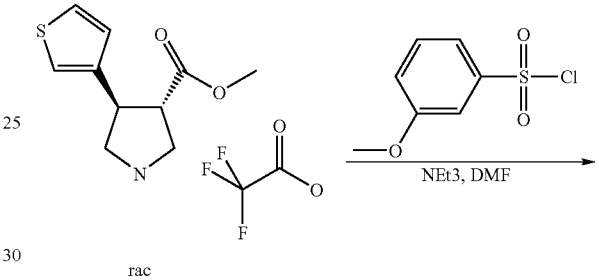

1.1 g of methyl 3,4-trans-4-thiophen-3-ylpyrrolidine-3-carboxylate trifluoroacetate are dissolved in 20 ml of N,N-dimethylformamide, and 2.7 ml of triethylamine and 1.0 g of 3-methoxybenzenesulfonyl chloride are added. After stirring at room temperature for thirty minutes, the reaction mixture is diluted by adding 100 ml of ethyl acetate and washed three times with 30 ml of saturated sodium bicarbonate solution each time. The organic phase is dried over MgSO4 and then the solvent is removed in vacuo. 900 mg of methyl 1-(3-methoxybenzenesulfonyl)-3,4-trans-4-thiophen-3-ylpyrrolidine-3-carboxylate are obtained as an oil.

C17H19NO5S2 (381.47), LCMS(ESI): 382.3 (M+H$^+$).

1-(3-Methoxybenzenesulfonyl)-3,4-trans-4-thiophen-3-ylpyrrolidine-3-carboxylic acid

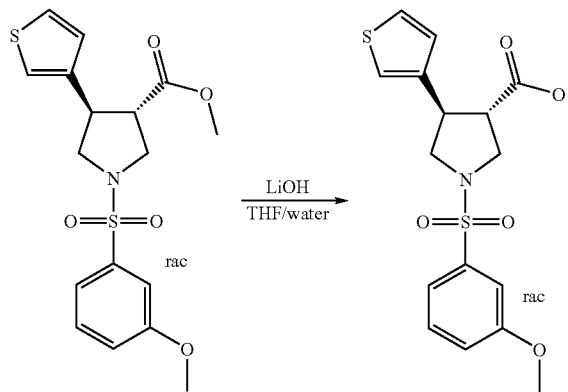

900 mg of methyl 1-(3-methoxybenzenesulfonyl)-3,4-trans-4-thiophen-3-ylpyrrolidine-3-carboxylate are dissolved in a mixture of 10 ml of tetrahydrofuran and 5 ml of water, and 280 g of lithium hydroxide are added. The reaction mixture is stirred at room temperature. After one hour, the reaction mixture is acidified by adding a few drops of concentrated hydrochloric acid. The reaction mixture is extracted three times with 50 ethyl acetate each time. The combined organic phases are dried over MgSO4 and then the solvent is removed in vacuo. 800 mg of 1-(3-methoxybenzenesulfonyl)-3,4-trans-4-thiophen-3-ylpyrrolidine-3-carboxylic acid are obtained as an oil.

C16H17NO5S2 (367.45), LCMS(ESI): 368.3 (M+H⁺).

[4-(2,5-Dimethylphenyl)piperazin-1-yl]-[1-(3-methoxybenzenesulfonyl)-3,4-trans-4-thiophen-3-ylpyrrolidin-3-yl]methanone trifluoroacetate

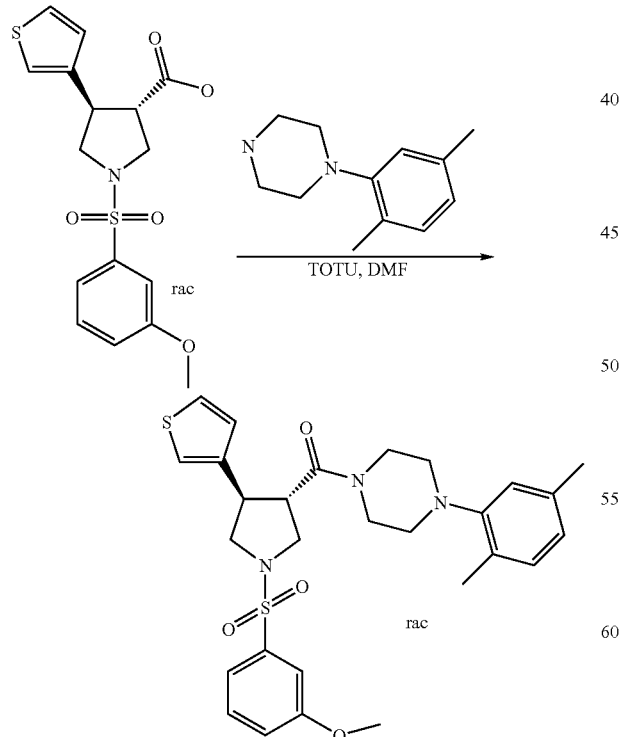

Example 110

800 mg of 1-(3-methoxybenzenesulfonyl)-3,4-trans-4-thiophen-3-yl-pyrrolidine-3-carboxylic acid, 0.4 ml of triethylamine and 440 mg of 1-(2,5-dimethylphenyl)piperazine are dissolved in 15 ml of N,N-dimethylformamide, and 750 mg of O-[cyano(ethoxycarbonyl)methylene-amino]-1,1,3,3-tetramethyluronium tetrafluoroborate are added in portions. The reaction mixture is stirred at room temperature. After one hour, the reaction mixture is diluted by adding 100 ml of ethyl acetate and washed five times with 30 ml of saturated sodium bicarbonate solution each time. The organic phase is dried over MgSO4 and then the solvent is removed in vacuo. The residue is purified by RP-HPLC. 320 mg of [4-(2,5-dimethylphenyl)piperazin-1-yl]-[1-(3-methoxybenzenesulfonyl)-3,4-trans-4-thiophen-3-ylpyrrolidin-3-yl]methanone trifluoroacetate are obtained as lyophilizate.

C28H33N3O4S2.C2HF3O2 (653.74); LCMS(ESI): 540.6 (M+H⁺).

EXAMPLE 111

[1-(3,5-Dimethylisoxazole-4-sulfonyl)-3,4-trans-4-thiophen-3-ylpyrrolidin-3-yl]-[4-(2,5-dimethylphenyl)piperazin-1-yl]methanone trifluoroacetate

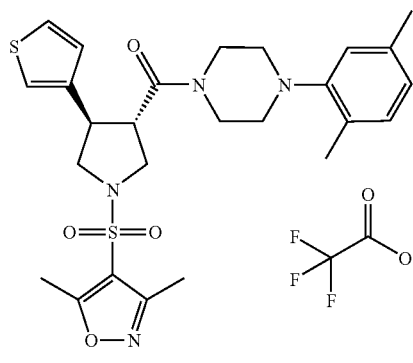

[1-(3,5-Dimethylisoxazole-4-sulfonyl)-3,4-trans-4-thiophen-3-ylpyrrolidin-3-yl]-[4-(2,5-dimethylphenyl)piperazin-1-yl]methanone trifluoroacetate is obtained in analogy to example 110 from the commercially available reagents thiophene-2-carbaldehyde, methyl (triphenylphosphoranylidene)acetate, N-(methoxymethyl)-N-(trimethylsilylmethyl)benzylamine, 1-(2,5-dimethylphenyl)piperazine and 3,5-dimethylisoxazole-4-sulfonyl chloride.

C26H32N4O4S2.C2HF3O2 (642.72), LCMS(ESI): 529.3 (M+H⁺).

EXAMPLE 112

[1-(3,5-Dimethylisoxazole-4-sulfonyl)-3,4-trans-4-pyridin-3-ylpyrrolidin-3-yl]-[4-(2,5-dimethylphenyl)piperazin-1-yl]methanone trifluoroacetate

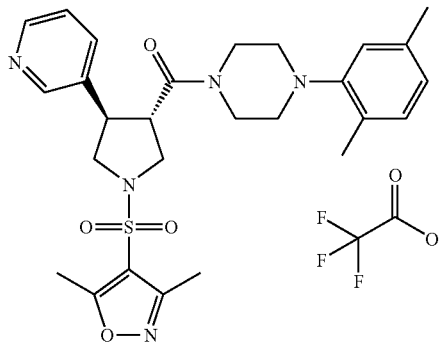

rac

[1-(3,5-Dimethylisoxazole-4-sulfonyl)-3,4-trans-4-pyridin-3-yl pyrrolidin-3-yl]-[4-(2,5-dimethylphenyl)piperazin-1-yl]methanone trifluoroacetate is obtained in analogy to example 110 from the commercially available reagents pyridine-3-carbaldehyde, methyl (triphenylphosphoranylidene)acetate, N-(methoxymethyl)-N-(trimethylsilylmethyl)benzylamine, 1-(2,5-dimethylphenyl)piperazine and 3,5-dimethylisoxazole-4-sulfonyl chloride.

C27H33N5O4S.C2HF3O2 (637.68), LCMS(ESI): 524.3 (M+H$^+$).

EXAMPLE 113

[4-(2,5-Dimethylphenyl)piperazin-1-yl]-[1-(pyridine-3-sulfonyl)-3,4-trans-4-pyridin-3-ylpyrrolidin-3-yl]methanone trifluoroacetate

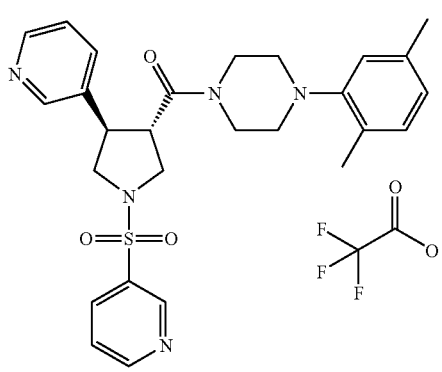

rac

[4-(2,5-Dimethylphenyl)piperazin-1-yl]-[1-(pyridine-3-sulfonyl)-3,4-trans-4-pyridin-3-ylpyrrolidin-3-yl]methanone trifluoroacetate is obtained in analogy to example 110 from the commercially available reagents pyridine-3-carbaldehyde, methyl (triphenylphosphoranylidene)acetate, N-(methoxymethyl)-N-(trimethylsilylmethyl)benzylamine, 1-(2,5-dimethylphenyl)piperazine and pyridine-3-sulfonyl chloride.

C27H31N5O3S.C2HF3O2 (619.67), LCMS(ESI): 506.3 (M+H$^+$).

EXAMPLE 114

[4-(2,5-Dimethylphenyl)piperazin-1-yl]-[3,4-trans-4-furan-3-yl-1-(3-methoxybenzenesulfonyl)pyrrolid 3-yl]methanone trifluoroacetate

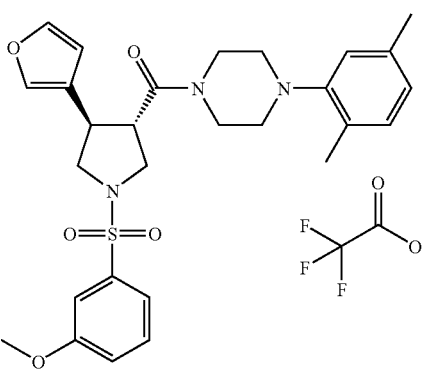

rac

[4-(2,5-Dimethylphenyl)piperazin-1-yl]-[3,4-trans-4-furan-3-yl-1-(3-methoxybenzenesulfonyl)pyrrolidin-3-yl]methanone trifluoroacetate is obtained in analogy to example 110 from the commercially available reagents furan-2-carbaldehyde, methyl (triphenylphosphoranylidene)-acetate, N-(methoxymethyl)-N-(trimethylsilylmethyl)benzylamine, 1-(2,5-dimethylphenyl)piperazine and 3-methoxybenzenesulfonyl chloride.

C28H33N3O5S.C2HF3O2 (637.68), LCMS(ESI): 524.3 (M+H$^+$).

EXAMPLE 115

[1-(3,5-Dimethylisoxazole-4-sulfonyl)-3,4-trans-4-furan-3-yl pyrrolidin-3-yl]-[4-(2,5-dimethylphenyl)piperazin-1-yl]methanone trifluoroacetate

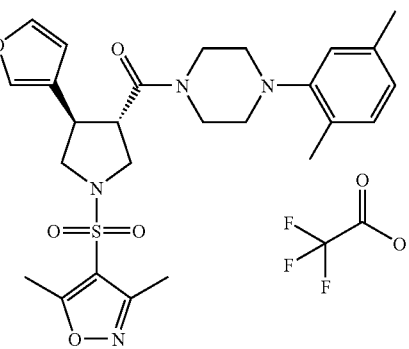

rac

[1-(3,5-Dimethylisoxazole-4-sulfonyl)-3,4-trans-4-furan-3-ylpyrrolidin-3-yl]-[4-(2,5-dimethylphenyl)piperazin-1-yl] methanone trifluoroacetate is obtained in analogy to example 110 from the commercially available reagents furan-2-carbaldehyde, methyl (triphenylphosphoranylidene)acetate, N-(methoxymethyl)-N-(trimethylsilylmethyl)benzylamine, 1-(2,5-dimethylphenyl)piperazine and 3,5-dimethylisoxazole-4-sulfonyl chloride.

C26H32N4O5S.C2HF3O2 (626.66), LCMS(ESI): 513.3 (M+H$^+$).

EXAMPLE 116

[4-(2,5-Dimethylphenyl)piperazin-1-yl]-[3,4-trans-4-furan-3-yl-1-(pyridine-3-sulfonyl)pyrrolidin-3-yl]methanone trifluoroacetate

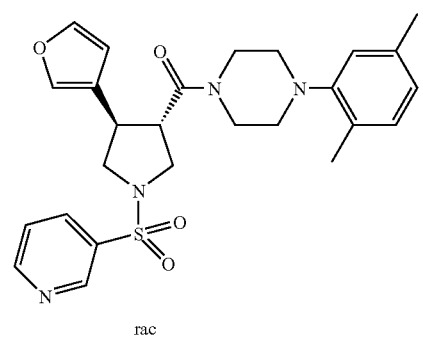

[4-(2,5-Dimethylphenyl)piperazin-1-yl]-[3,4-trans-4-furan-3-yl-1-(pyridine-3-sulfonyl)pyrrolidin-3-yl]methanone trifluoroacetate is obtained in analogy to example 110 from the commercially available reagents furan-2-carbaldehyde, methyl (triphenylphosphoranylidene)acetate, N-(methoxymethyl)-N-(trimethylsilylmethyl)benzylamine, 1-(2,5-dimethylphenyl)piperazine and pyridine-3-sulfonyl chloride.

C26H30N4O4S.C2HF3O2 (608.64), LCMS(ESI): 495.2 (M+H$^+$).

Examples of Syntheses by Method D:

EXAMPLE 117

[4-(2,5-Dimethylphenyl)piperazin-1-yl]-[3,4-cis-4-phenyl-1-(thiophene-2-sulfonyl)pyrrolidin-3-yl]methanone

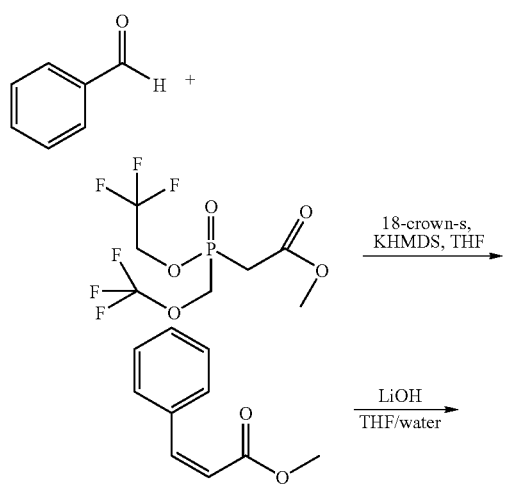

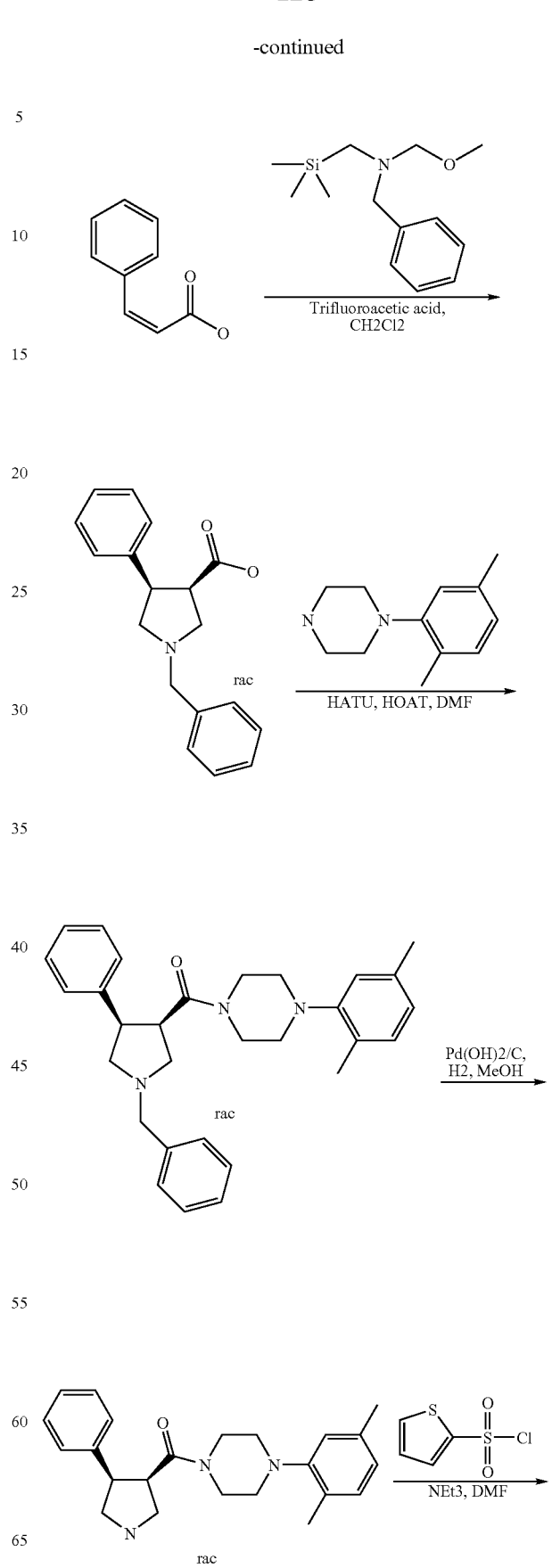

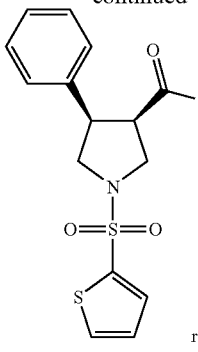

rac
Example 117

Methyl (Z)-3-phenylacrylate

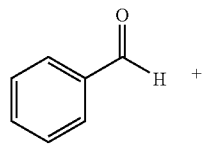

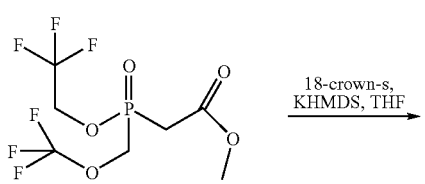

18-crown-s, KHMDS, THF

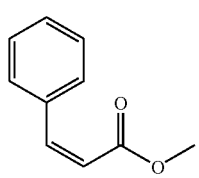

9.4 g of 18-crown-6 and 1.7 ml of methyl [bis(2,2,2-trifluoroethoxy)-phosphoryl]acetate are dissolved under argon in 120 ml of dry tetrahydro-furan and cooled to −78° C. 14.3 ml of a 0.5 molar solution of potassium bis(trimethylsilyl)amide in toluene are added to this mixture, followed by 0.85 ml of benzaldehyde. After stirring at −78° C. for thirty minutes, the reaction mixture is quenched by adding saturated ammonium chloride solution and extracted with five portions each of 50 ml of ethyl acetate. The combined organic phases are dried over MgSO4 and then the solvent is removed in vacuo. The residue is purified on silica gel with n-heptane:ethyl acetate=20:1 as eluent. 1.1 g of methyl (Z)-3-phenylacrylate are obtained as an oil.

C10H10O2 (162.19), LCMS(ESI): 163.2 (M+H$^+$). Rf (n-heptane:ethyl acetate=2:1)=0.62, The coupling constant of the olefinic protons in the 1H-NMR is 12 Hz.

(Z)-3-Phenylacrylic acid

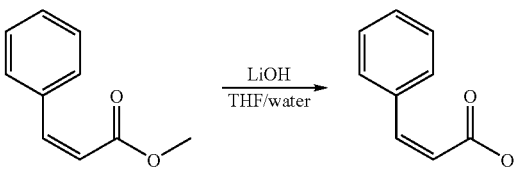

1.1 g of methyl (Z)-3-phenylacrylate are dissolved in a mixture of 30 ml of tetrahydrofuran and 10 ml of water, and 340 mg of lithium hydroxide are added. The mixture is stirred at 60° C. After four hours, the reaction mixture is acidified by adding one molar hydrochloric acid solution and extracted five times with 50 ml of ethyl acetate each time. The combined organic phases are dried over MgSO4 and then the solvent is removed in vacuo. 900 mg of (Z)-3-phenylacrylic acid are obtained as an oil.

C9H8O2 (148.16), LCMS(ESI): 149.2 (M+H$^+$), coupling constant of the olefinic protons in the 1H-NMR is 12 Hz.

1-Benzyl-3,4-cis-4-phenylpyrrolidine-3-carboxylic acid trifluoroacetate

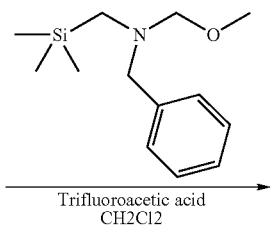

Trifluoroacetic acid
CH2Cl2

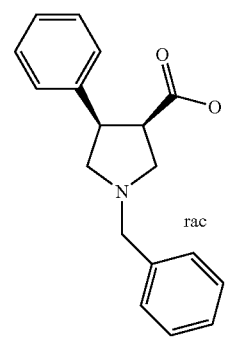

rac 2 ml of a one molar solution of trifluoroacetic acid in dichloromethane is added dropwise at 0° C. to a solution of 5.0 g of N-(methoxymethyl)-N-(trimethylsilylmethyl)benzylamine and 3 g of (Z)-3-phenylacrylic acid in 50 ml of dichloromethane. After stirring at room temperature for one hour, the solvent is removed in vacuo and the residue is purified by RP-HPLC. 1.14 g of 1-benzyl-3,4-cis-4-phenylpyrrolidine-3-carboxylic acid trifluoroacetate are obtained as a colorless oil.

C18H19NO2.C2HF3O2 (395.38), LCMS(ESI): 282.2 (M+H$^+$).

131

(1-Benzyl-3,4-cis-4-phenylpyrrolidin-3-yl)-[4-(2,5-dimethylphenyl)piperazin-1-yl]methanone trifluoroacetate

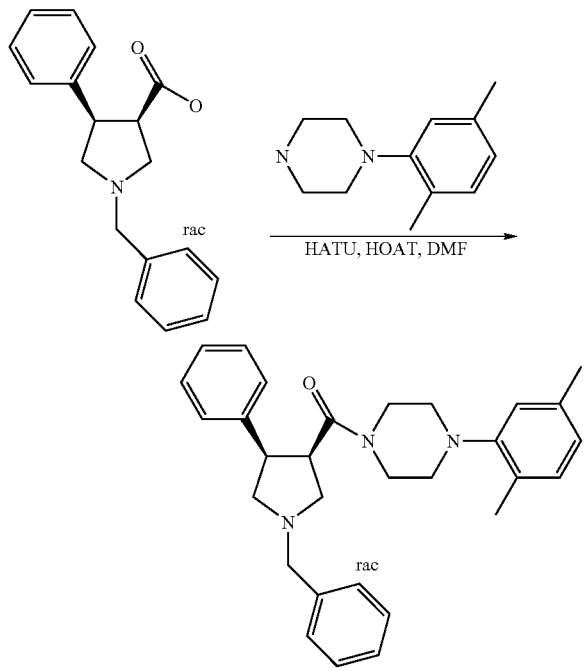

1.14 g of 1-benzyl-3,4-cis-4-phenylpyrrolidine-3-carboxylic acid trifluoroacetate, 980 mg of 1-(2,5-dimethylphenyl)piperazine, 3.0 ml of N,N-diisopropylethylamine, 840 mg of 1-hydroxy-7-azobenzotriazole and 2.4 g of O-(7-azabenzotriazol-1-yl)-N,N,N',N'-tetramethyluronium hexafluorophosphate are dissolved in 20 ml of N,N-dimethylformamide and stirred at room temperature for one hour. The reaction mixture is then diluted by adding 100 ml of ethyl acetate and washed with saturated sodium bicarbonate solution. The organic phase is separated off and dried over MgSO4, and the solvent is removed in vacuo. The residue is purified by RP-HPLC. 940 mg of (1-benzyl-3,4-cis-4-phenylpyrrolidin-3-yl)-[4-(2,5-dimethylphenyl)piperazin-1-yl]methanone trifluoroacetate are obtained as a colorless lyophilizate.

C30H35N3O.C2HF3O2 (567.65), LCMS(ESI): 454.6 (M+H$^+$).

[4-(2,5-Dimethylphenyl)piperazin-1-yl]-(3,4-cis-4-phenylpyrrolidin-3-yl)-methanone trifluoroacetate

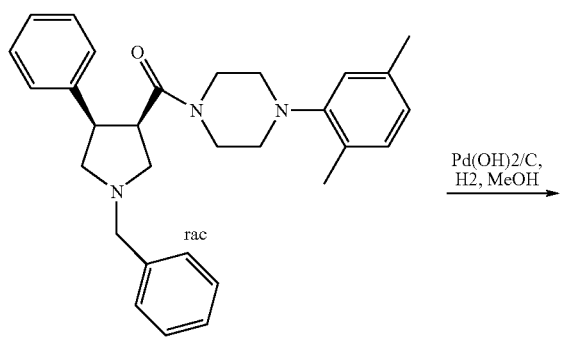

132

940 mg of (1-benzyl-3,4-cis-4-phenylpyrrolidin-3-yl)-[4-(2,5-dimethylphenyl)piperazin-1-yl]methanone trifluoroacetate are dissolved in 10 ml of methanol, 50 mg of palladium hydroxide on carbon, 20%, moist, are added. The mixture is stirred under an atmosphere of 5 bar of hydrogen for twenty-four hours. The catalyst is then filtered through Celite and washed with ethyl acetate, and the filtrate is concentrated in vacuo. 1.1 g of [4-(2,5-dimethylphenyl)piperazin-1-yl]-(3,4-cis-4-phenylpyrrolidin-3-yl)-methanone trifluoroacetate are obtained as a colorless oil.

C23H29N3O.C2HF3O2 (477.53), LCMS(ESI): 364.5 (M+H$^+$).

[4-(2,5-Dimethylphenyl)piperazin-1-yl]-[3,4-cis-4-phenyl-1-(thiophene-2-sulfonyl)pyrrolidin-3-yl]methanone

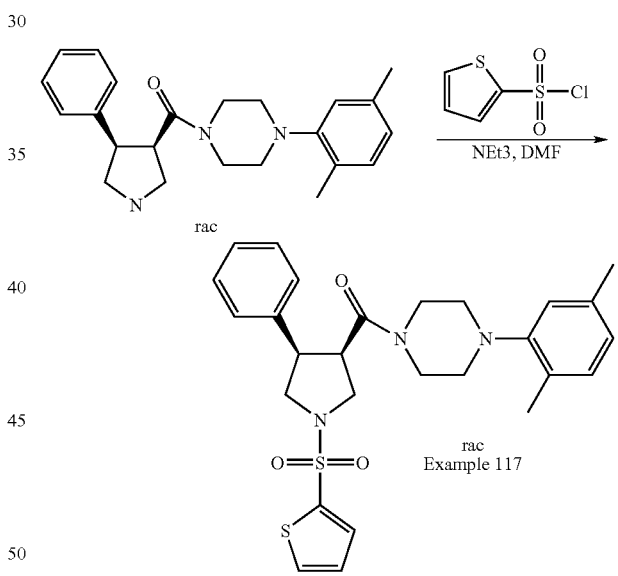

200 mg of [4-(2,5-dimethylphenyl)piperazin-1-yl]-(3,4-cis-4-phenylpyrrolidin-3-yl)methanone trifluoroacetate, 200 μl of N,N-diisopropylethylamine and 100 mg of 2-thiophenesulfonyl chloride are dissolved in 10 ml of N,N-dimethylformamide and stirred at room temperature. After one hour, the reaction mixture is diluted by adding 100 ml of ethyl acetate and washed with 50 ml of saturated sodium bicarbonate solution and three times 50 ml of water each time. The organic phase is separated off and dried over MgSO4, and the solvent is removed in vacuo. The residue is purified on silica gel with n-heptane:ethyl acetate=20:1→10:1→5:1→2:1 as eluent. 120 mg of [4-(2,5-dimethylphenyl)piperazin-1-yl]-[3,4-cis-4-phenyl-1-(thiophene-2-sulfonyl)pyrrolidin-3-yl]methanone are obtained as a white amorphous solid.

C27H31N3O3S2 (509.69), LCMS(ESI): 510.1 (M+H$^+$).

The racemate of [4-(2,5-dimethylphenyl)piperazin-1-yl]-[3,4-cis-4-phenyl-1-(thiophene-2-sulfonyl)pyrrolidin-3-yl]methanone was fractionated into the enantiomers by chiral phase chromatography. [4-(2,5-Dimethylphenyl)-piperazin-1-yl]-[(3R,4R)/(3S,4S)-4-phenyl-1-(thiophene-2-sulfonyl)-pyrrolidin-3-yl]methanone Example 117A (Chiracel OJ/37 250×4.6 mm, eluent methanol, Rt=9.4 min) and [4-(2,5-dimethylphenyl)piperazin-1-yl]-[(3S,4S)/(3R,4R)-4-phenyl-1-(thiophene-2-sulfonyl)pyrrolidin-3-yl]methanone Example 117B (Chiracel OJ/37 250×4.6 mm, eluent methanol, Rt=14.9 min) are obtained.

EXAMPLE 118

[1-(3,5-Dimethylisoxazole-4-sulfonyl)-3,4-cis-4-phenylpyrrolidin-3-yl]-[4-(2,5-dimethylphenyl)piperazin-1-yl]methanone trifluoroacetate

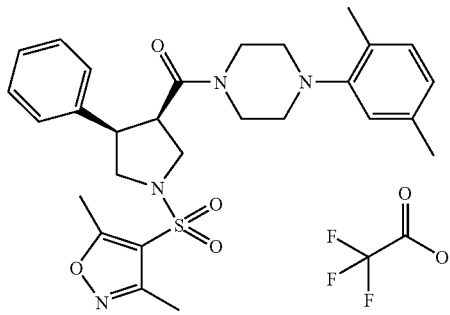

[1-(3,5-Dimethylisoxazole-4-sulfonyl)-3,4-cis-4-phenylpyrrolidin-3-yl]-[4-(2,5-dimethylphenyl)piperazin-1-yl]methanone trifluoroacetate is obtained in analogy to example 117 from the commercially available reagents benzaldehyde, methyl [bis(2,2,2-trifluoroethoxy)phosphoryl]acetate, N-(methoxymethyl)-N-(trimethylsilylmethyl)benzylamine, 1-(2,5-dimethyl-phenyl)piperazine and 3,5-dimethylisoxazole-4-sulfonyl chloride.

C28H34N4O4S.C2HF3O2 (636.70), LCMS(ESI): 523.3 (M+H$^+$).

EXAMPLE 119

[4-(2,5-Dimethylphenyl)piperazin-1-yl]-[1-(3-methoxybenzenesulfonyl)-3,4-cis-4-phenylpyrrolidin-3-yl]methanone trifluoroacetate

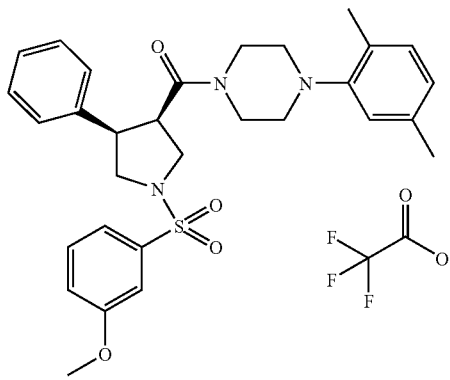

[4-(2,5-Dimethylphenyl)piperazin-1-yl]-[1-(3-methoxybenzenesulfonyl)-3,4-cis-4-phenylpyrrolidin-3-yl]methanone trifluoroacetate is obtained in analogy to example 117 from the commercially available reagents benzaldehyde, methyl [bis(2,2,2-trifluoroethoxy)phosphoryl]acetate, N-(methoxymethyl)-N-(trimethylsilylmethyl)benzylamine, 1-(2,5-dimethylphenyl)piperazine and 3-methoxybenzenesulfonyl chloride.

C30H35N3O4S.C2HF3O2 (647.72), LCMS(ESI): 534.3 (M+H$^+$).

The racemate of [[4-(2,5-dimethylphenyl)piperazin-1-yl]-[1-(3-methoxybenzenesulfonyl)-3,4-cis-4-phenylpyrrolidin-3-yl]methanone trifluoroacetate was fractionated into the enantiomers by chiral phase chromatography. [4-(2,5-Dimethylphenyl)piperazin-1-yl]-[1-[(3-methoxy-benzenesulfonyl)-(3R,4R)/(3S,4S)-cis-4-phenylpyrrolidin-3-yl]methanone Example 119A (Chiracel OJ/15 250×4.6 mm, eluent methanol, Rt=9.8 min) and [4-(2,5-dimethylphenyl)piperazin-1-yl]-[1-[(3-methoxybenzenesulfonyl)-(3S,4S)/(3R, 4R)-cis-4-phenylpyrrolidin-3-yl]methanone Example 119B (Chiracel OJ/15 250×4.6 mm, eluent methanol, Rt=17.3+ min) are obtained.

EXAMPLE 120

[4-(2,5-Dimethylphenyl)piperazin-1-yl]-[3,4-cis-4-phenyl-1-(pyridine-3-sulfonyl)pyrrolidin-3-yl]methanone trifluoroacetate

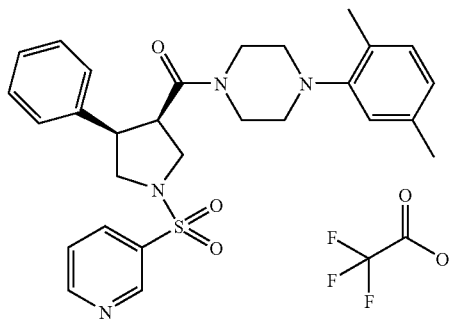

[4-(2,5-Dimethylphenyl)piperazin-1-yl]-[3,4-cis-4-phenyl-1-(pyridine-3-sulfonyl)pyrrolidin-3-yl]methanone trifluoroacetate is obtained in analogy to example 117 from the commercially available reagents benzaldehyde, methyl [bis(2,2,2-trifluoroethoxy)phosphoryl]acetate, N-(methoxymethyl)-N-(trimethylsilylmethyl)benzylamine, 1-(2,5-dimethylphenyl)piperazine and pyridine-3-sulfonyl chloride.

C28H32N4O3S.C2HF3O2 (618.68), LCMS(ESI): 505.2 (M+H$^+$).

The invention claimed is:
1. A compound of the formula Ia:

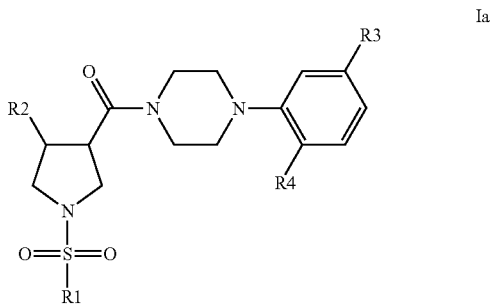

wherein:

R1 is selected from $(C_1-C_6)$-alkyl, where one or more hydrogens in the alkyl radical may be replaced by fluorine; phenyl, $(C_1-C_8)$-alkylene-phenyl, heterocyclyl, $(C_1-C_8)$-alkylene-heterocyclyl, where the phenyl or heterocycle radical may be substituted one or more times by a substituent selected from F, Cl, Br, $NO_2$, COO—$(C_1-C_6)$-alkyl, $(C_1-C_6)$-alkylene-O—$(C_1-C_6)$-alkyl, $OCF_3$, $(C_1-C_6)$-alkyl, CO—$(C_1-C_6)$-alkyl, phenyl, $SCF_3$, and $SF_5$;

and the heterocycle is selected from the group consisting of thiophene, quinoline, oxadiazole, isoxazole and pyridine and may be fused to a benzene ring;

R2 is selected from phenyl and heterocycle, where the phenyl or heterocycle radical may be substituted one or more times by a substituent selected from F, Cl, Br, $NO_2$, COO—$(C_1-C_6)$-alkyl, $(C_1-C_6)$-alkylene-O—$(C_1-C_6)$-alkyl, $OCF_3$, $(C_1-C_6)$-alkyl, CO—$(C_1-C_6)$-alkyl, phenyl, $SCF_3$, and $SF_5$ and the heterocycle is selected from the group consisting of dioxole, tetrahydrofuran, isoxazole, oxazine, thiophene and pyridine and may be fused to a benzene ring; and R3 and R4 are, independently of one another, selected from H, F, Cl, Br, $NO_2$, COO—$(C_1-C_6)$-alkyl, $(C_1-C_6)$-alkylene-O—$(C_1-C_6)$-alkyl, $OCF_3$, $(C_1-C_6)$-alkyl, CO—$(C_1-C_6)$-alkyl, phenyl, $SCF_3$, and $SF_5$;

where the compound of the following formula is excluded

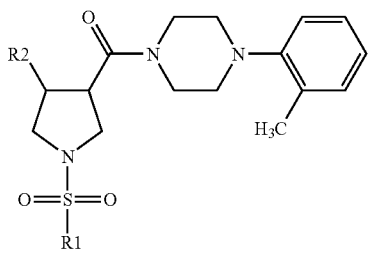

or a physiologically tolerated salt thereof.

2. A medicament comprising at least one compound of claim 1 in combination with at least one carrier or an excipient.

3. A medicament comprising at least one compound of claim 1 and at least one other active ingredient.

4. The medicament as claimed in claim 3, wherein the other active ingredient is selected from antidiabetics, hypoglycemic active ingredients, HMGCoA reductase inhibitors, cholesterol absorption inhibitors, PPAR gamma agonists, PPAR alpha agonists, PPAR alpha/gamma agonists, fibrates, MTP inhibitors, bile acid absorption inhibitors, CETP inhibitors, polymeric bile acid adsorbents, LDL receptor inducers, ACAT inhibitors, antioxidants, lipoprotein lipase inhibitors, ATP-citrate lyase inhibitors, squalene synthetase inhibitors, lipoprotein(a) antagonists, lipase inhibitors, insulins, sulfonylureas, biguanides, meglitinides, thiazolidinediones, α-glucosidase inhibitors, active ingredients which act on the ATP-dependent potassium channel of the beta cells, CART agonists, NPY agonists, MC4 agonists, orexin agonists, H3 agonists, TNF agonists, CRF agonists, CRF BP antagonists, urocortin agonists, β3 agonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, uncoupling protein 2 or 3 modulators, leptin agonists, DA agonists (bromocriptine, Doprexin), lipase/amylase inhibitors, PPAR modulators, RXR modulators or TR-β agonists or amphetamines.

5. A method for increasing HDL in the blood of a patient which comprises administering to said patient an effective amount of at least one compound of claim 1.

6. A method for the treatment of arteriosclerotic manifestations which comprises administering to a patient in need thereof an effective amount of at least one compound of claim 1.

7. A process for producing a medicament comprising, as the active ingredient, a compound of claim 1, which comprises mixing the active ingredient with a pharmaceutically suitable carrier and converting this mixture into a form suitable for administration.

* * * * *